(12) United States Patent
Na et al.

(10) Patent No.: US 12,138,308 B2
(45) Date of Patent: Nov. 12, 2024

(54) POLYMER COMPOSITE FOR HELICOBACTER PYLORI RECOGNITION AND COMPOSITION FOR PHOTODYNAMIC THERAPY COMPRISING SAME

(71) Applicant: eNBiaR Inc., Bucheon-si (KR)

(72) Inventors: Kun Na, Bucheon-si (KR); Byeong Nam Im, Yongin-si (KR)

(73) Assignee: eNBiaR Inc., Bucheon-si (KR)

( * ) Notice: Subject to any disclaimer, the term of this patent is extended or adjusted under 35 U.S.C. 154(b) by 846 days.

(21) Appl. No.: 17/277,285

(22) PCT Filed: Sep. 20, 2019

(86) PCT No.: PCT/KR2019/012197
§ 371 (c)(1),
(2) Date: May 30, 2021

(87) PCT Pub. No.: WO2020/060260
PCT Pub. Date: Mar. 26, 2020

(65) Prior Publication Data
US 2021/0283257 A1  Sep. 16, 2021

(30) Foreign Application Priority Data

Sep. 20, 2018 (KR) .................. 10-2018-0112824
Sep. 20, 2019 (KR) .................. 10-2019-0115725

(51) Int. Cl.
*A61K 41/00* (2020.01)
*A61K 47/54* (2017.01)
(Continued)

(52) U.S. Cl.
CPC ........ *A61K 41/0071* (2013.01); *A61K 47/549* (2017.08); *A61K 47/62* (2017.08);
(Continued)

(58) Field of Classification Search
None
See application file for complete search history.

(56) References Cited

FOREIGN PATENT DOCUMENTS

| JP | 09-509931 A | 10/1997 |
| JP | 2001-513819 A | 9/2001 |
| JP | 2003-508124 A | 3/2003 |
| KR | 10-2013-0034079 A | 4/2013 |

(Continued)

OTHER PUBLICATIONS

International Search Report for PCT/KR2019/012197 mailed Jan. 10, 2020 from Korean Intellectual Property Office.
(Continued)

*Primary Examiner* — Brian Gulledge
(74) *Attorney, Agent, or Firm* — Revolution IP, PLLC

(57) ABSTRACT

The present invention relates to a polymer complex for recognizing *Helicobacter pylori* and its uses, and in more detail, a water-soluble polymer-photosensitizer complex in which sialyllactose, which selectively binds to the surface of *Helicobacter pylori*, is conjugated, has excellent selectivity and binding power to the *Helicobacter pylori* strain, and the photosensitizer in the complex generates singlet oxygen when irradiated with laser to effectively induce the inactivation of *Helicobacter pylori* and it is intended to provide the complex as a polymer complex for recognizing *Helicobacter pylori* to effectively detect *Helicobacter pylori* in the gastrointestinal tract and to provide a *Helicobacter pylori* photodynamic therapy to solve the conventional antibiotic resistance problem.

2 Claims, 38 Drawing Sheets

(51) Int. Cl.
  *A61K 47/56* (2017.01)
  *A61K 47/62* (2017.01)
  *A61P 1/00* (2006.01)
  *A61P 31/04* (2006.01)
  *C08G 69/40* (2006.01)
  *G01N 33/569* (2006.01)

(52) U.S. Cl.
  CPC .............. *A61P 31/04* (2018.01); *C08G 69/40* (2013.01); *G01N 33/56922* (2013.01)

(56) References Cited

FOREIGN PATENT DOCUMENTS

| | | | | |
|---|---|---|---|---|
| KR | 10-2016-0127360 | A | 11/2016 | |
| KR | 10-2017-0104024 | A | 9/2017 | |
| KR | 10-2018-0085689 | A | 7/2018 | |
| WO | 03/077873 | A2 | 9/2003 | |
| WO | 2007-023398 | A2 | 3/2007 | |
| WO | 2009-155665 | A1 | 12/2009 | |
| WO | WO-2018135882 | A1 * | 7/2018 | ............. A61K 41/00 |

OTHER PUBLICATIONS

Parente, F. et al., "Treatment of Helicobacter Pylori Infection Using a Novel Antiadhesion Compound (3'sialyllactose sodium salt). A Double blind, Placebo-Controlled Clinical Study", Helicobacter. 2003, vol. 8, No. 4, pp. 252-256.

Sahu, K. et al., "Topical photodynamic treatment with poly-L-lysine-chlorin p6 conjugate improves wound healing by reducing hyperinflammatory response in Pseudomonas aeruginosa-infected wounds of mice", Lasers Med Sci, 2013, vol. 28, No. 2, pp. 465-471.

Dolores G. Evans et al., "N-Acetylneuraminyllactose-Binding Fibrillar Hemagglutinin of Campylobacter pylori: a Putative Colonization Factor Antigen", Infection and Immunity, 1988, vol. 56, No. 11, pp. 2896-2906.

Simon, C. et al., "In vitro studies of chlorin e6-assisted photodynamic inactivation of Helicobacter pylori", Proceedings of SPIE, 2014, vol. 8931, Article No. 893115.

Koji Ogasawara et al., "Eradication of H. pylori by PACT=Aiming to eradicate H. pylori by LED irradiation=", Optical Alliance, 2015, vol. 26, No. 3, pp. 9-10.

* cited by examiner

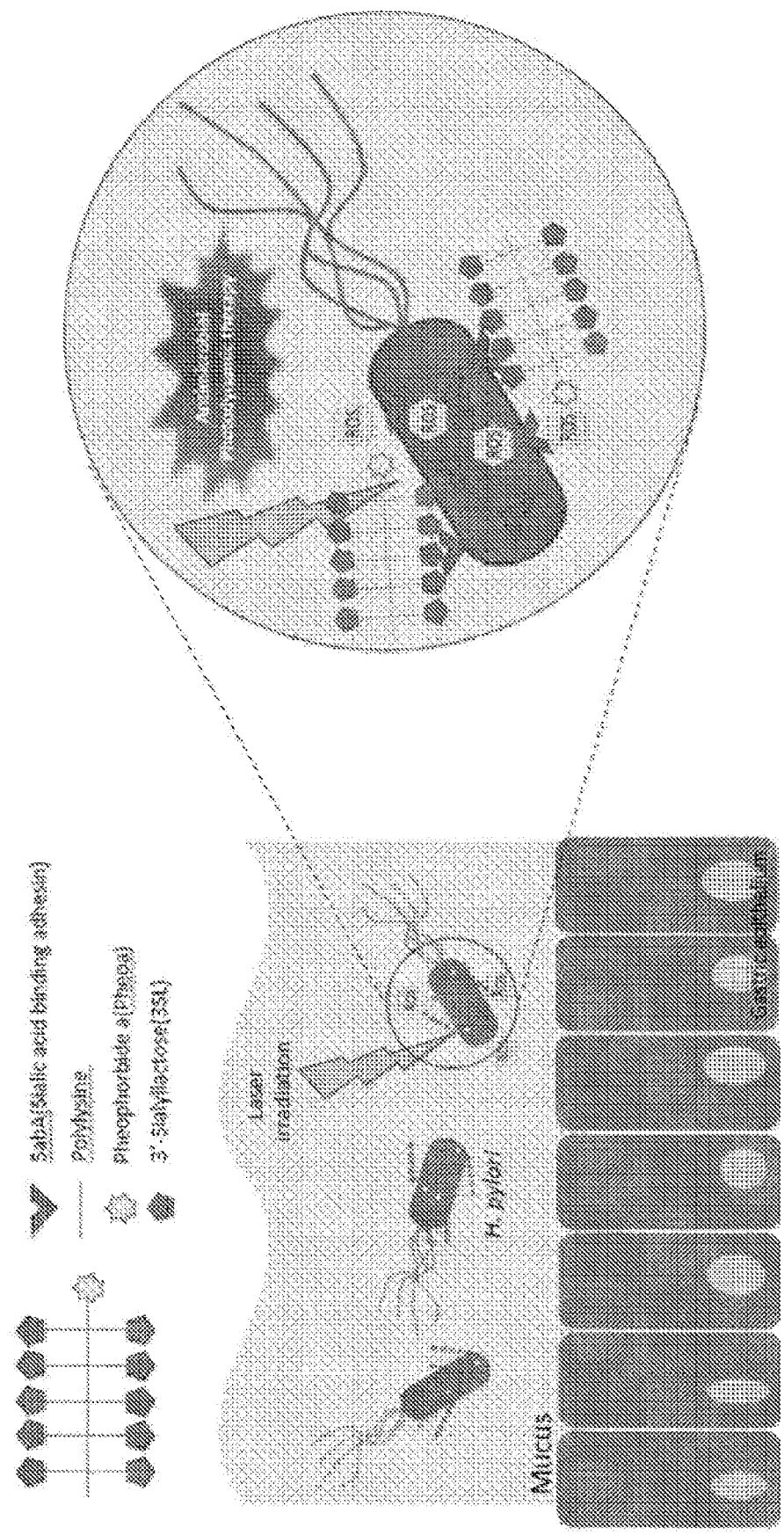
[FIG. 1]

[FIG. 2]
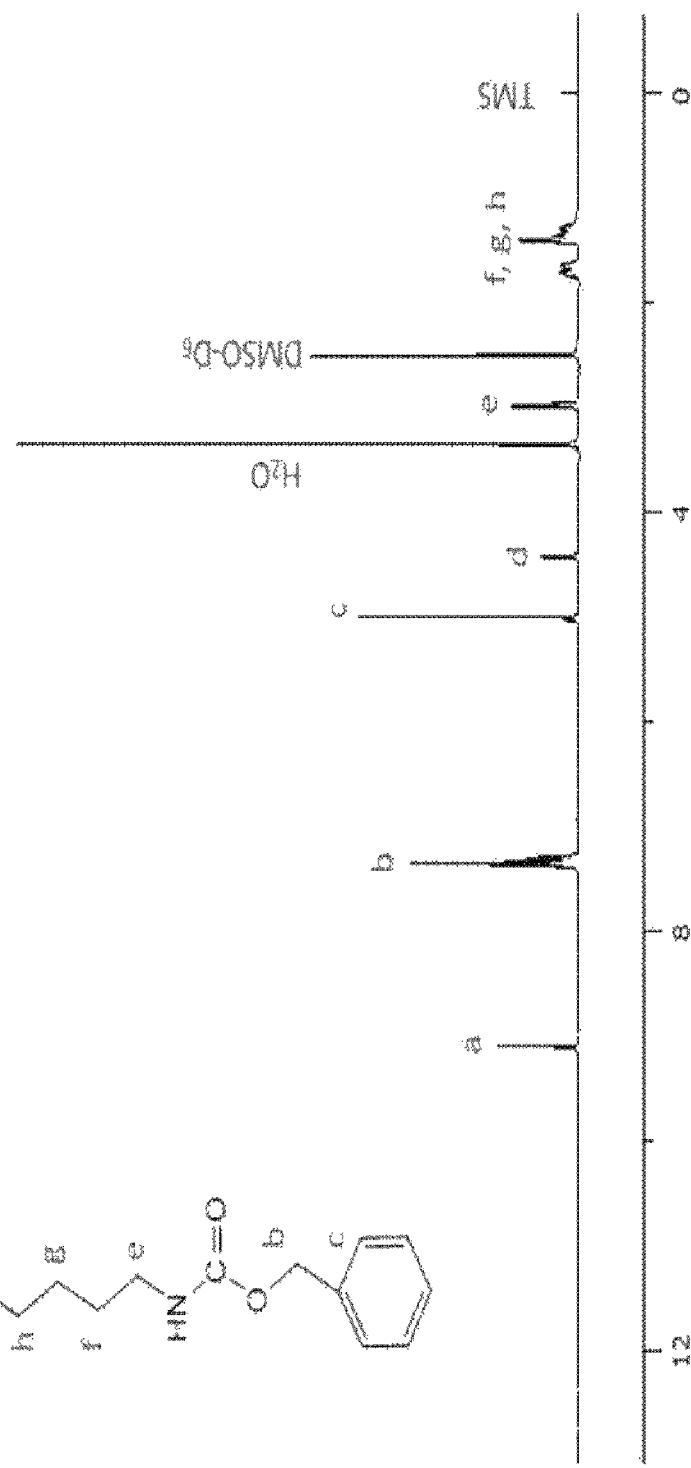

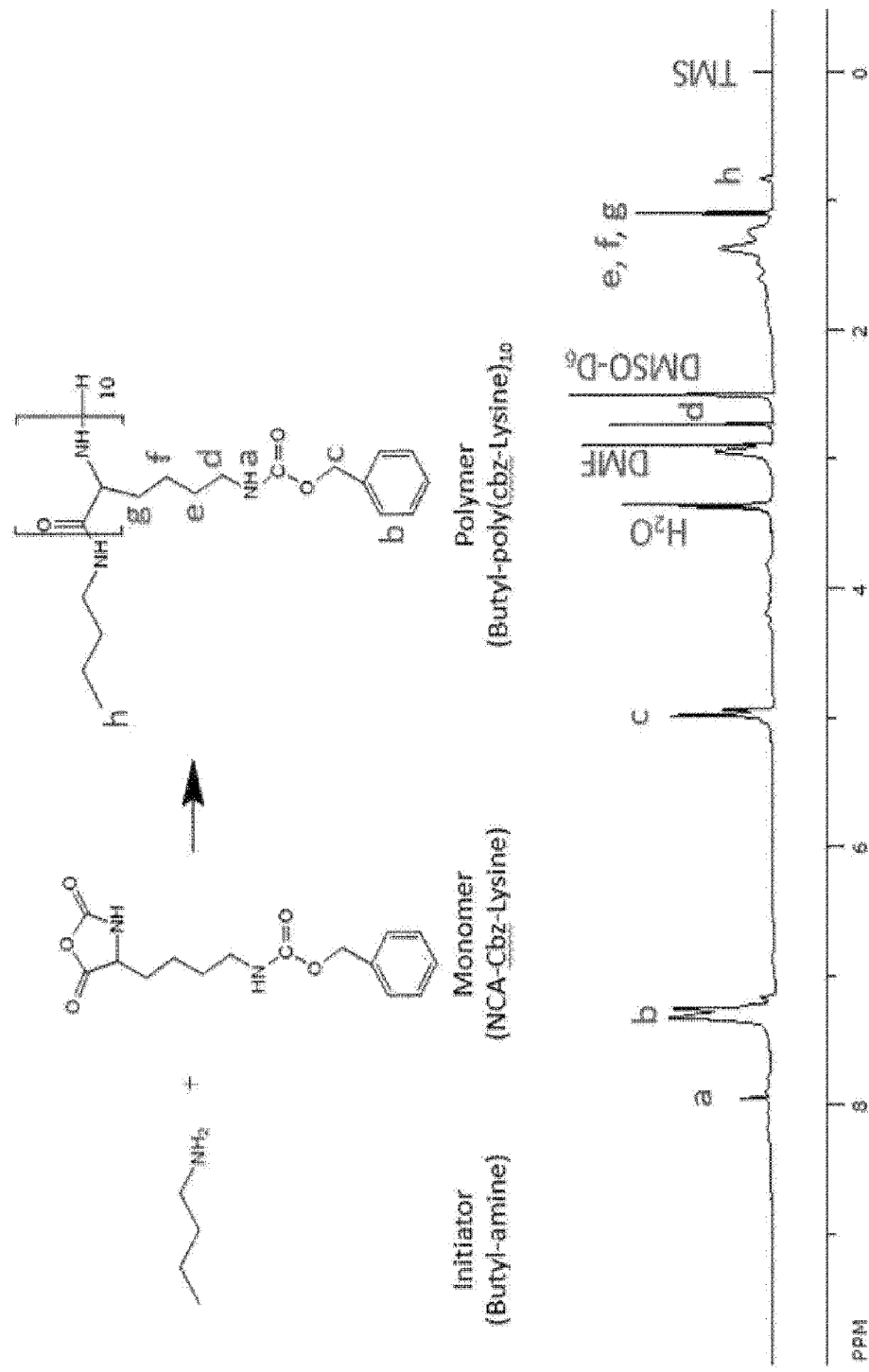
[FIG. 3]

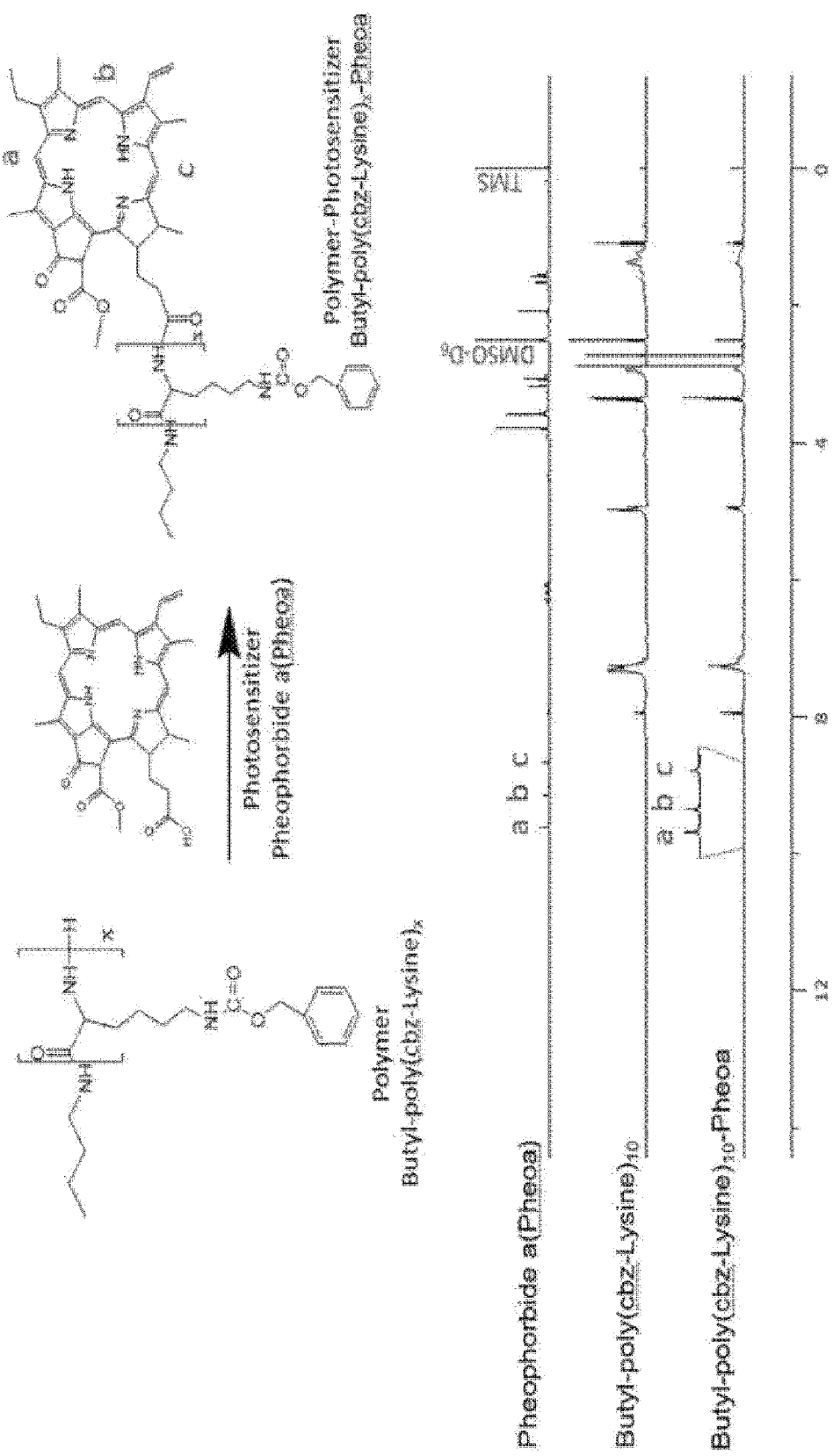
[FIG. 4]

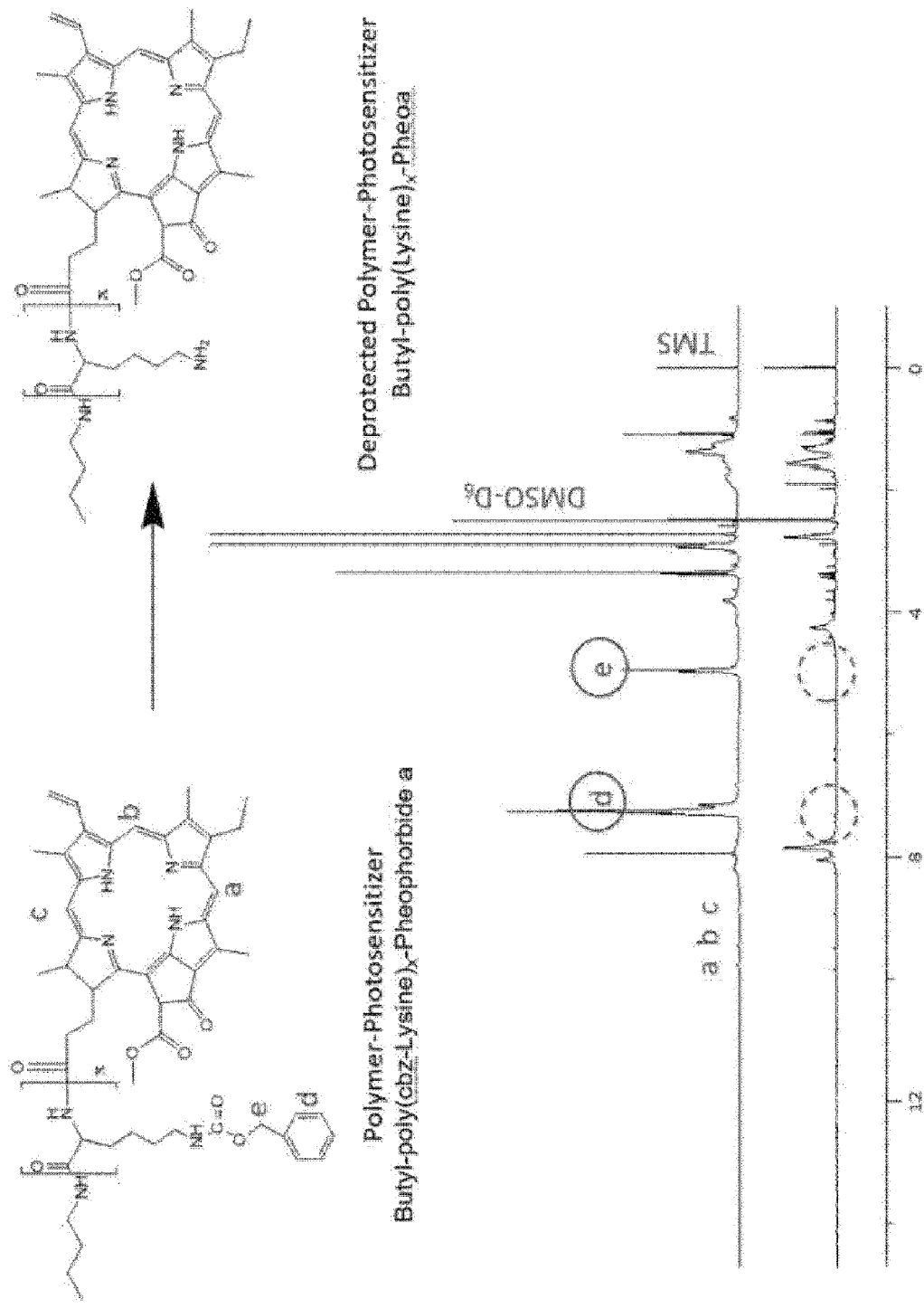
[FIG. 5]

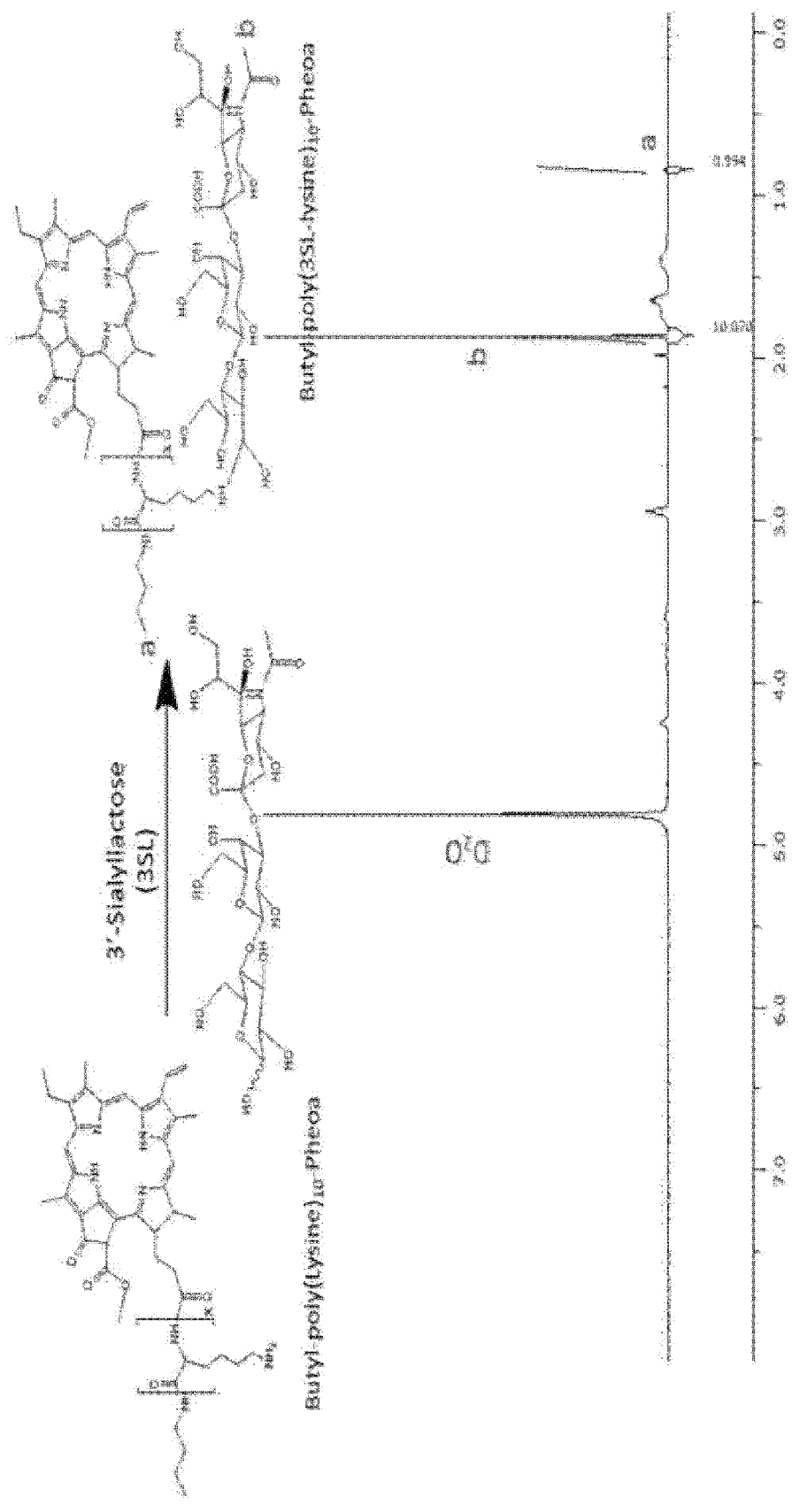
[FIG. 6]

[FIG. 7]
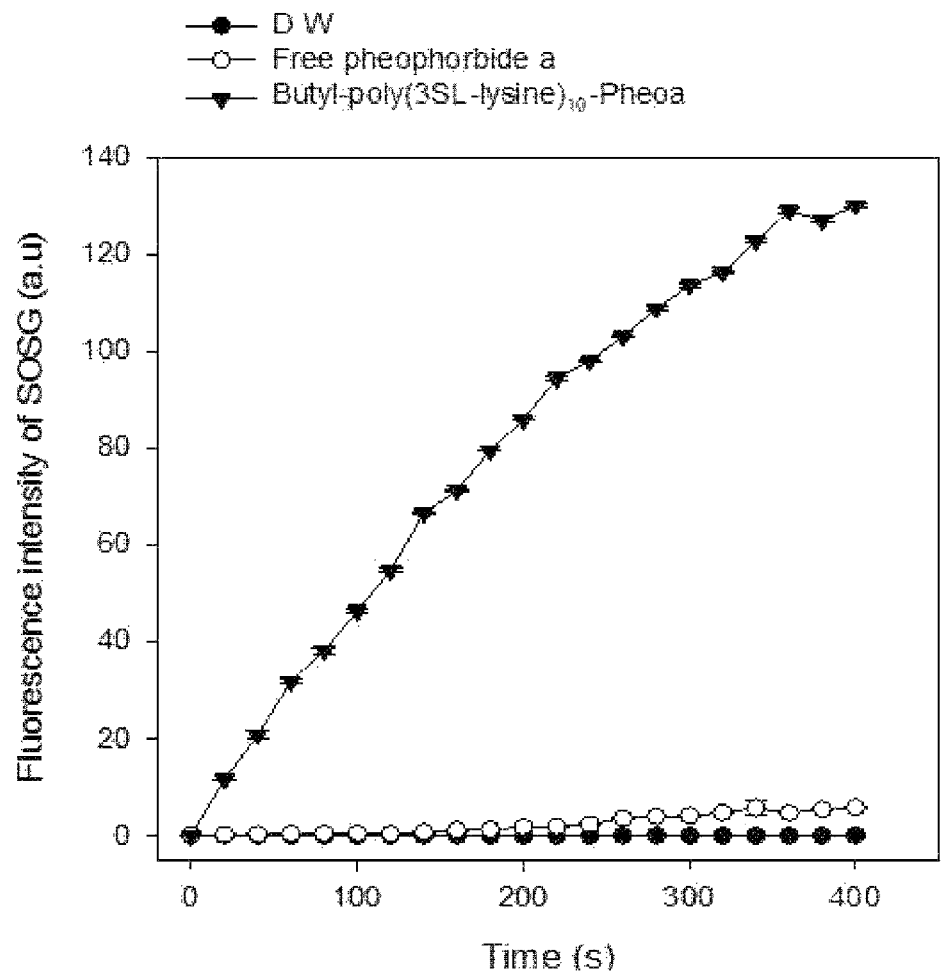

[FIG. 8]
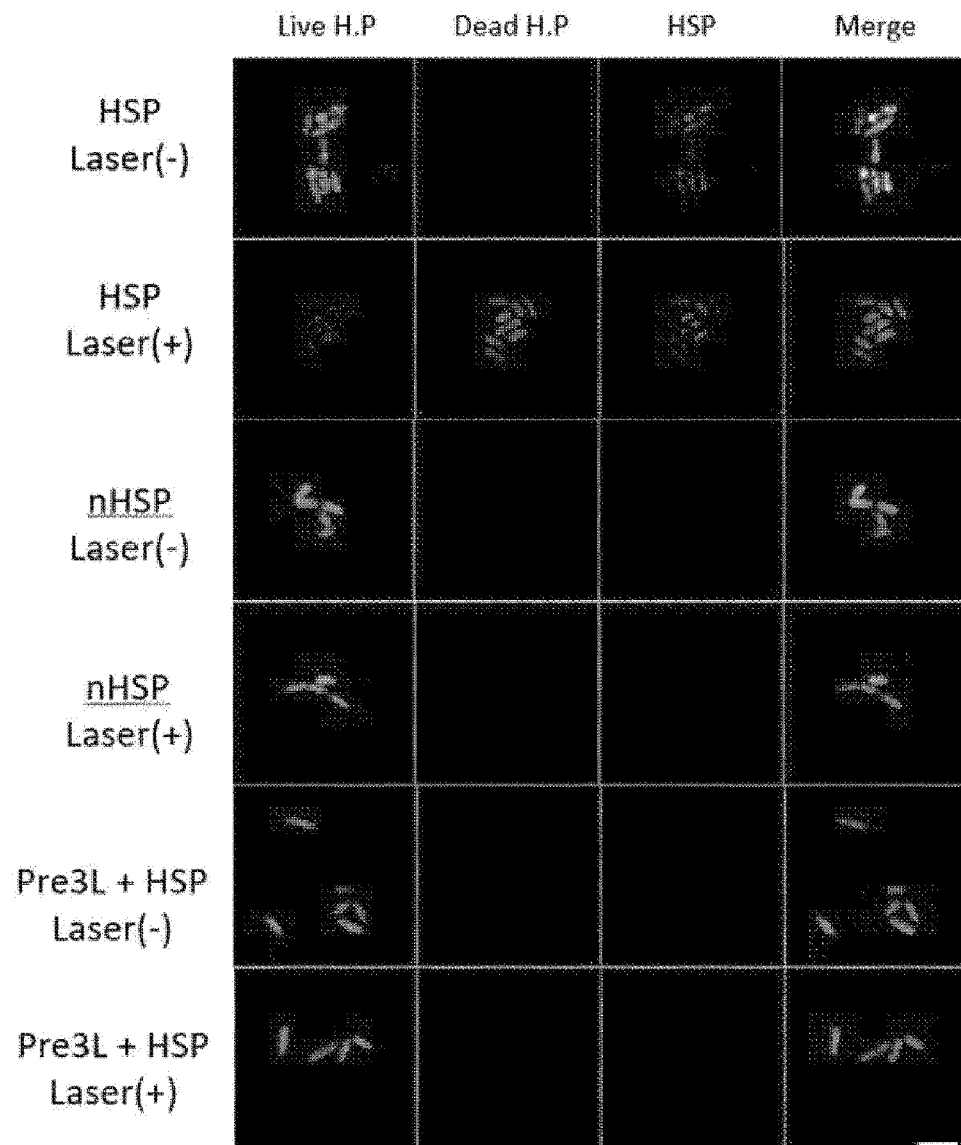

[FIG. 9]
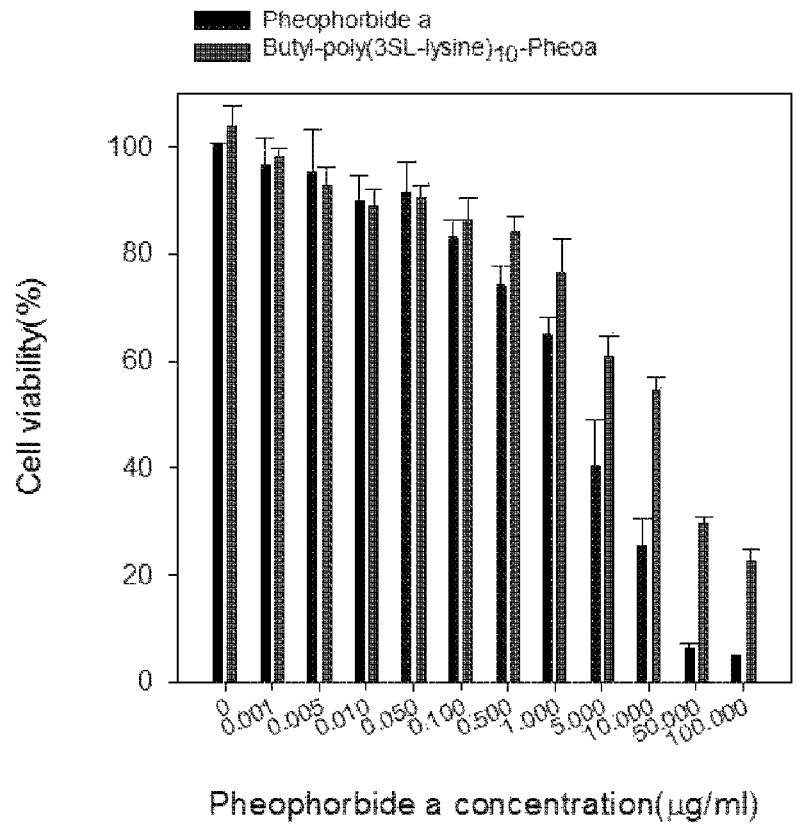
[FIG. 10]
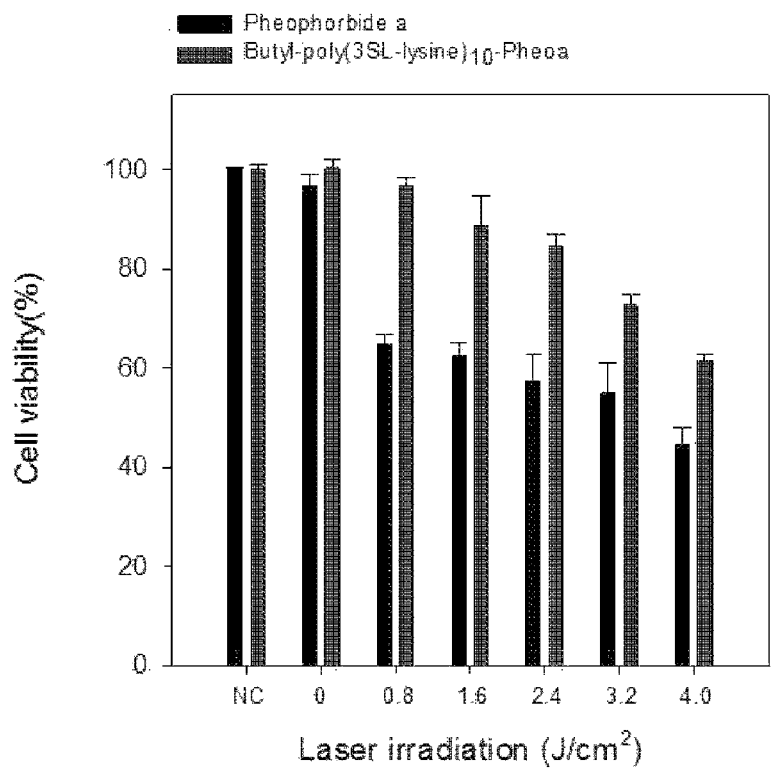

[FIG. 11]
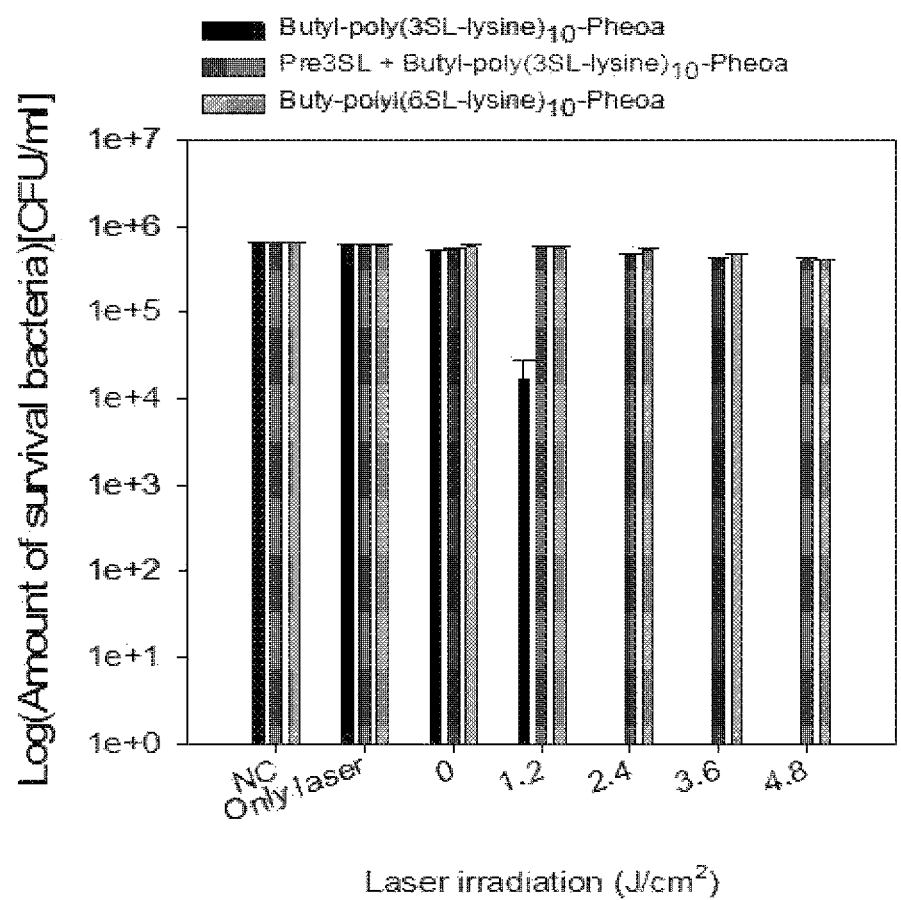

[FIG. 12]
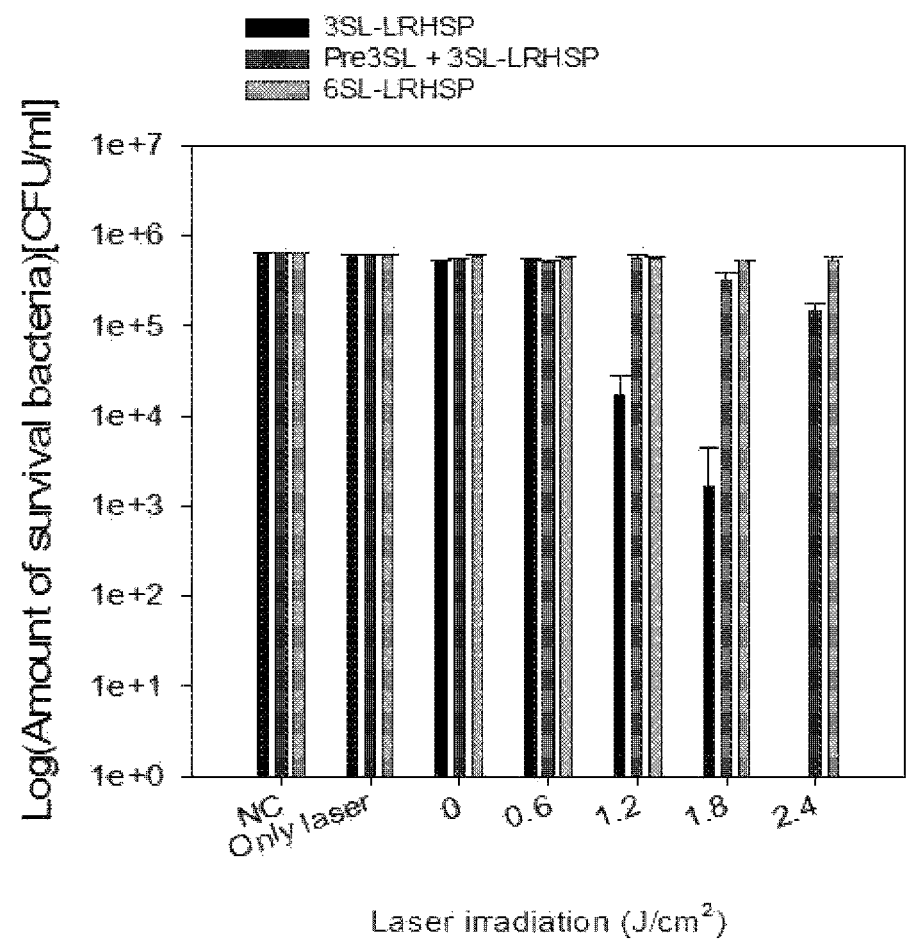

[FIG. 13]
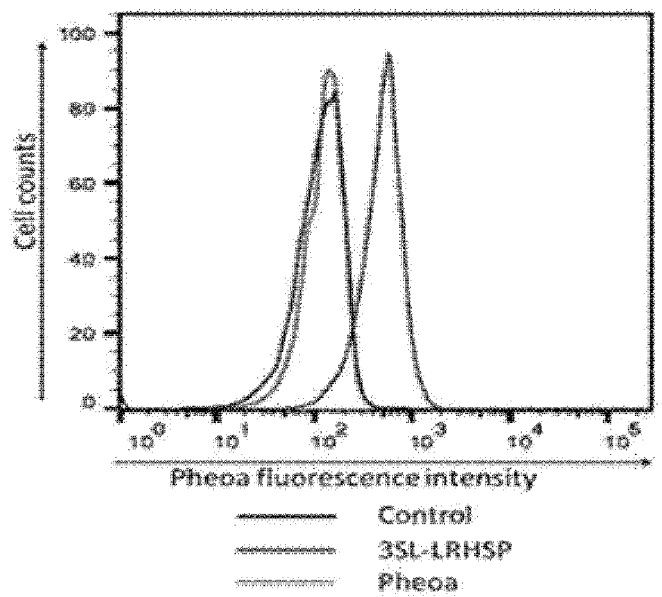
[FIG. 14]
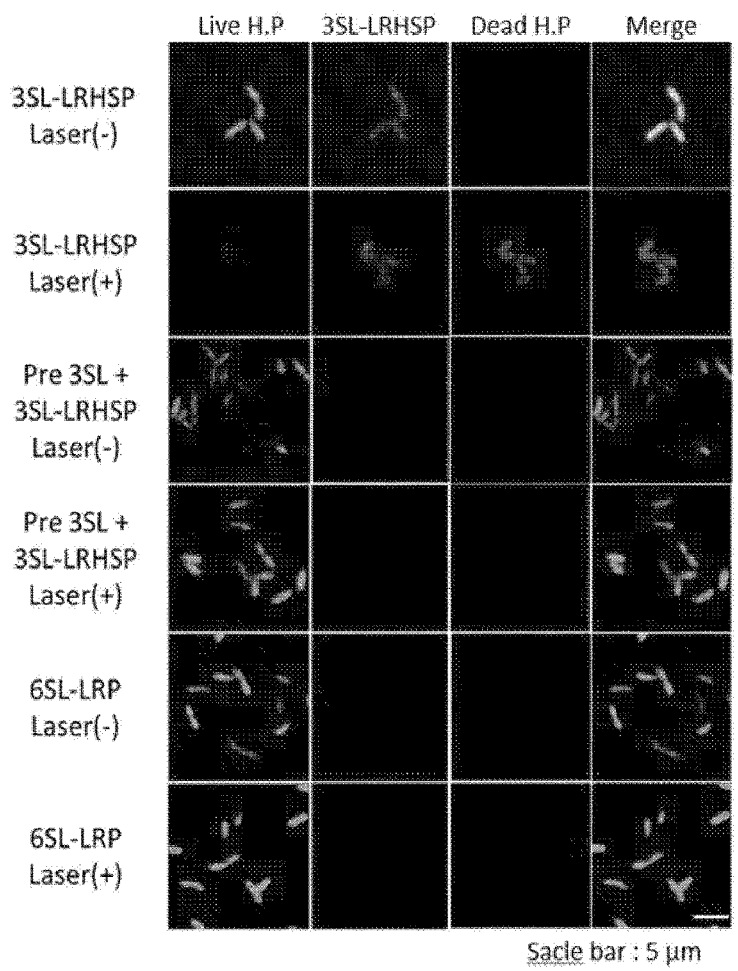

[FIG. 15]
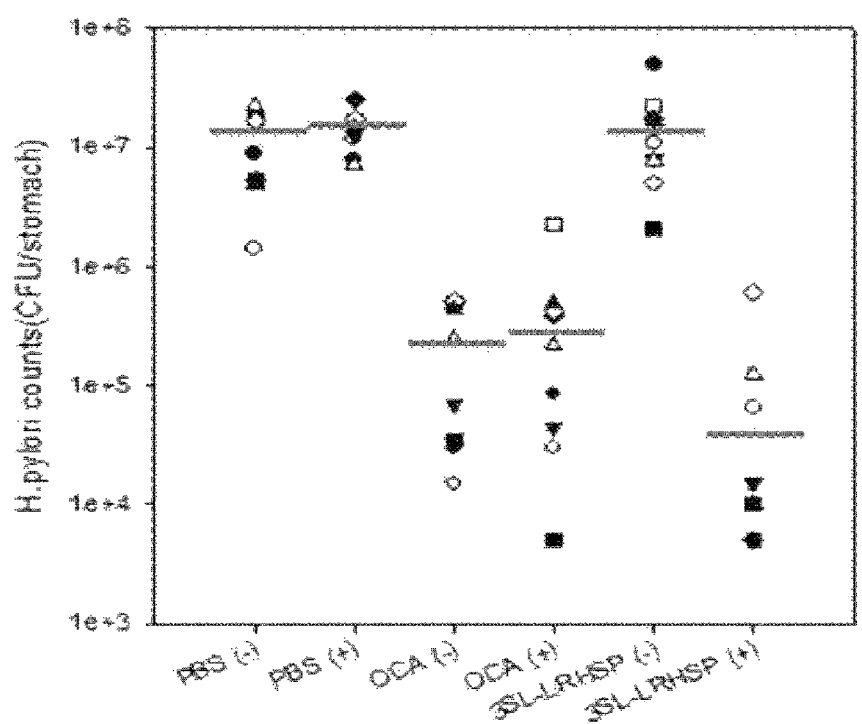

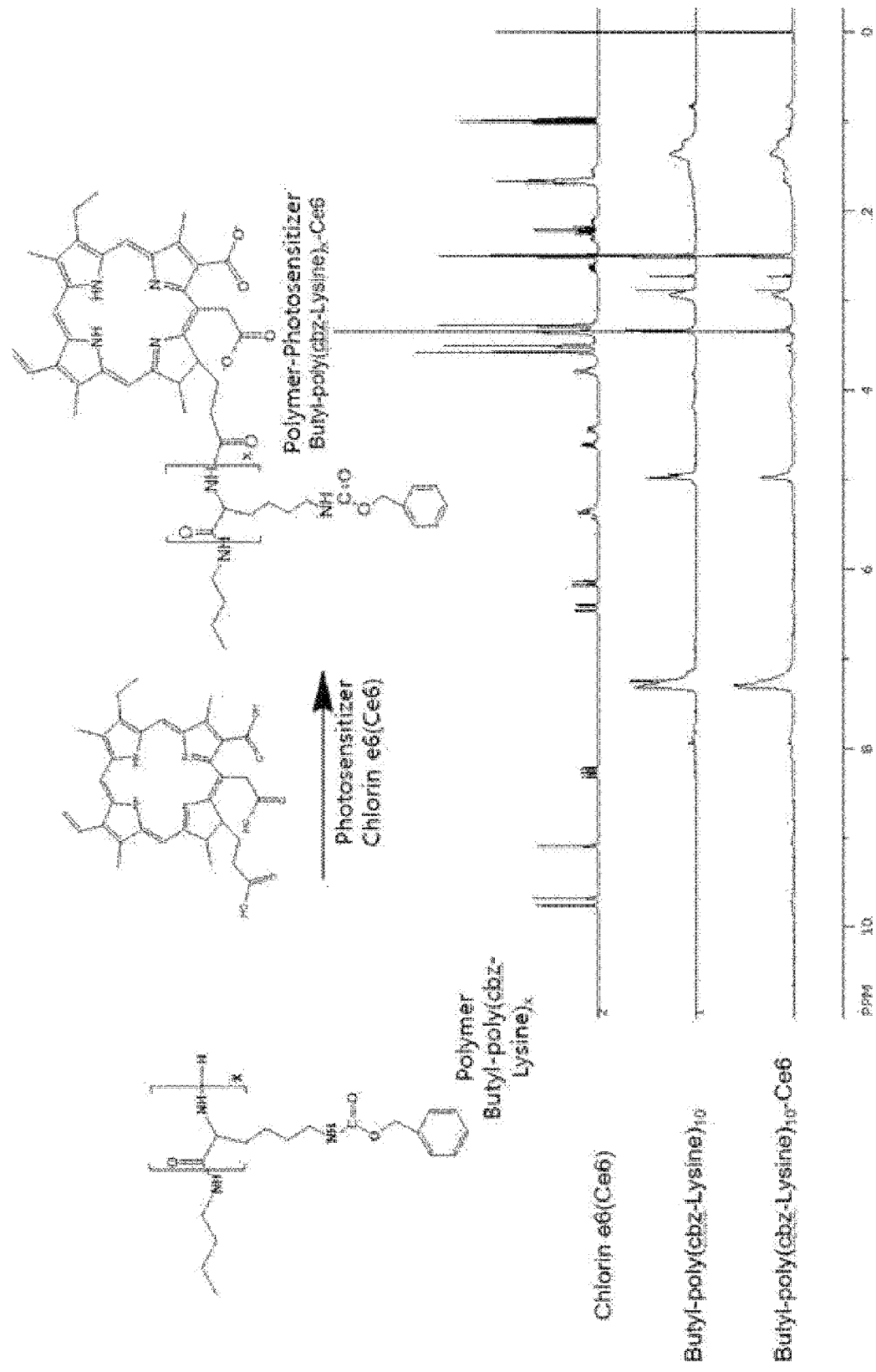
[FIG. 16]

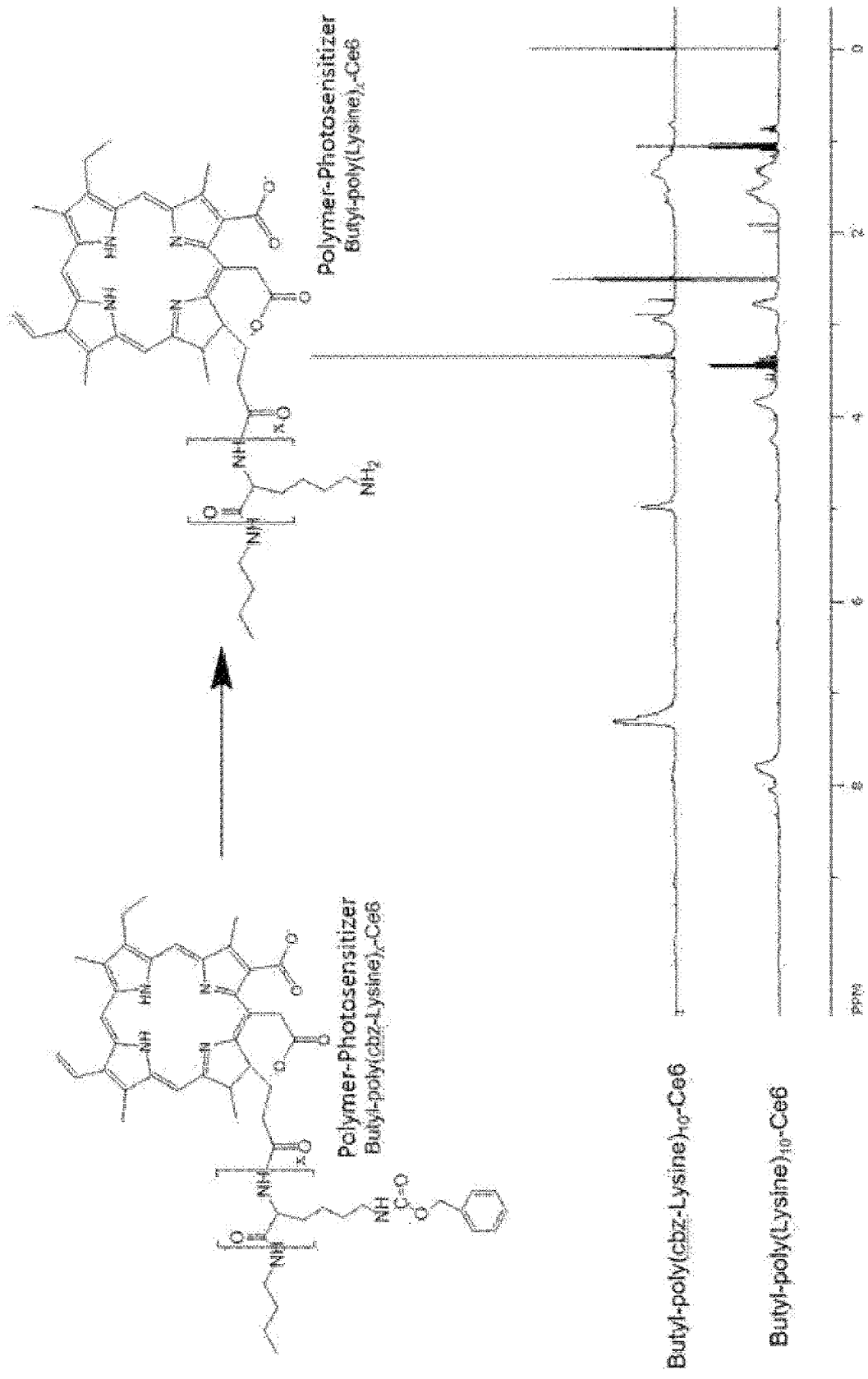
[FIG. 17]

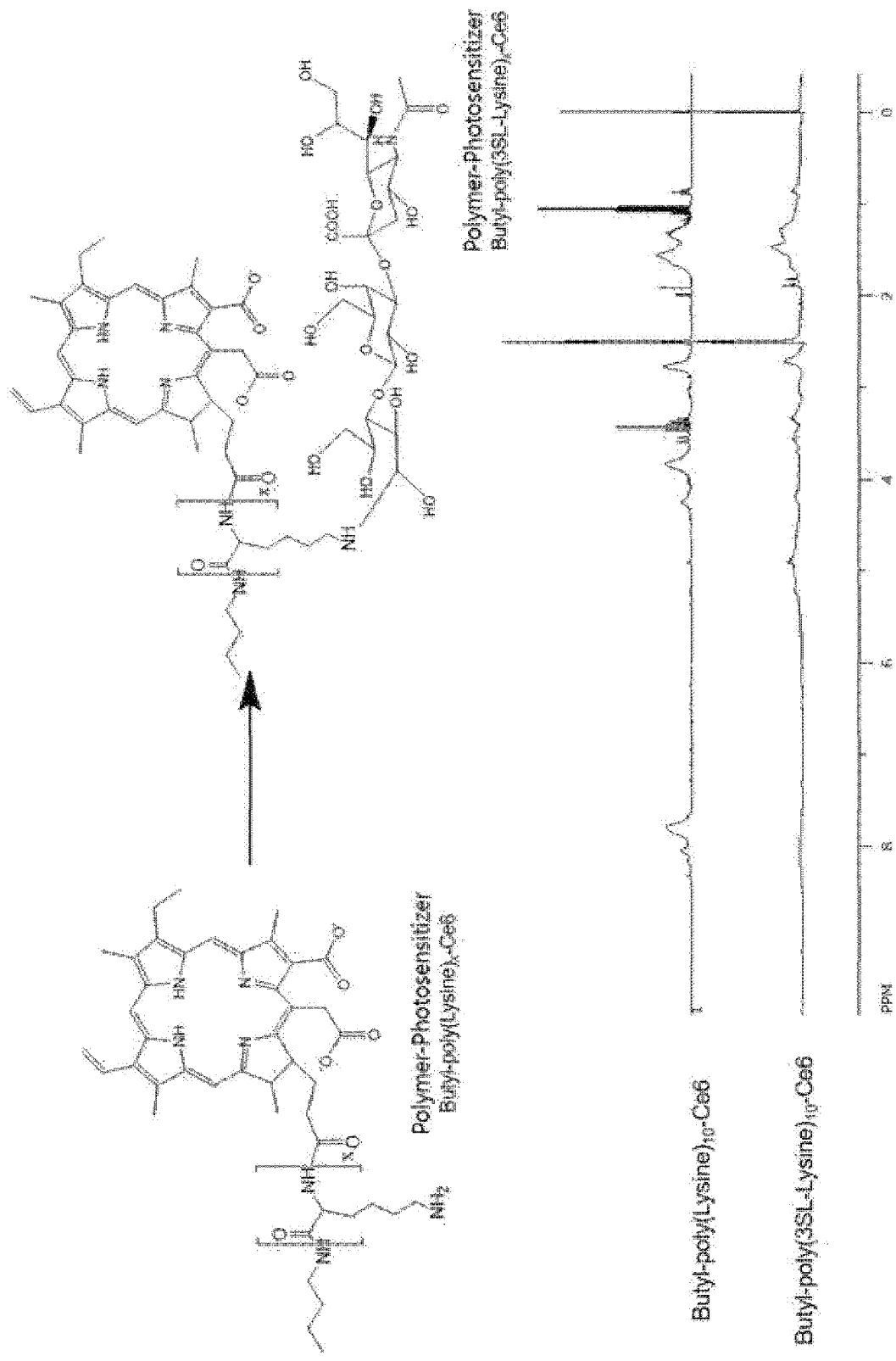
[FIG. 18]

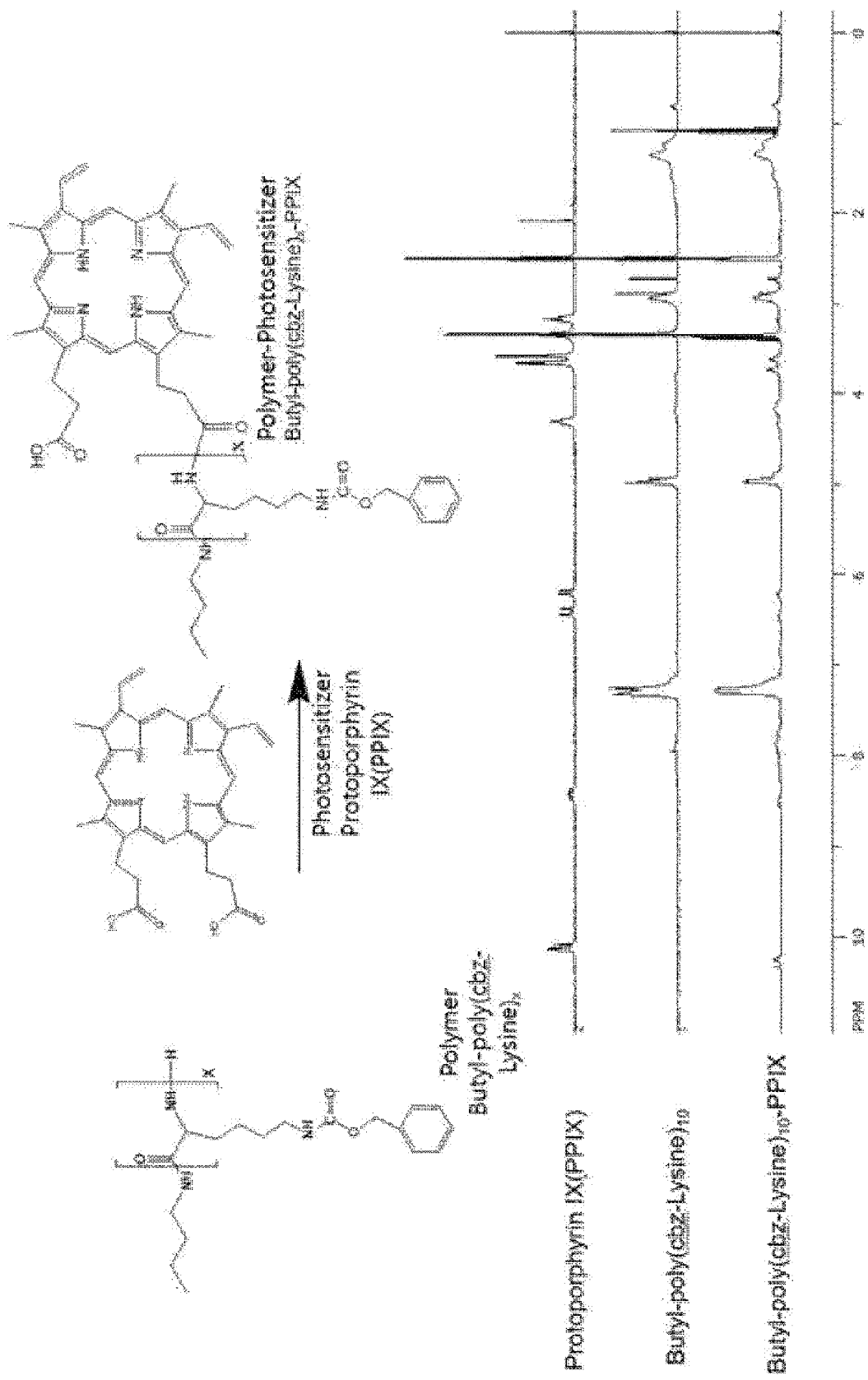
[FIG. 19]

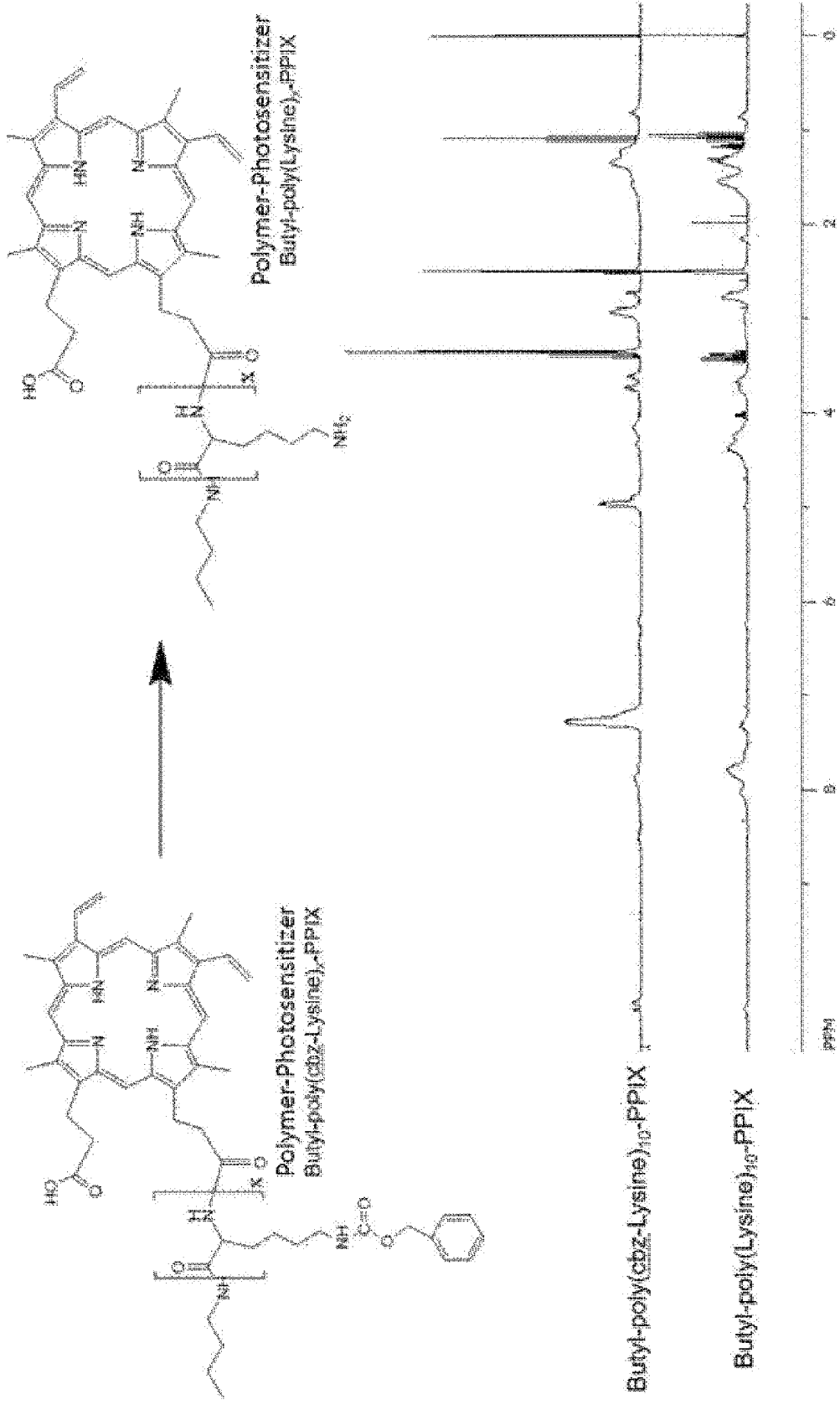
[FIG. 20]

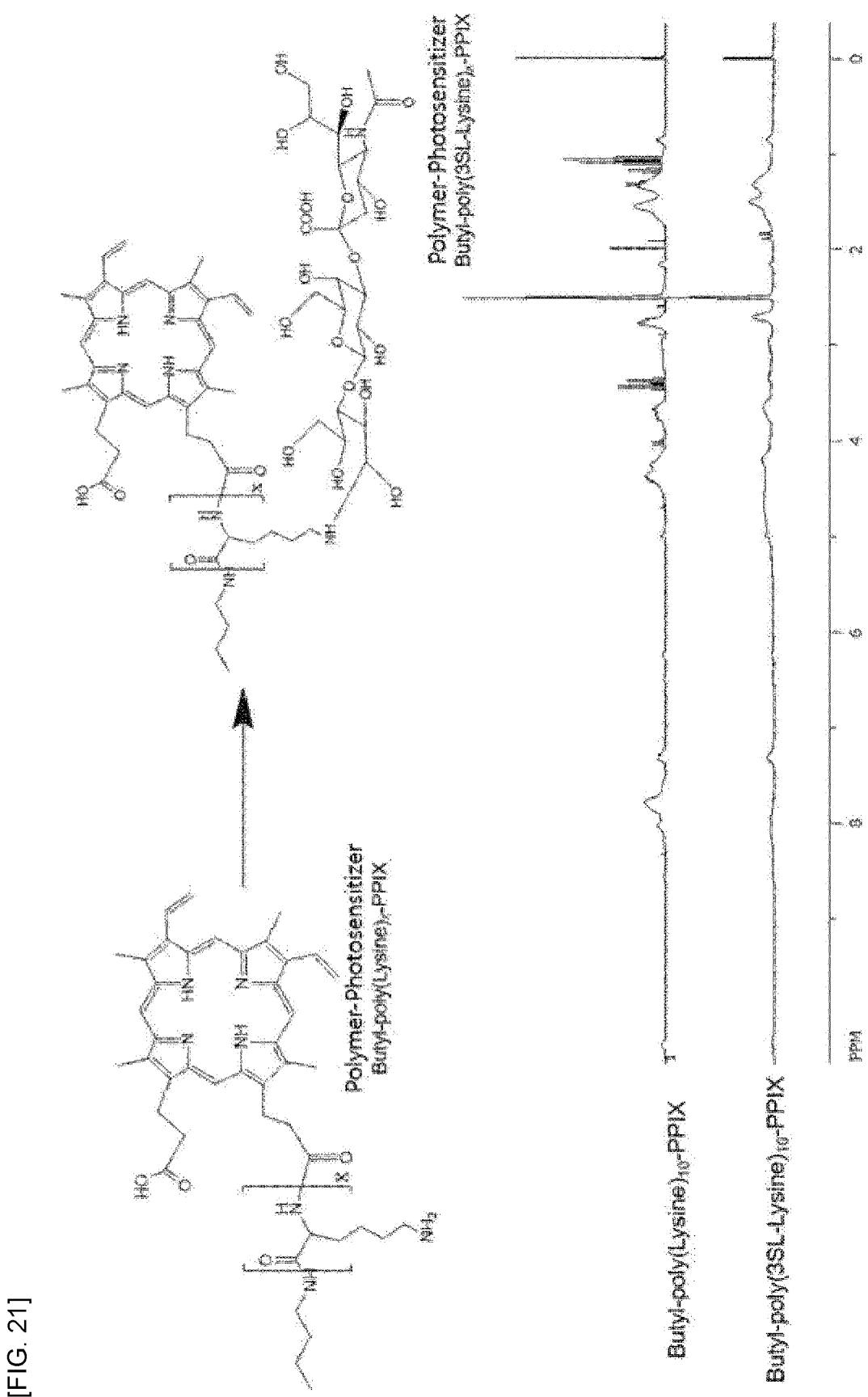
[FIG. 21]

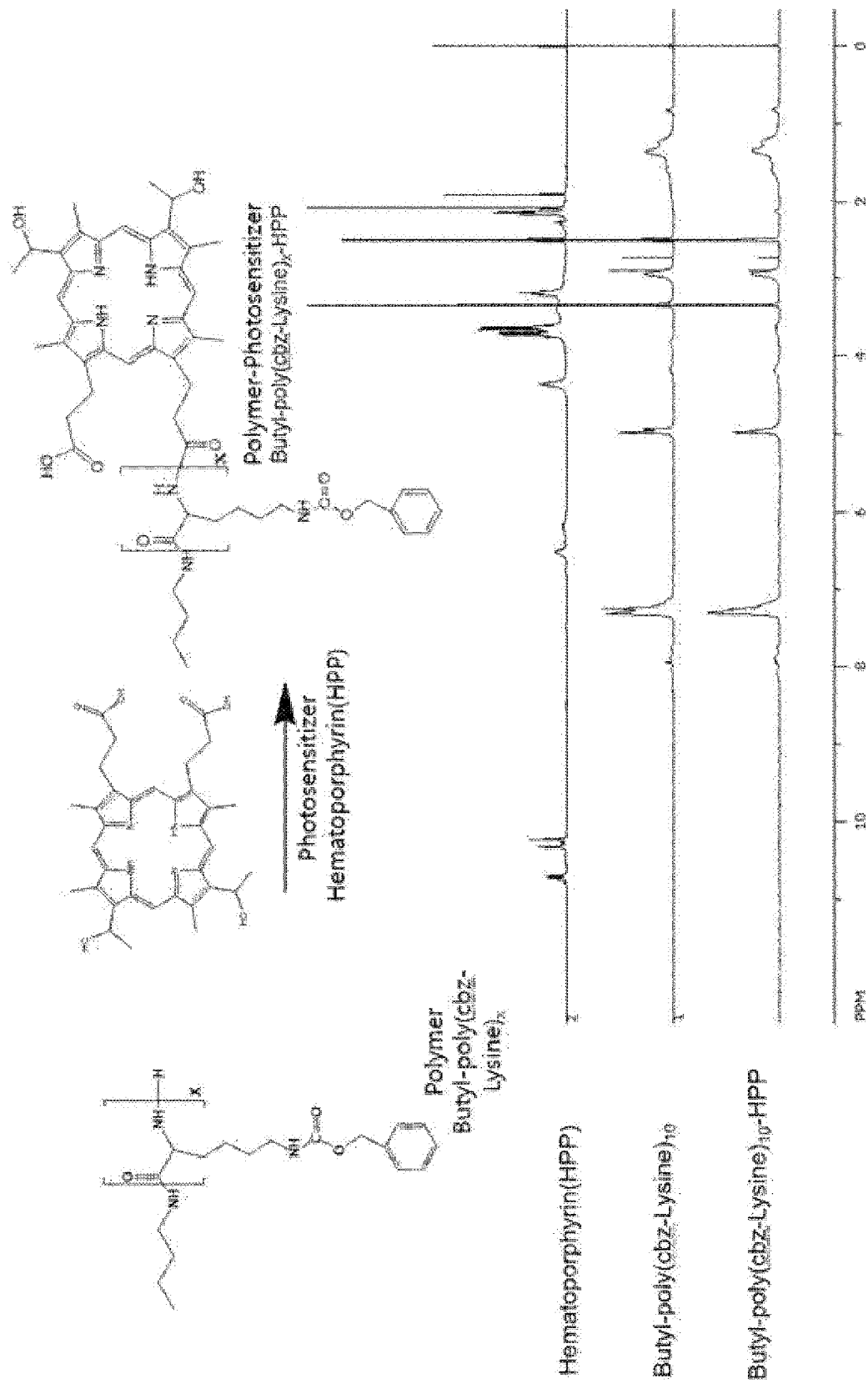
[FIG. 22]

[FIG. 23]
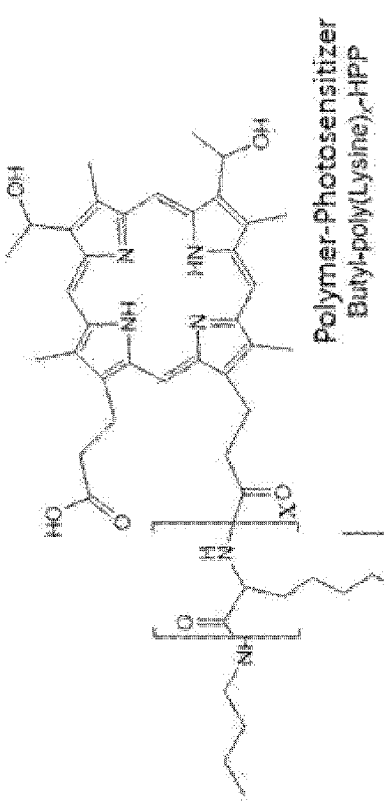
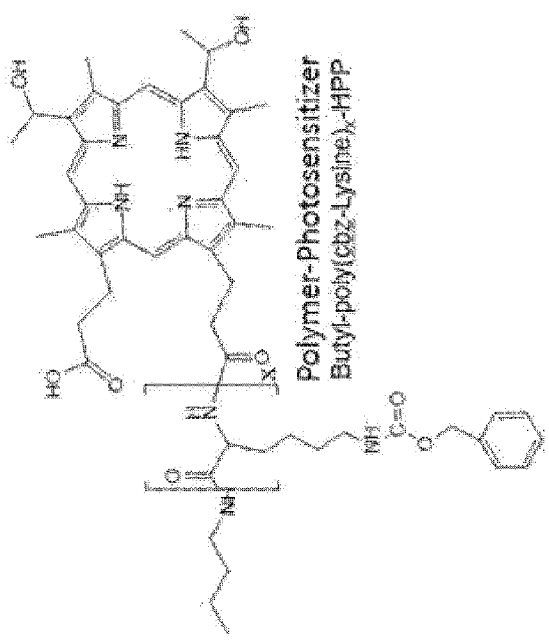
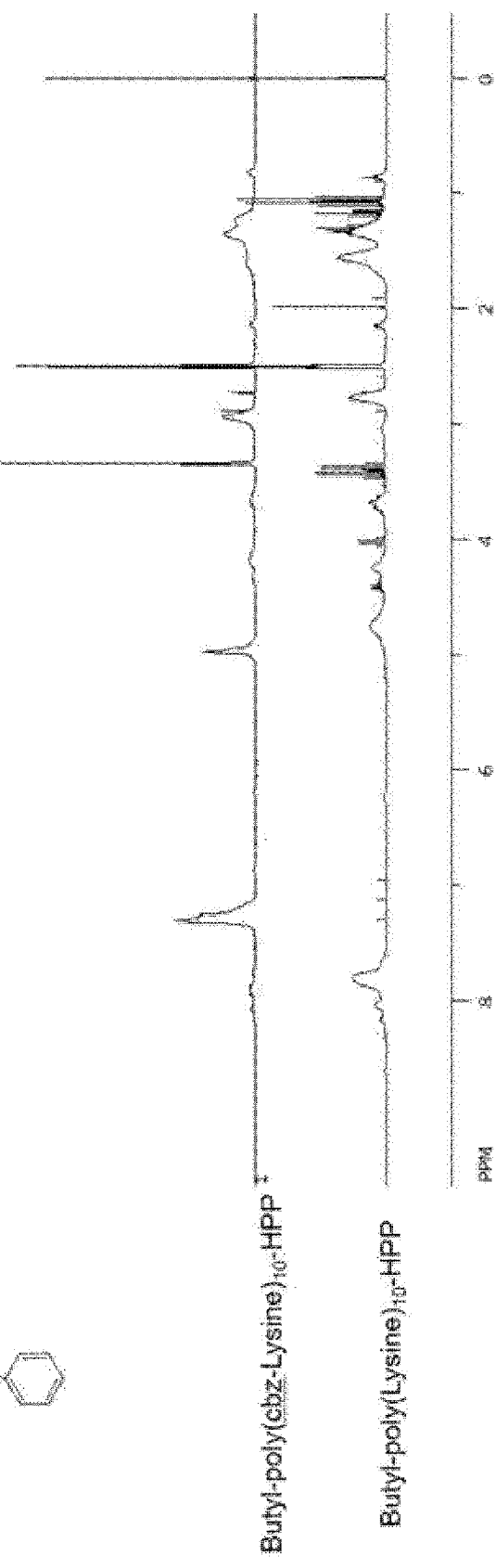

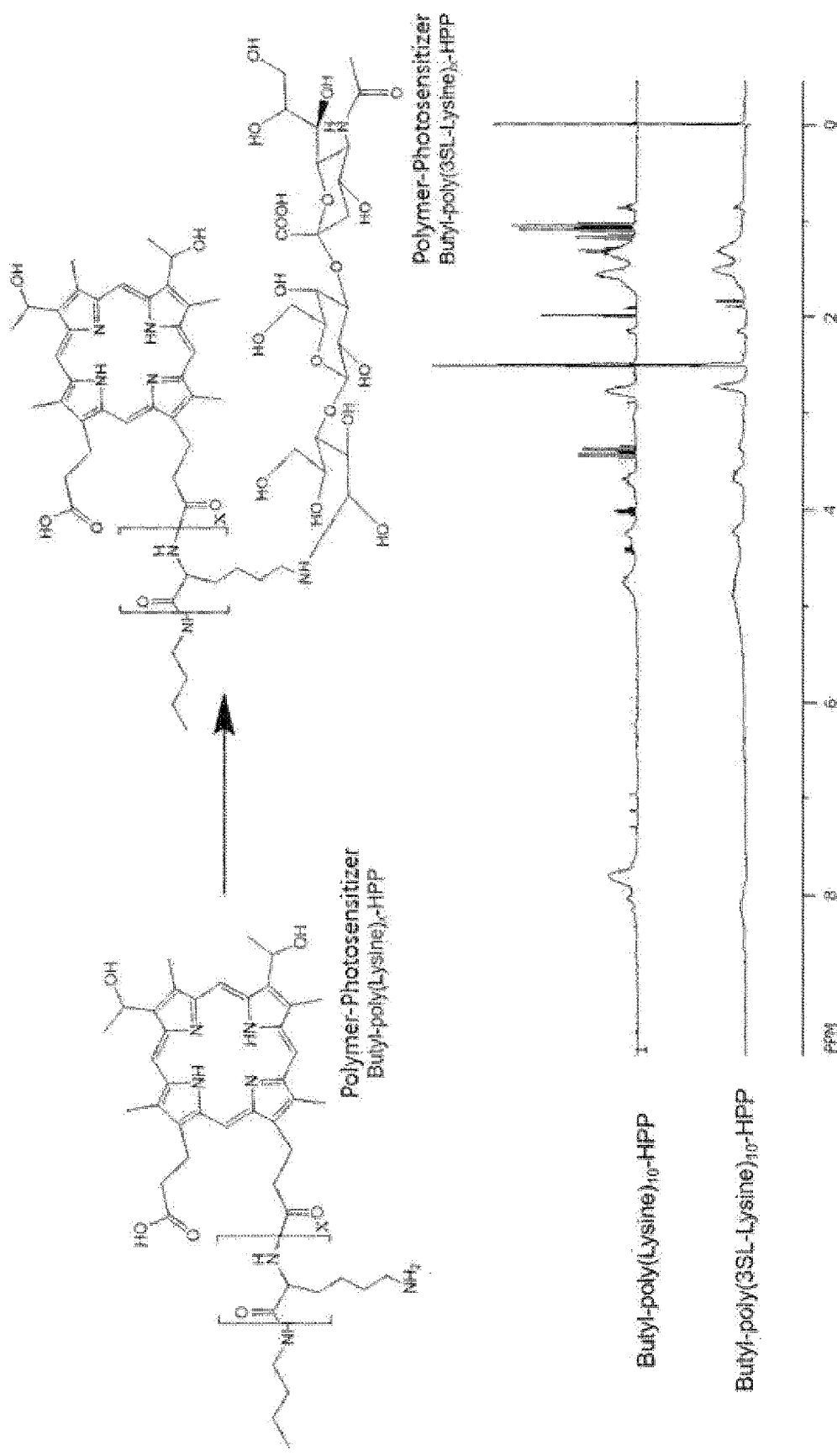
[FIG. 24]

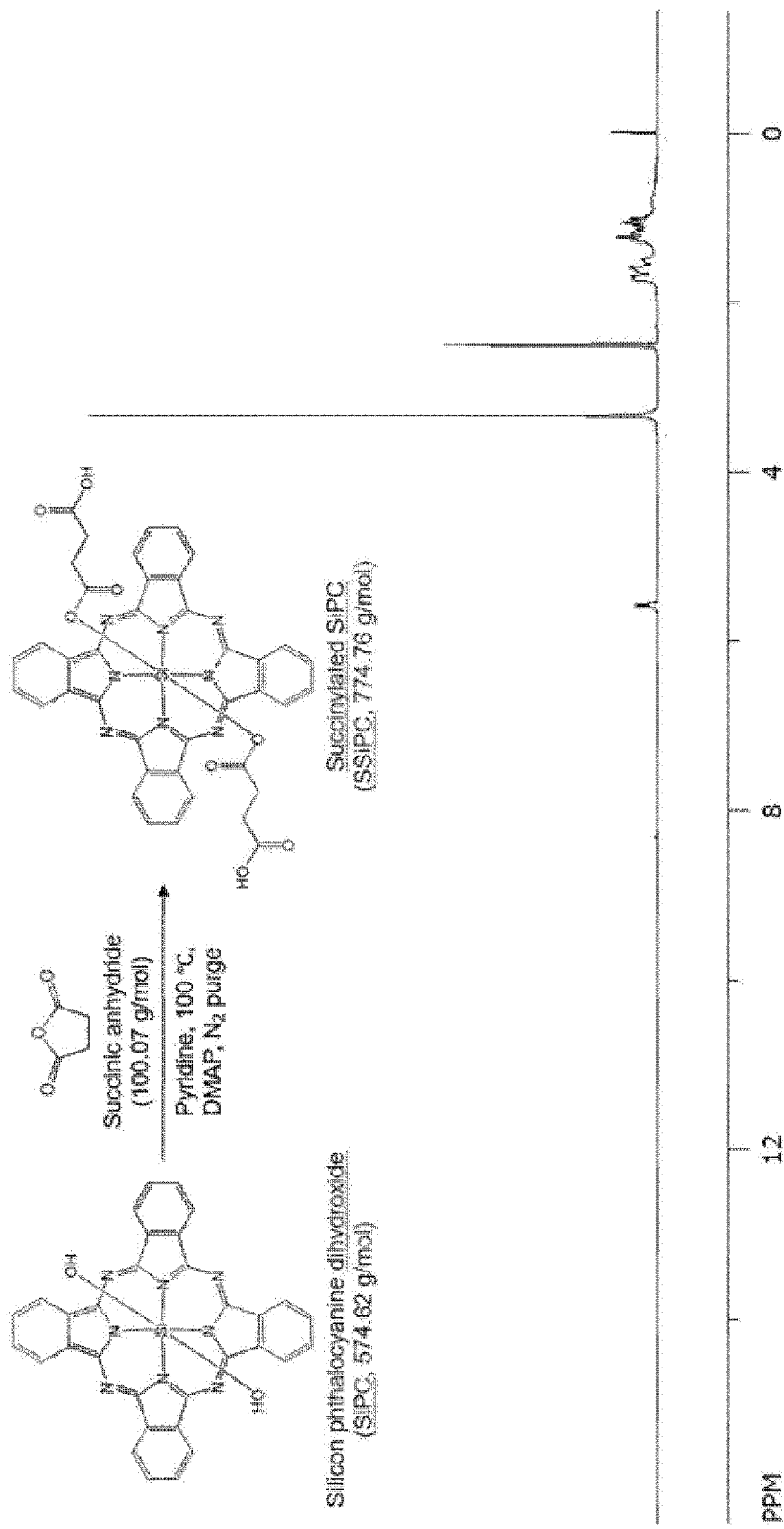
[FIG. 25]

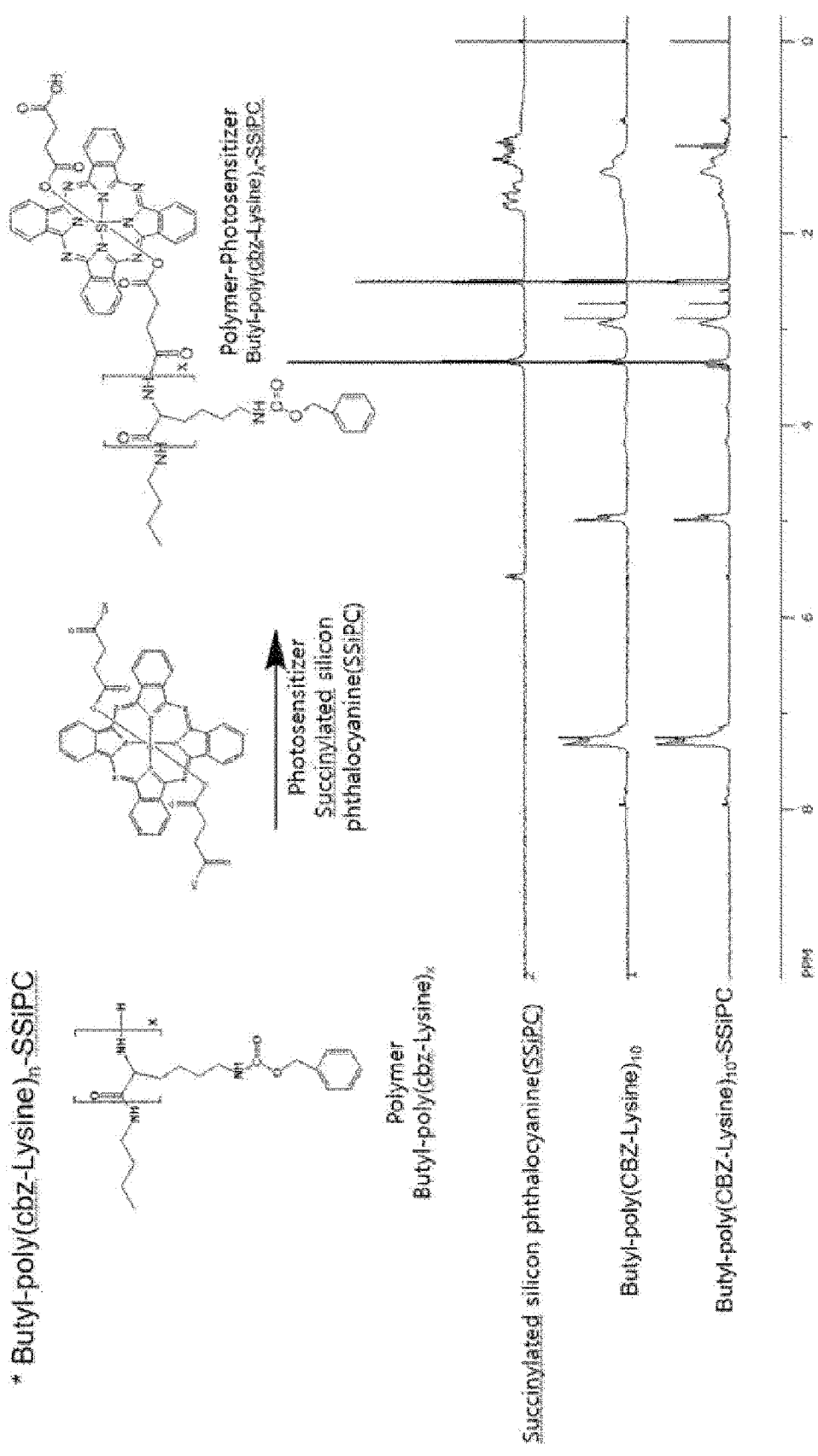
[FIG. 26]

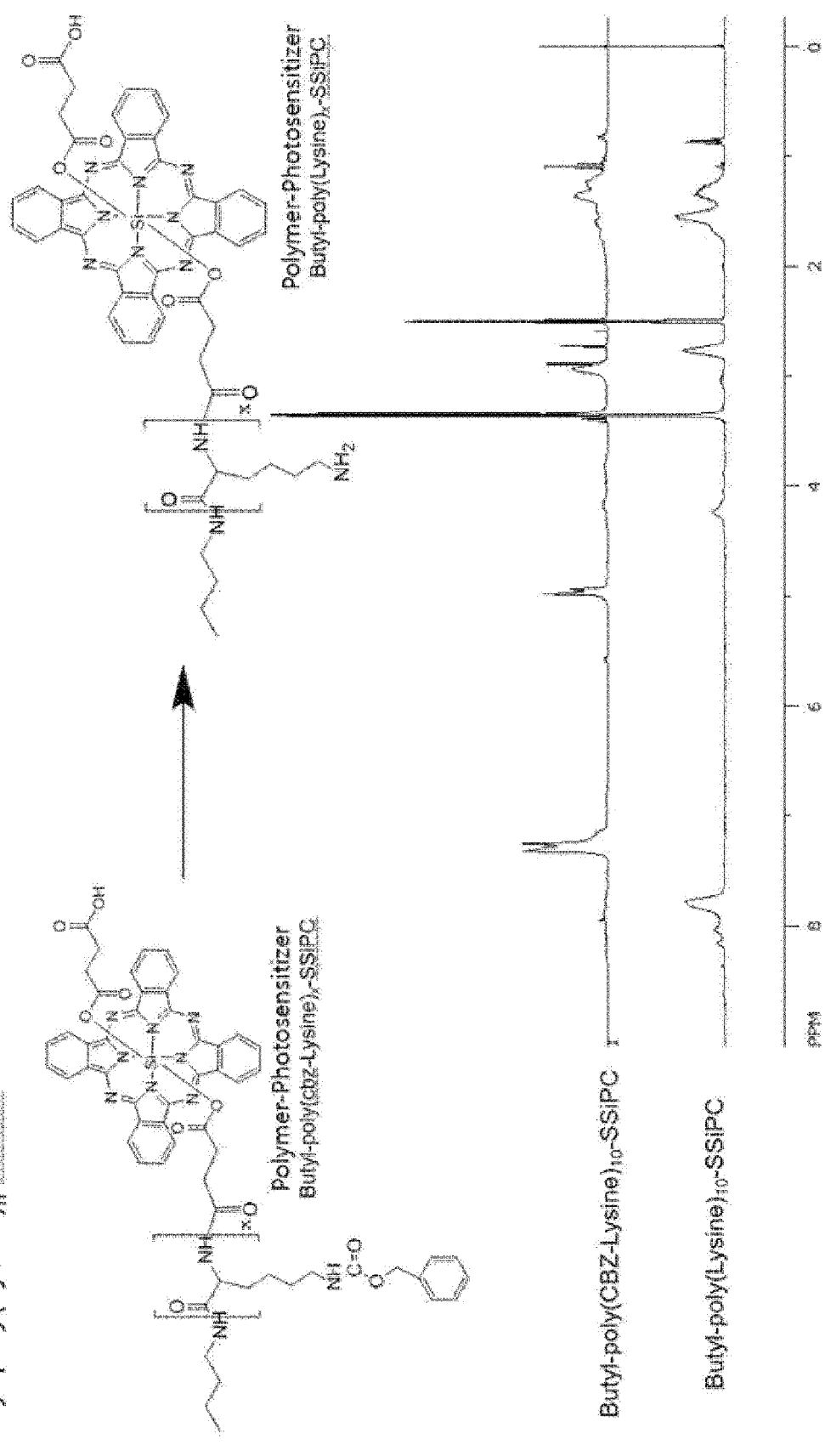
[FIG. 27]

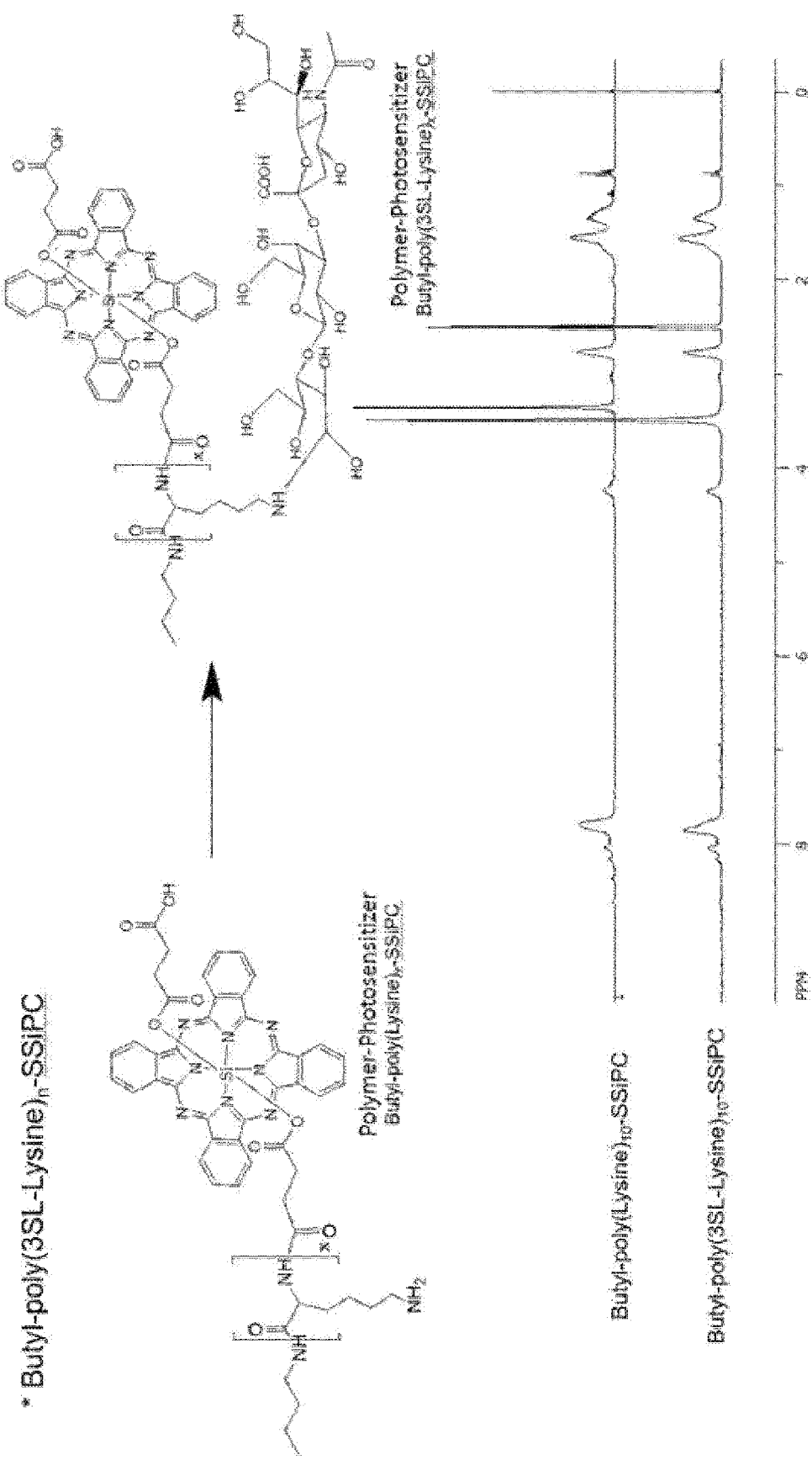
[FIG. 28]

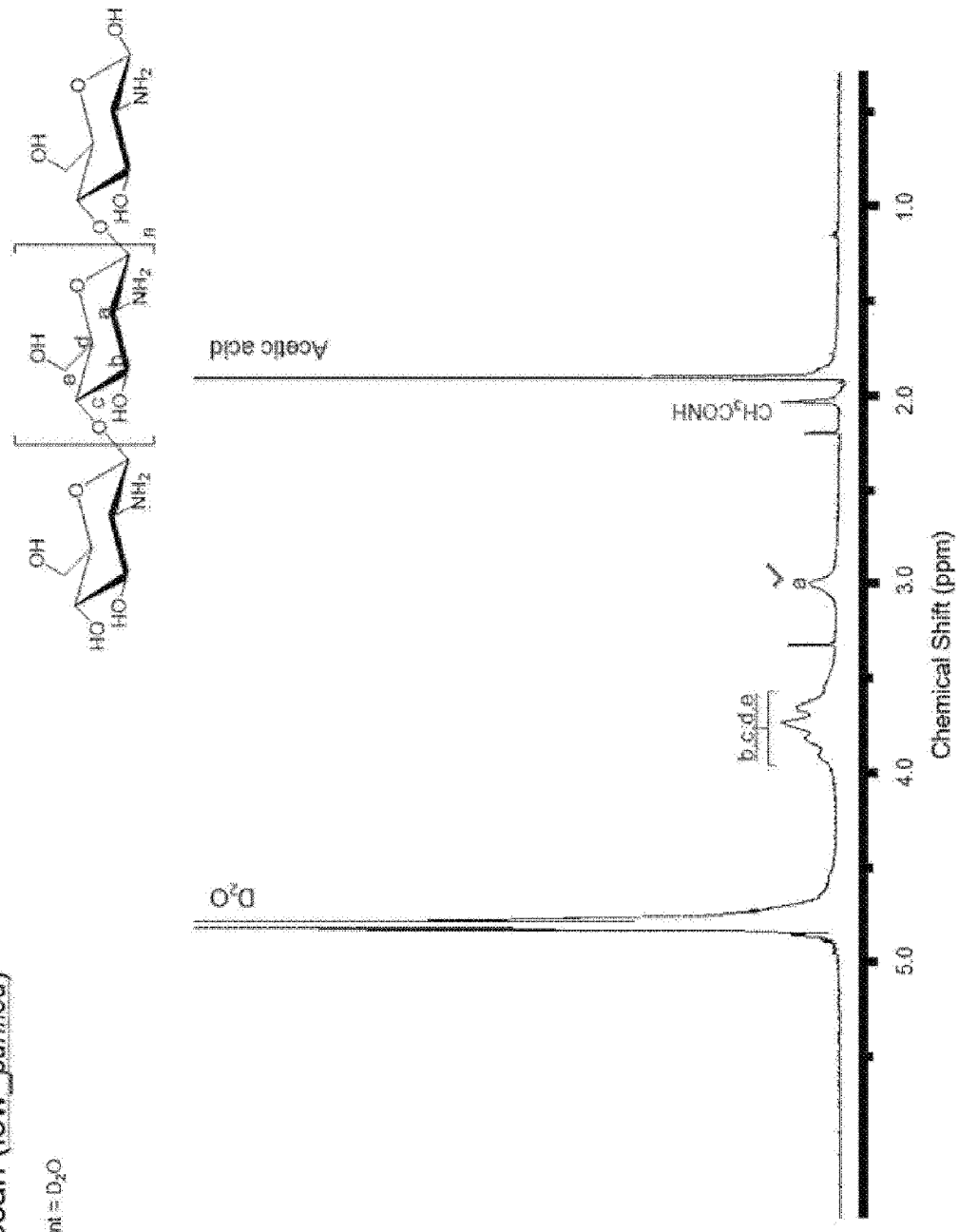
[FIG. 29]

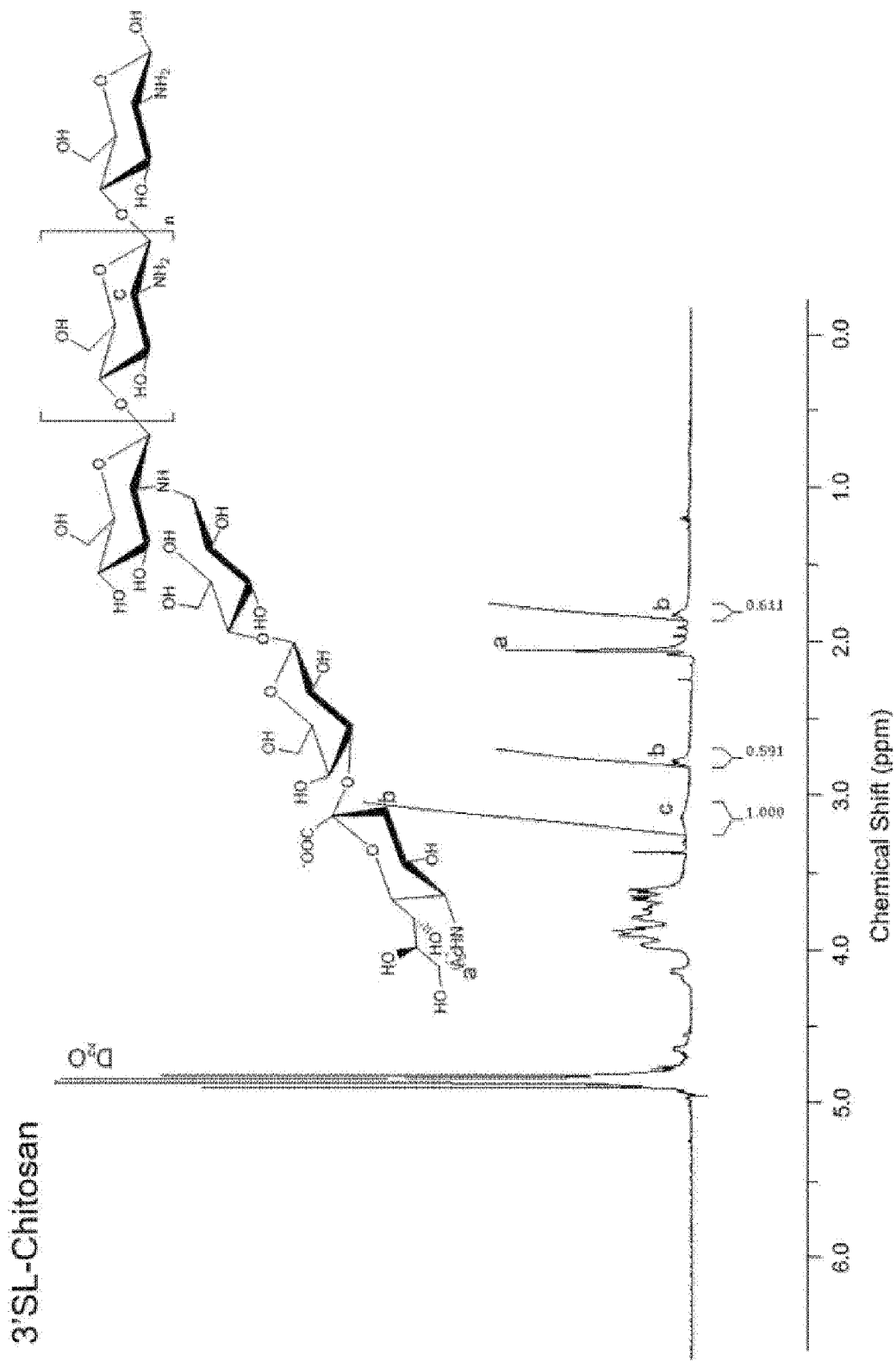
[FIG. 30]

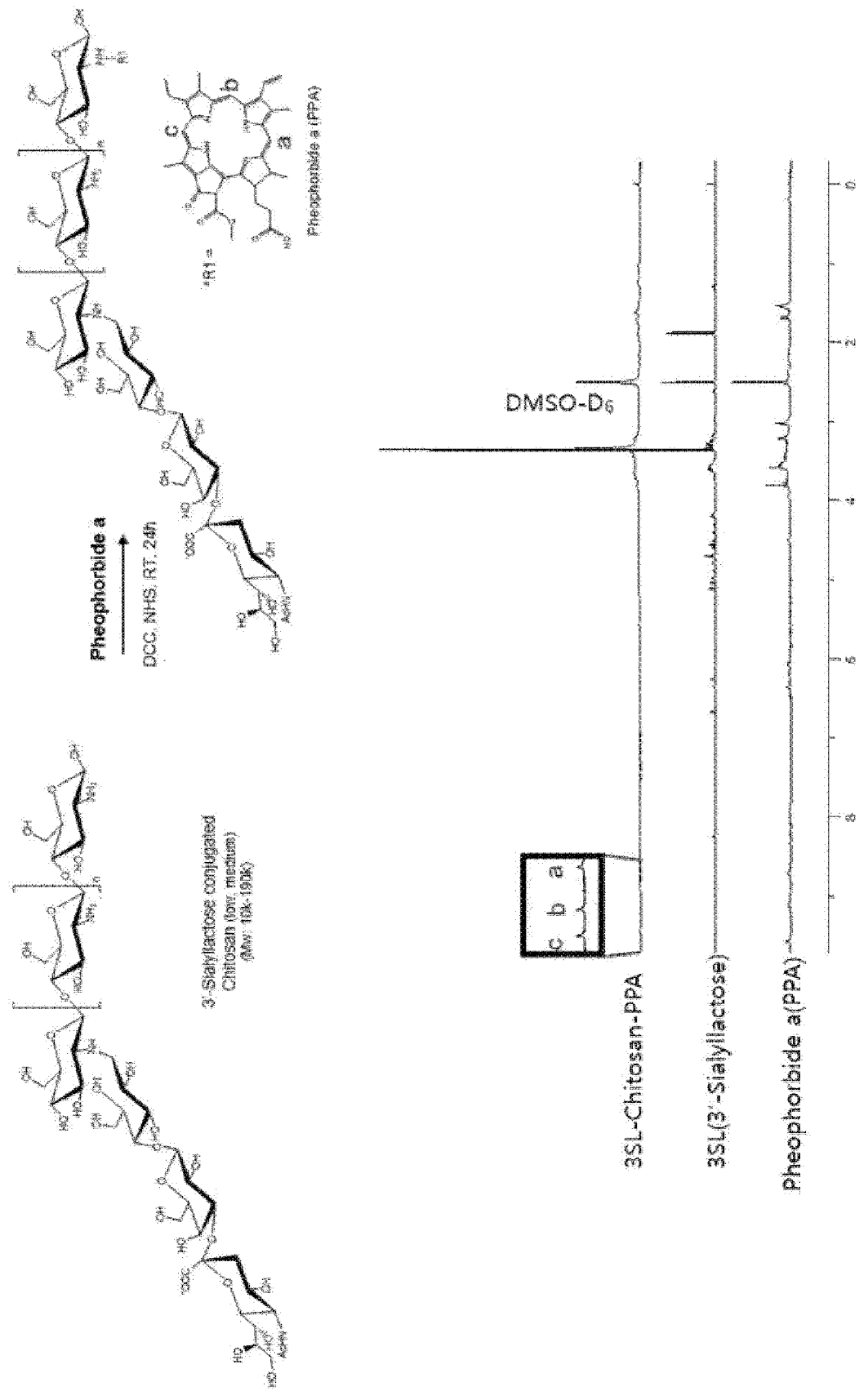
[FIG. 31]

[FIG. 32]
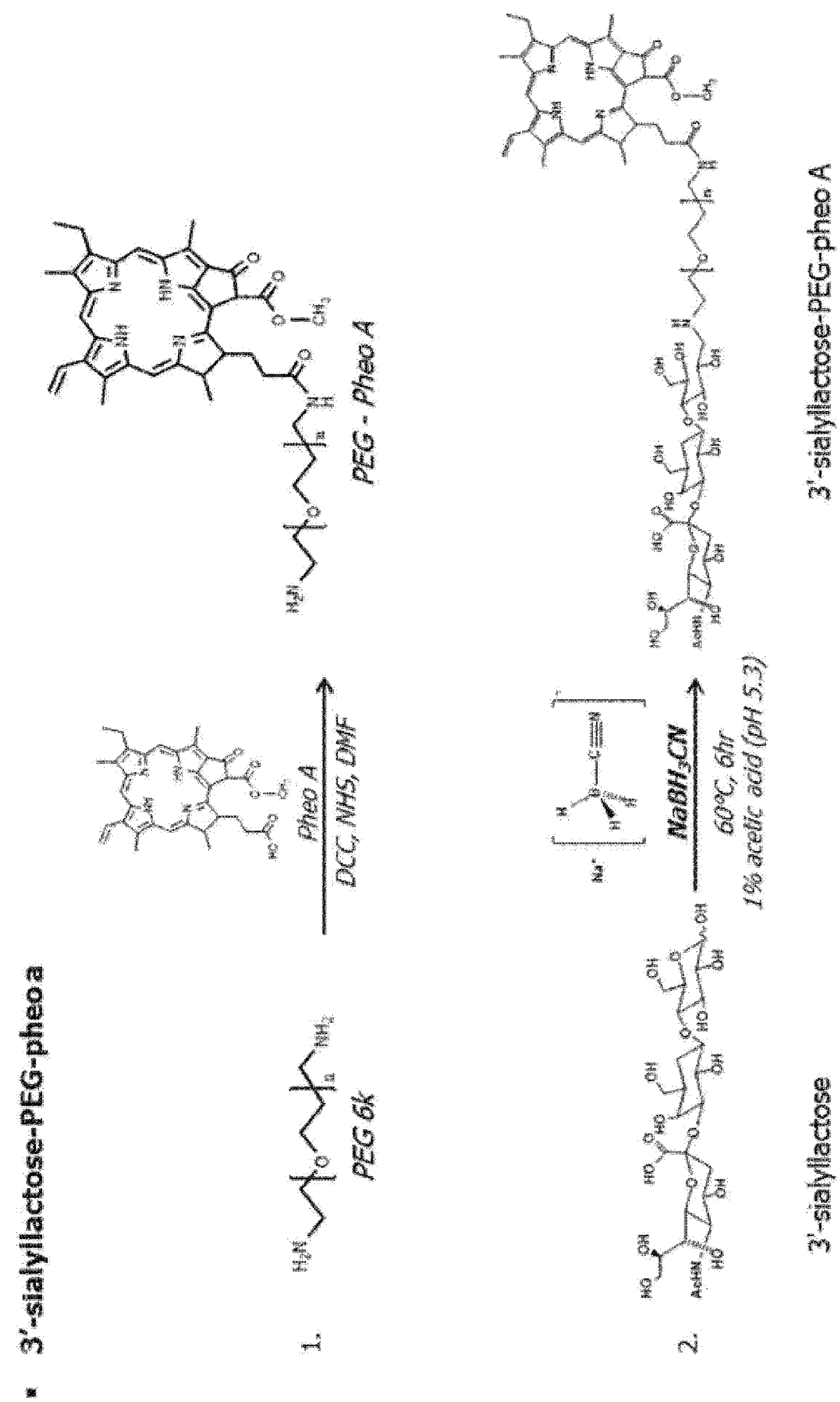

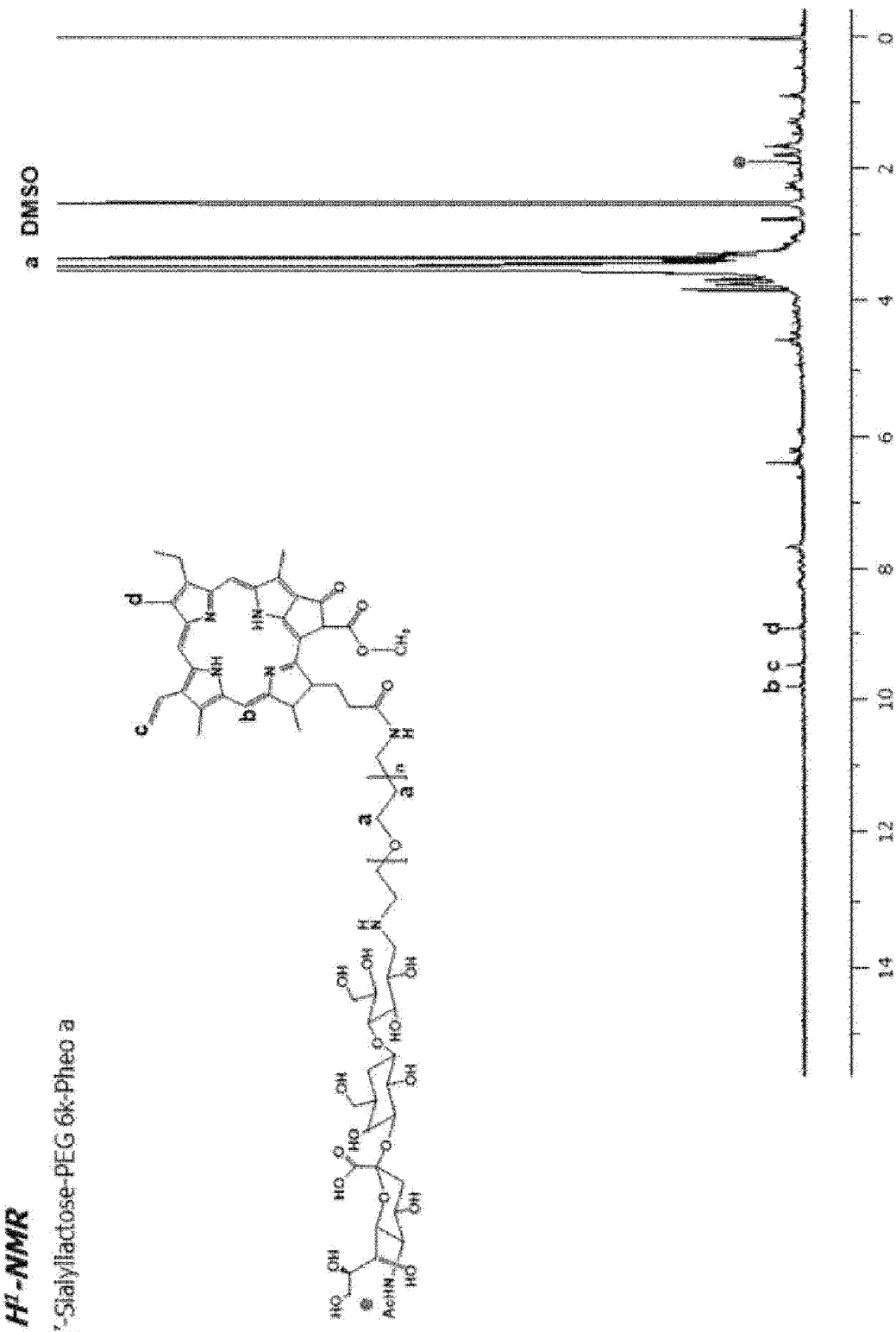
[FIG. 33]
* $H^1$-NMR
3'-Sialyllactose-PEG 6k-Pheo a

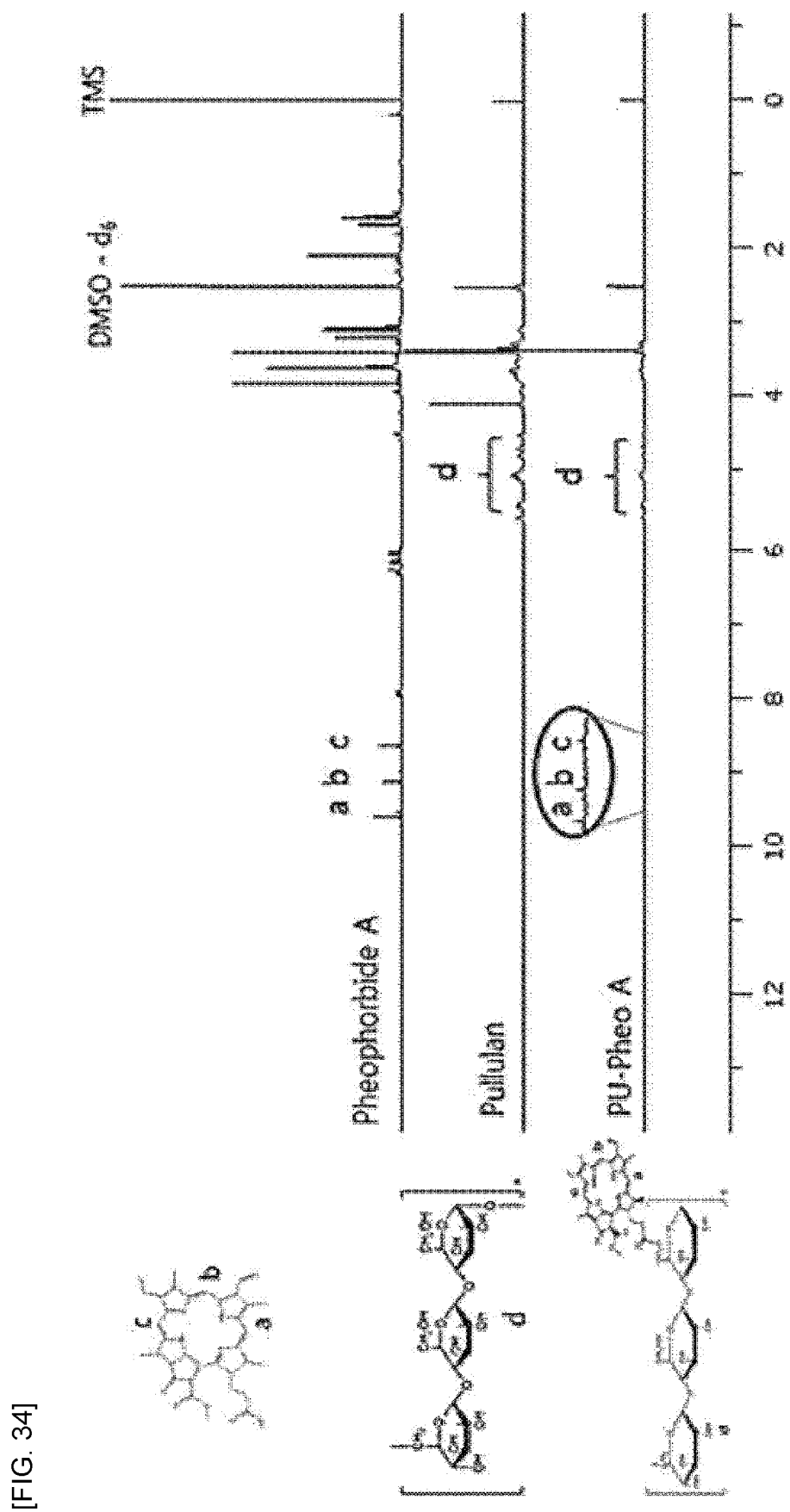
[FIG. 34]

[FIG. 35]
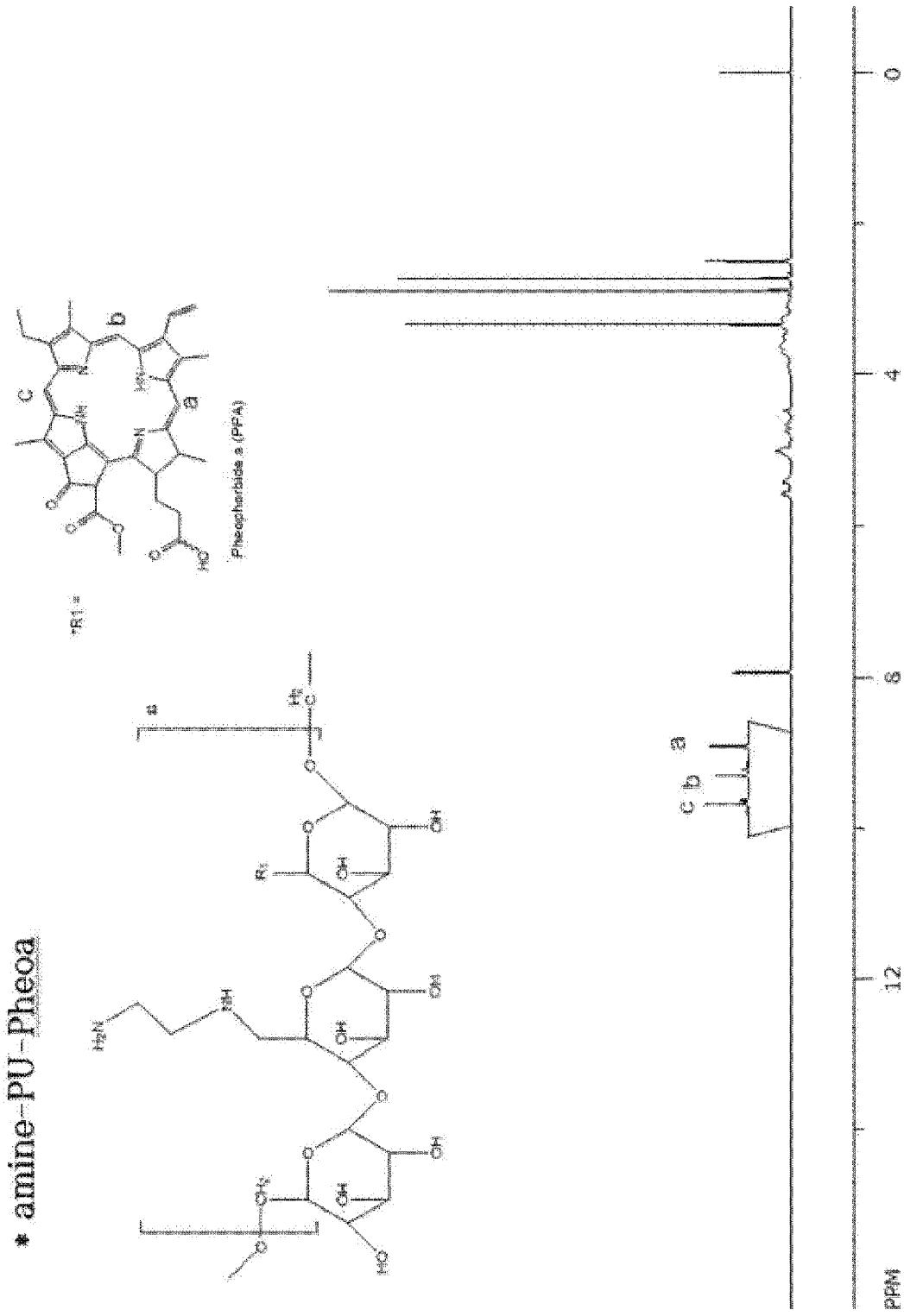

[FIG. 36]
* 3SL-PU-Pheoa
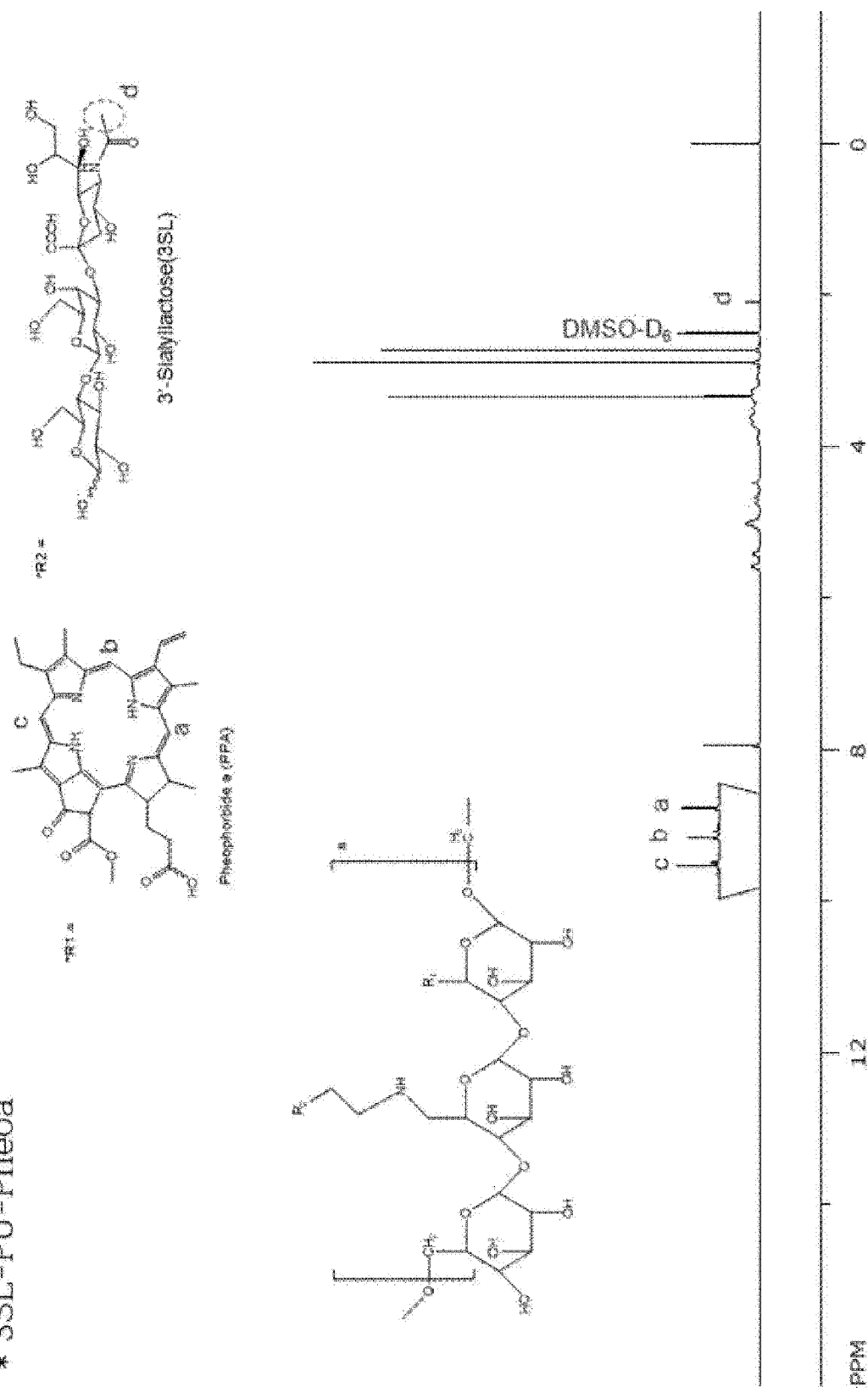

[FIG. 39]
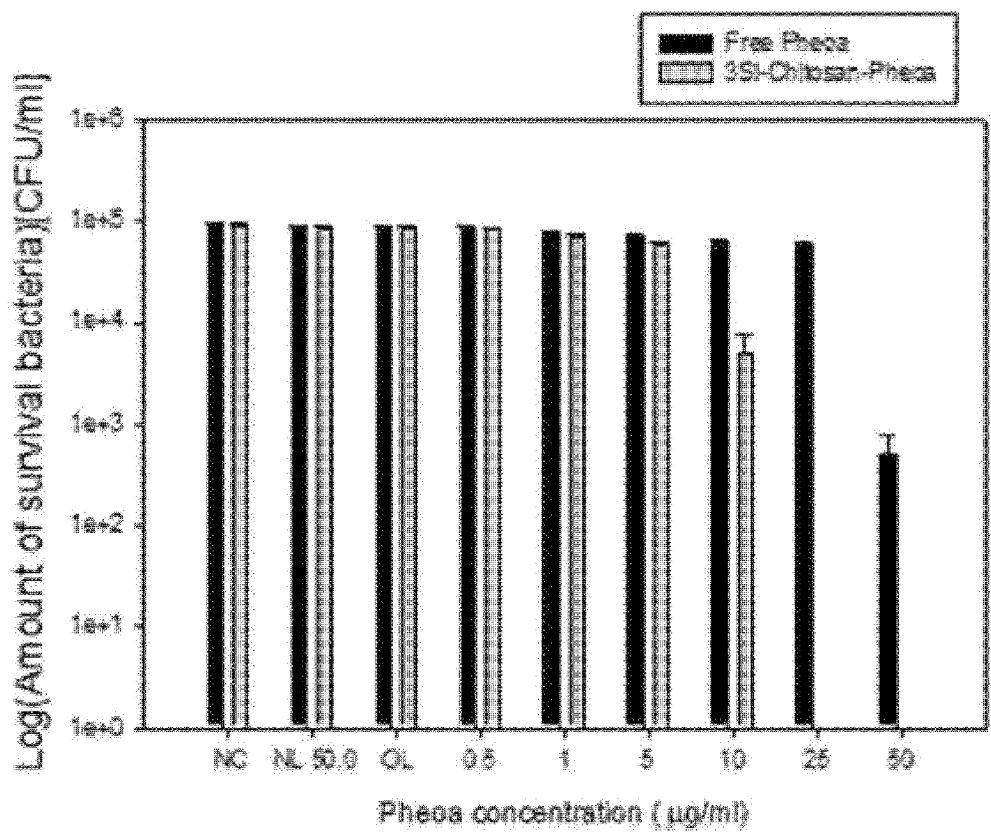
[FIG. 40]

[FIG. 41]
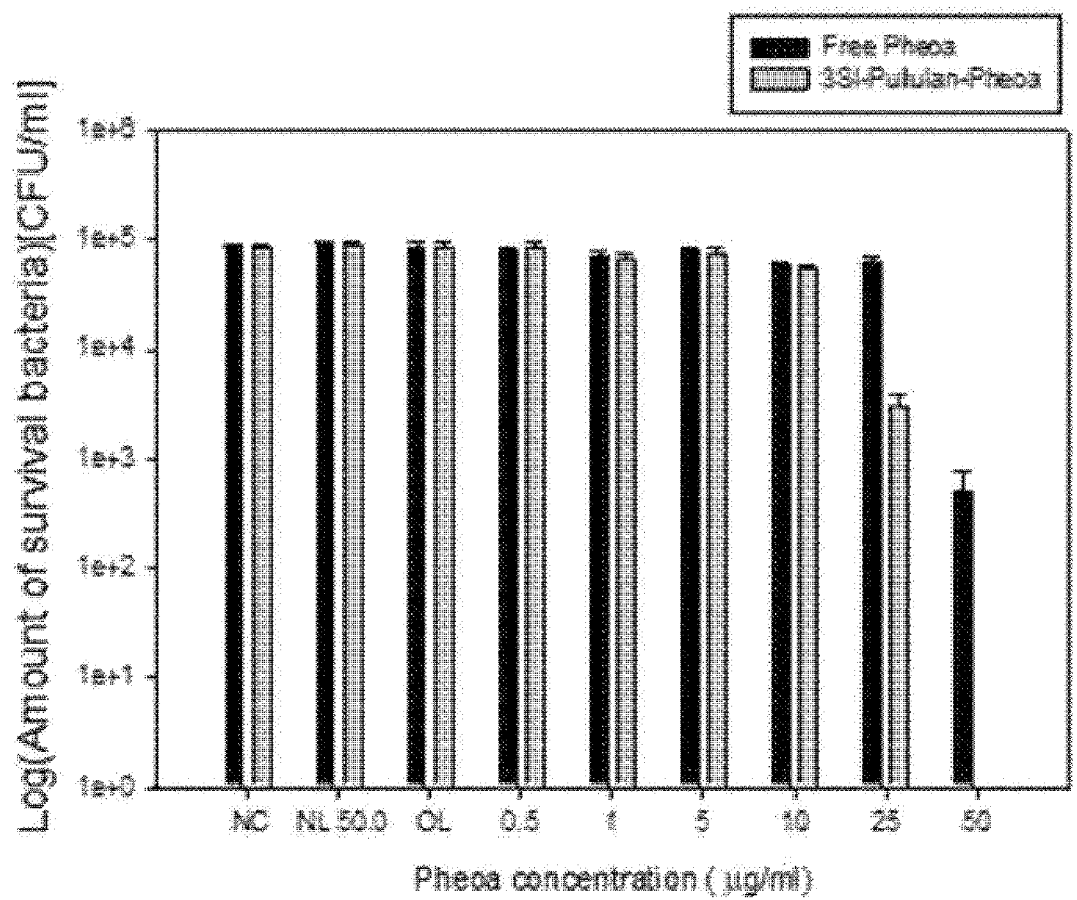

POLYMER COMPOSITE FOR HELICOBACTER PYLORI RECOGNITION AND COMPOSITION FOR PHOTODYNAMIC THERAPY COMPRISING SAME

TECHNICAL FIELD

The present invention relates to a polymer composite for recognizing *Helicobacter pylori* and its uses.

BACKGROUND ART

*Helicobacter pylori* is screw-shaped Gram-negative bacteria that lives in the stomach of humans and animals. It creates an enzyme called Urase, which decomposes urea in gastric mucus into ammonia and carbon dioxide and it locally neutralizes the stomach acid around *Helicobacter pylori* to live by settling (infecting) in the stomach.

In addition, on the surface of *Helicobacter pylori*, there is a cell surface component attachment site called SabA (Sialic acid binding adhesin), which facilitates infection or adhesion of *Helicobacter pylori* to gastric epithelial cells, and SabA of *Helicobacter pylori* is known to attach to sialylated/fucosylated glycan on the cell surface.

The ability to bind to glycosylated epithelial cells is known to be essential for *Helicobacter pylori* to cause persistent infection and disease. Infection with *Helicobacter pylori* is known to lead to the occurrence of chronic gastritis, gastric ulcer, duodenal ulcer and gastric cancer, and is a first-class carcinogen regulated by the International Cancer Institute.

These infections of *Helicobacter pylori* are known to infect 30 to 50% of the general population in Western countries, and as *Helicobacter pylori* therapy, which is currently used in clinical practice worldwide, triple therapy consisting of proton pump inhibitors of omeprazole, amoxicillin and clarithromycin has been used as a first-line standard therapy, however increased resistance to clarithromycin is known to be a major cause of failure of eradication treatment.

When the first treatment using the triple therapy fails or there are resistant bacteria, metronidazole, tetracycline, quinolone, and the like are used as substitutes, but these also have a problem of increasing antibiotic resistance. Accordingly, there is a need for research and development on a new method for treating *Helicobacter pylori* that can solve the limitations of *Helicobacter pylori* antibiotic-based therapeutic agents.

DISCLOSURE

Technical Problem

The present invention relates to a polymer composition for photodynamic therapy of *Helicobacter pylori* to effectively treat a *Helicobacter pylori* infection, which was difficult to completely eradicate due to a conventional antibiotic resistance problem, the polymer composition selectively binds to *Helicobacter pylori* bacteria and can treat infections of *Helicobacter pylori* through singlet oxygen generated from a photosensitizer combined with a polymer upon laser irradiation.

Technical Solution

The present invention provides a polymer composite for recognizing *Helicobacter pylori* comprising a photosensitizer; sialyllactose; and a water-soluble polymer as a linker.

The present invention provides a pharmaceutical composition for photodynamic treatment of gastric disease induced by *Helicobacter pylori* comprising a polymer complex for recognizing *Helicobacter pylori* comprising a photosensitizer; sialyllactose; and a water-soluble polymer as a linker.

In addition, the present invention provides a composition for *Helicobacter pylori* infection diagnosis comprising a polymer complex for recognizing *Helicobacter pylori* comprising a photosensitizer; sialyllactose; and a water-soluble polymer as a linker.

Advantageous Effects

According to the present invention, it was confirmed that a water-soluble polymer-photosensitizer complex in which sialyllactose, which selectively binds to the surface of *Helicobacter pylori*, is conjugated, has excellent selectivity and binding power to the *Helicobacter pylori* strain, and the photosensitizer in the complex generates singlet oxygen when irradiated with laser to effectively induce the inactivation of *Helicobacter pylori* and it is intended to provide the complex as a polymer complex for recognizing *Helicobacter pylori* to effectively detect *Helicobacter pylori* in the gastrointestinal tract and to provide a *Helicobacter pylori* photodynamic therapy to solve the conventional antibiotic resistance problem.

DESCRIPTION OF DRAWINGS

FIG. 1 shows a schematic diagram in which a *Helicobacter pylori*-recognizable polymer interacts with SabA on the surface of *Helicobacter pylori* to bind to the surface of *Helicobacter pylori* and induces *Helicobacter pylori* death by the action of singlet oxygen generated from a photosensitizer during laser irradiation.

FIG. 2 shows the $H^1$-NMR spectrum of NCA-carbobenzyloxy-L-lysine.

FIG. 3 shows the $H^1$-NMR spectrum of butyl-poly(carbobenzyloxy-lysine)$_{10}$ [Butyl-poly(Cbz-lysine)$_{10}$].

FIG. 4 shows the $H^1$-NMR spectrum of butyl-poly(Cbz-lysine)$_{10}$-pheoa.

FIG. 5 shows the $H^1$-NMR spectrum of butyl-poly(lysine)$_{10}$-Pheoa.

FIG. 6 shows the $H^1$-NMR spectrum of butyl-poly(3SL-lysine)$_{10}$-pheoa.

FIG. 7 is a result of confirming the singlet oxygen generation ability of butyl-poly(3SL-lysine)$_{10}$-pheoa.

FIG. 8 shows a confocal microscope analysis result confirming the interaction between butyl-poly(3SL-lysine)$_{10}$-pheoa and *Helicobacter pylori* 26695 strain and the inactivation of *Helicobacter pylori* by a photosensitizer.

FIG. 9 shows a result of confirming the cytotoxicity by concentration of butyl-poly(3SL-lysine)$_{10}$-pheoa in AGS cells.

FIG. 10 shows a result of confirming the cytotoxicity according to the laser irradiation dose of butyl-poly(3SL-lysine)$_{10}$-pheoa.

FIG. 11 shows a CFU analysis result confirming the antibacterial activity of butyl-poly(3SL-lysine)$_{10}$-pheoa against *Helicobacter pylori* 26695 strain in vitro.

FIG. 12 shows a CFU analysis result confirming the antibacterial activity of butyl-poly(3SL-lysine)$_{10}$-pheoa against *Helicobacter pylori* SS1 strain in vitro.

FIG. 13 shows a result of confirming the cell uptake rate of butyl-poly(3SL-lysine)$_{10}$-pheoa in vitro.

FIG. 14 shows a confocal microscope analysis result confirming the interaction between butyl-poly(3SL-lysine)$_{10}$-pheoa and *Helicobacter pylori* SS1 strain and the inactivation of *Helicobacter pylori* by a photosensitizer.

FIG. 15 shows a result of confirming the effect of *Helicobacter pylori* infection treatment on the Balb/c mouse *Helicobacter pylori* SS1 strain infection model of butyl-poly (3SL-lysine)$_{10}$-pheoa.

FIG. 16 shows the synthesis process of butyl-poly-(Cbz-lysine)$_{10}$-chlorin e6 and a nuclear magnetic resonance spectrum ($^1$H-NMR) analysis results confirming it.

FIG. 17 shows the process of removing the carbobenzyloxy group and a nuclear magnetic resonance spectrum ($^1$H-NMR) analysis result confirming the butyl-poly(lysine)$_{10}$-chlorin e6 from which the carbobenzyloxy group was removed.

FIG. 18 shows the conjugation process of butyl-poly (lysine)$_{10}$-chlorin e6 and sialyllactose (3SL) and a nuclear magnetic resonance spectrum ($^1$H-NMR) analysis result confirming hybridization material butyl-poly (3SL-lysine)$_{10}$-chlorin e6 through the conjugation process.

FIG. 19 shows the synthesis process of butyl-poly-(Cbz-lysine)$_{10}$-protoporphyrin IX and a nuclear magnetic resonance spectrum ($^1$H-NMR) analysis results confirming it.

FIG. 20 shows the process of removing a carbobenzyloxy group and a nuclear magnetic resonance spectrum ($^1$H-NMR) analysis result confirming butyl-poly(lysine)$_{10}$-protoporphyrin IX from which the carbobenzyloxy group was removed.

FIG. 21 shows the conjugation process of butyl-poly (lysine)$_{10}$-protoporphyrin IX and sialyllactose (3SL) and a nuclear magnetic resonance spectrum ($^1$H-NMR) analysis result of confirming hybridization material butyl-poly (3SL-lysine)$_{10}$-protoporphyrin IX through the conjugation process.

FIG. 22 shows the synthesis process of butyl-poly-(Cbz-lysine)$_{10}$-hematoporphyrin and a nuclear magnetic resonance spectrum ($^1$H-NMR) analysis result confirming it.

FIG. 23 shows the process of removing a carbobenzyloxy group and a nuclear magnetic resonance spectrum ($^1$H-NMR) analysis result of confirming butyl-poly(lysine)$_{10}$-hematoporphyrin from which the carbobenzyloxy group was removed.

FIG. 24 shows the conjugation process of butyl-poly (lysine)$_{10}$-hematoporphyrin and sialyllactose (3SL) and a nuclear magnetic resonance spectrum ($^1$H-NMR) analysis result of confirming hybridization material butyl-poly (3SL-lysine)$_{10}$-hematoporphyrin through the conjugation process.

FIG. 25 shows the synthesis process of succinylated silicon phthalocyanine (SSiPC) and a nuclear magnetic resonance spectrum ($^1$H-NMR) analysis results confirming it.

FIG. 26 shows the synthesis process of poly-(Cbz-lysine)$_{10}$-silicon phthalocyanine and a nuclear magnetic resonance spectrum ($^1$H-NMR) analysis result confirming it.

FIG. 27 shows a process of removing a carbobenzyloxy group and a nuclear magnetic resonance spectrum ($^1$H-NMR) analysis result confirming butyl-poly(lysine)$_{10}$-silicone phthalocyanine from which the carbobenzyloxy group was removed.

FIG. 28 shows the conjugation process of butyl-poly (lysine)$_{10}$-silicon phthalocyanine and sialyllactose (3SL) and a nuclear magnetic resonance spectrum ($^1$H-NMR) analysis result of confirming hybridization material butyl-poly (3SL-lysine)$_{10}$-silicon phthalocyanine through the conjugation process.

FIG. 29 shows a chitosan purified by lyophilization and a nuclear magnetic resonance spectrum ($^1$H-NMR) analysis result confirming it.

FIG. 30 shows the conjugation process of chitosan and sialyllactose (3SL) and a nuclear magnetic resonance spectrum ($^1$H-NMR) analysis result confirming hybridization material chitosan-3'-sialyllactose through the conjugation process.

FIG. 31 shows a chitosan-3SL-Pheoa complex obtained by combining chitosan-3'-sialyllactose and pheophorbide a (Pheoa) which is a chlorin-based photosensitizer, and a nuclear magnetic resonance spectrum ($^1$H-NMR) analysis result confirming it.

FIG. 32 shows the synthesis process of 3'-sialyllactose-polyethylene glycol (PEG)-Pheoa complex.

FIG. 33 shows a nuclear magnetic resonance spectrum ($^1$H-NMR) analysis result confirming 3'-sialyllactose-polyethylene glycol-Pheoa complex.

FIG. 34 shows a process of producing Pullulan-pheophorbide a [PU-Pheoa] complex and a nuclear magnetic resonance spectrum ($^1$H-NMR) analysis result confirming it.

FIG. 35 shows the amination process of Pullulan-pheophorbide a [PU-Pheoa] complex and a nuclear magnetic resonance spectrum ($^1$H-NMR) analysis result confirming it.

FIG. 36 shows the conjugation process of Pullulan-pheophorbide a [PU-Pheoa] complex and sialyllactose (3SL) and a nuclear magnetic resonance spectrum ($^1$H-NMR) analysis result confirming hybridization material 3SL-Pullulan-pheophorbide a [3SL-Pullulan-Pheoa] through the conjugation process.

FIG. 39 shows a CFU (Colony forming units) analysis result of confirming the antibacterial activity of chitosan-3SL-Pheoa complex against *Helicobacter pylori* bacteria.

FIG. 40 shows an inhibition zone analysis result of confirming the antibacterial activity of 3SL-polyethylene glycol (PEG)-Pheoa complex against *Helicobacter pylori* bacteria.

FIG. 41 shows a CFU (Colony forming units) analysis result of confirming the antibacterial activity of 3SL-Pullulan-pheophorbide a complex against *Helicobacter pylori* bacteria.

BEST MODE

Figure 37:
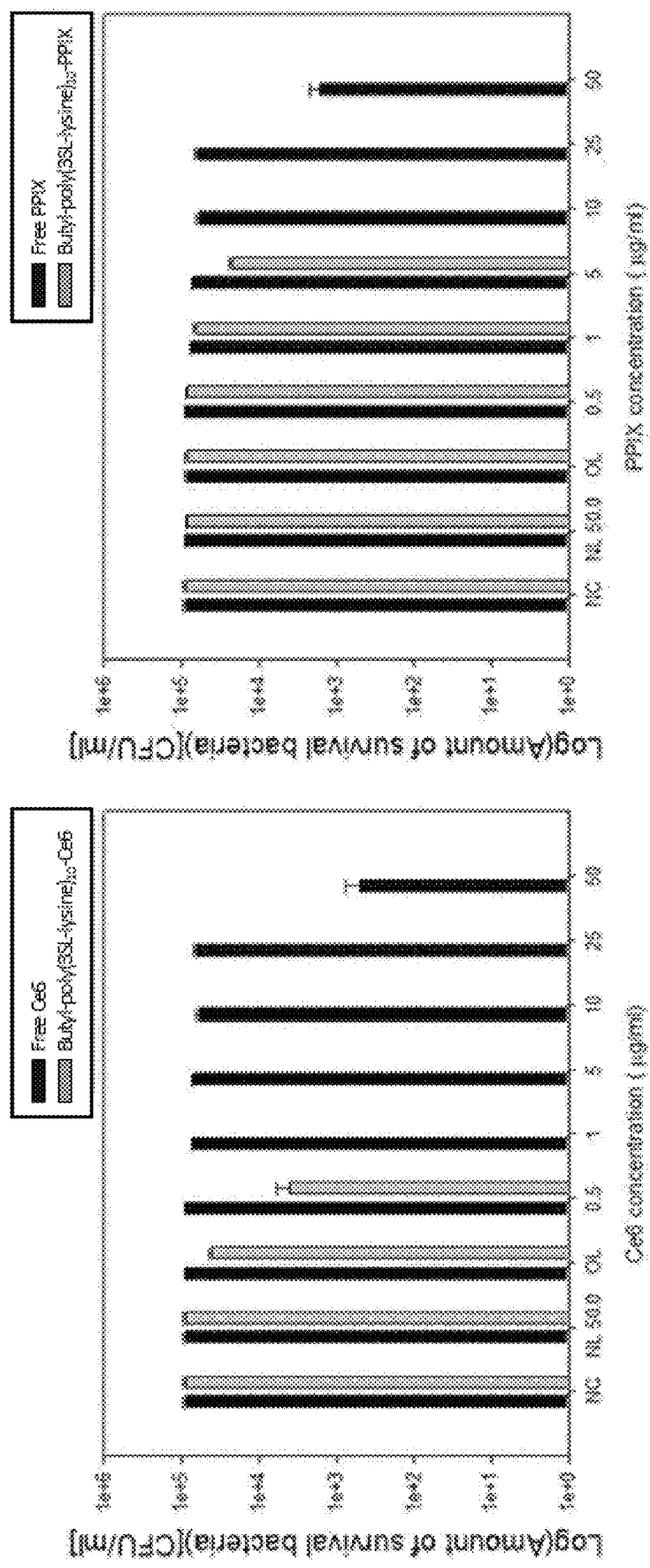
FIG. 37 shows a CFU (Colony forming units) analysis result confirming the antibacterial activity of butyl-poly (3SL-lysine)$_{10}$-Ce6 and butyl-poly(3SL-lysine)$_{10}$-PPIX against *Helicobacter pylori* bacteria.

Hereinafter, the present invention will be described in more detail.

The present invention may provide a polymer composite for recognizing *Helicobacter pylori* comprising a photosensitizer; sialyllactose; and a water-soluble polymer as a linker.

The polymer composite may be formed by bonding amine group or hydroxy group of the water-soluble polymer and carboxy group of the photosensitizer.

The polymer composite may be formed by bonding amine group of the water-soluble polymer and hydroxy group of the sialyllactose.

More specifically, a double bond is formed by combining aldehyde of an intermediate of sialyllactose glucose ring and the amine group of the water-soluble polymer, and at this time, as the double bond is reduced by the NaCNBH$_3$ additive, the double bond is converted into a single bond, so that the hydroxy group of sialyllactose and the amine group of the water-soluble polymer can be finally bonded.

In the polymer complex, the carboxy group of the photosensitizer and the hydroxy group of sialyllactose may be bonded to different amine groups of the water-soluble polymer, respectively, or the carboxy group of the photosensitizer and the hydroxyl group of the water-soluble polymer are bonded, and then the hydroxy group of sialyllactose and the amine group of the water-soluble polymer may be bonded, but it is not limited thereto.

The water-soluble polymer may be selected from the group consisting of polylysine, polyethylene glycol, polyethyleneimine, pullulan, chondroitin sulfate, hyaluronic acid, chitosan, polycaprolactone and polydioxane.

The photosensitizing agent may be selected from the group consisting of chlorins, porphyrins and phthalocyanine, and more preferably pheophorbide a.

The sialyllactose may be 3'-sialyllactose.

In more detail, the 3'-sialyllactose interacts with SabA on the surface of *Helicobacter pylori* and can bind to accurately recognize *Helicobacter pylori*.

According to an example of the present invention, in order to confirm the *Helicobacter pylori* inactivation effect of butyl-poly(3SL-lysine)$_{10}$-Pheoa (HSP), the antibacterial activity effect against *Helicobacter pylori* 26695 strain was compared between hybridization polymers in which 3'-sialyllactose (3SL), or 6'-sialyllactose (6SL), which is an isomer of 3'-sialyllactose, which represents *Helicobacter pylori* recognition in the hybridization polymer, is bound, and the effect of the recognition ability of 3'-sialyllactose (3SL) of HSP on the antibacterial activity of *Helicobacter pylori* was confirmed through the comparison with the experimental group of Pre3SL+butyl-poly(3SL-lysine)$_{10}$-Pheoa, which interacts competitively with sialyllactose.

As a result, in the case of the *Helicobacter pylori* 26695 strain treated with butyl-poly(3SL-lysine)$_{10}$-Pheoa (HSP), the experimental group irradiated with a 1.2 J/cm$^2$ laser had the decreased number of *Helicobacter pylori* colonies at the level of 5×10$^5$ to 5×10$^4$ CFU/ml compared to the negative control group as shown in FIG. 11 and the growth of *Helicobacter pylori* in the experimental group irradiated with a laser of 2.4 J/cm$^2$ or more was no longer confirmed.

On the other hand, in the case of the butyl-poly(6SL-lysine)$_{10}$-Pheoa irradiated under the same laser condition and Pre3SL+butyl-poly(3SL-lysine)$_{10}$-Pheoa control group, it was confirmed that both did not interact properly with *Helicobacter pylori* and most of them were washed off in the washing step and showed very low antibacterial activity compared to butyl-poly(3SL-lysine)$_{10}$-Pheoa.

From the above results, it was confirmed that the *Helicobacter pylori* inactivation effect of butyl-poly(3SL-lysine)$_{10}$-Pheoa (HSP) was very excellent, and not all sialyllactose exhibited the same effect.

The *Helicobacter pylori* strain may be selected from the group consisting of *Helicobacter pylori* 26695, *Helicobacter pylori* SS1, *Helicobacter pylori* 51 and *Helicobacter pylori* 52.

The polymer composite for recognizing *Helicobacter pylori* may be represented by the following Chemical Formula 1:

[Chemical Formula 1]

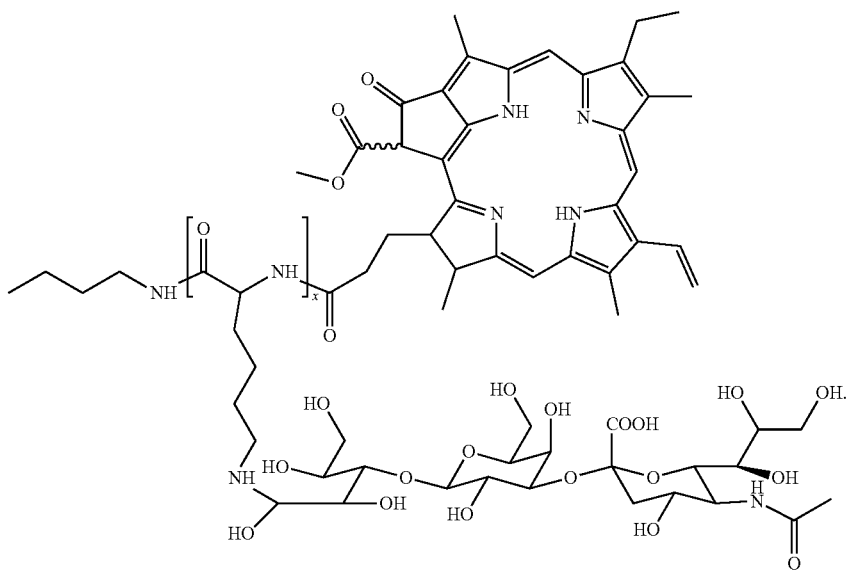

In Chemical Formula 1, X may be an integer of 1 to 15, more preferably X may be 10, but it is not limited thereto.

The present invention may provide a pharmaceutical composition for photodynamic treatment of gastric disease induced by *Helicobacter pylori* comprising a polymer complex for recognizing *Helicobacter pylori* comprising a photosensitizer; sialyllactose; and a water-soluble polymer as a linker.

The gastric disease may be selected from the group consisting of duodenal ulcer, gastritis, gastric ulcer, gastric dysplasia, hyperacidity, macrogastria, achlorhydria, aerophagia, gastric cramps, pyloric stenosis, gastric volvulus, gastric polyps, gastric bezoar and gastric cancer.

In one embodiment of the present invention, the pharmaceutical composition can be used as any one formulation selected from the group consisting of injections, granules, powders, tablets, pills, capsules, suppositories, gels, suspensions, emulsions, drops or solutions according to a conventional method.

Another embodiment of the invention may further comprise at least one additive selected from the group consisting of carriers, excipients, disintegrants, sweeteners, coating agents, swelling agents, lubricants, slip modifiers, flavors, antioxidants, buffers, bacteristats, diluents, dispersants, surfactants, binders and lubricants, which are commonly used in the preparation of pharmaceutical compositions for photodynamic treatment of gastric diseases related to *Helicobacter pylori* comprising a polymer represented by Chemical Formula 1 above.

Specially, examples of the carrier, excipient and diluent include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. Solid formulations for oral administration include tablets, pills, powders, granules, capsules, etc., and such solid formulations may contain at least one excipient such as starch, calcium carbonate, sucrose or lactose, gelatin and the like in addition to the composition. Furthermore, in addition to simple excipients, lubricants such as magnesium stearate and talc are also used. Examples of the liquid formulations for oral administration include suspensions, solutions, emulsions, syrups and the like, and various excipients such as wetting agents, sweeteners, fragrances, preservatives and the like may be included in addition to water and liquid paraffin which are commonly used as simple diluents. Formulations for parenteral administration include sterile aqueous solutions, non-aqueous solutions, suspensions, emulsions, freeze-dried preparations, suppositories and the like. Examples of the non-aqueous solution and the suspension include propylene glycol, polyethylene glycol, vegetable oil such as olive oil, injectable ester such as ethyl oleate, and the like. As the base of the suppository, witepsol, macrogol, tween 61, cacao butter, laurinum, glycerogelatin and the like can be used.

According to one embodiment of the invention, the pharmaceutical composition may be administered intravenously, intraarterially, intraperitoneally, intramuscularly, intrasternally, transdermally, nasally, inhaled, topically, rectally, orally, intraocularlly or intradermally to the subject in the conventional manner.

The preferred dosage of the compound represented by Chemical Formula 1 may vary depending on the condition and weight of the subject, the type and extent of the disease, the drug form, the route of administration, and the duration, and may be appropriately selected by those skilled in the art. According to one embodiment of the present invention, the daily dosage may be, but is not limited to, 0.01 to 200 mg/kg, specifically 0.1 to 200 mg/kg, more specifically 0.1 to 100 mg/kg. Administration may be administered once a day or divided into several times, and the scope of the invention is not limited thereto.

In the present invention, the 'subject' may be a mammal including a human, but it is not limited thereto.

In addition, the present invention may provide a composition for *Helicobacter pylori* infection diagnosis comprising a polymer complex for recognizing *Helicobacter pylori* comprising a photosensitizer; sialyllactose; and a water-soluble polymer as a linker.

Hereinafter, the present invention will be described in more detail through examples. These examples are only intended to illustrate the present invention in more detail, and it will be apparent to those skilled in the art that the scope of the present invention is not limited by these examples according to the gist of the present invention. The examples of the present invention are provided to more completely explain the present invention to those of ordinary skill in the art.

<Example 1> Preparation of Hybrid Polymer Using Conjugation of Polylysine-Pheophorbide a Photosensitizer Conjugate and Sialyllactose 1-1. Synthesis of NCA-Carbobenzyloxy-L-Lysine (NCA-Cbz-Lysine)

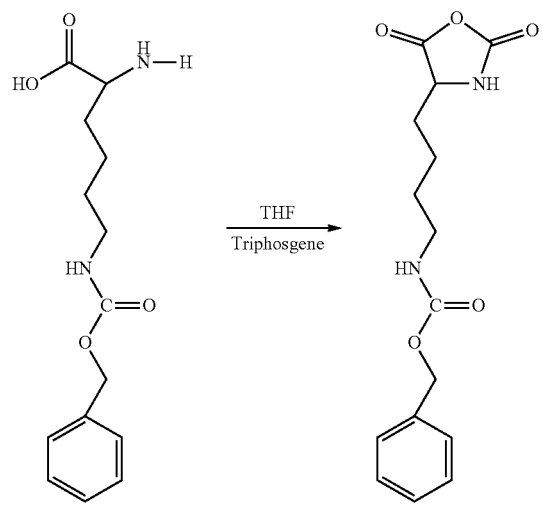

[Reaction Scheme 1]

After adding 3 g of N6-carbobenzyloxy-L-lysine to a 200 ml round bottom flask containing 50 ml of tetrahydrofuran (THF) and completely dissolving it, 3 g of triphosgene was added to the round bottom flask and completely dissolved by mixing using a magnetic bar.

Thereafter, it was reacted at 60° C. for 4 hours in an oil bath. After filtration using a glass & paper filter, 900 ml of hexane was added dropwise to perform a precipitation reaction. Then, after filtering again using a glass paper filter paper, hexane was completely removed from the reaction product for 12 hours using a vacuum pump. As a result, about 3 g of NCA-carbobenzoyloxy-L-lysine (NCA-Cbz-Lysine) was recovered as shown in FIG. 2, and the compound was identified through a nuclear magnetic resonance spectrum ($^1$H-NMR).

1-2. Synthesis of poly-Carbobenzyloxy-L-Lysine [poly(Cbz-Lysine)$_x$]

[Reaction Scheme 2]

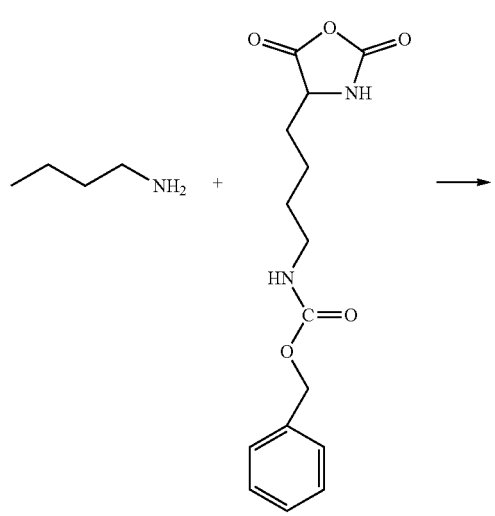

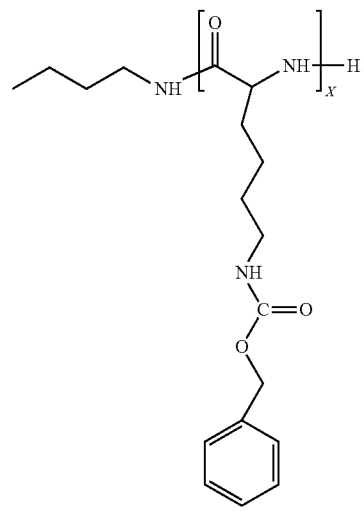

To produce poly-carbobenzyloxy-L-lysine, 90 µl of butyl-amine as a reaction initiator was dissolved in 10 ml of DMF, and 3 g of NCA-carbobenzoyloxy-L-lysine recovered in Example 1-1 was dissolved in 20 ml of DMF. The NCA-carbobenzoyloxy-L-lysine solution was added dropwise to the butyl-amine solution to proceed with the reaction, reacted for 48 hours, and then dropwise added to 300 ml ether to perform the precipitation reaction.

The precipitation reaction solution was divided into 50 ml falcon tubes and centrifuged at 3000 rpm for 5 minutes, and then the supernatant was discarded and unreacted substances were removed by repeating 5 times with a new ether solution.

Thereafter, the ether was completely removed using a vacuum pump for 12 hours, and the reaction product was recovered, and confirmed through a nuclear magnetic resonance spectrum ($^1$H-NMR).

As a result, a compound as shown in FIG. 3 was obtained, and x was confirmed to be about 10.

1-3. Synthesis of Polylysine-Pheophorbide a

Conjugate [poly-(Cbz-Lysine)$_{10}$-Pheophorbide a]

[Reaction Scheme 3]

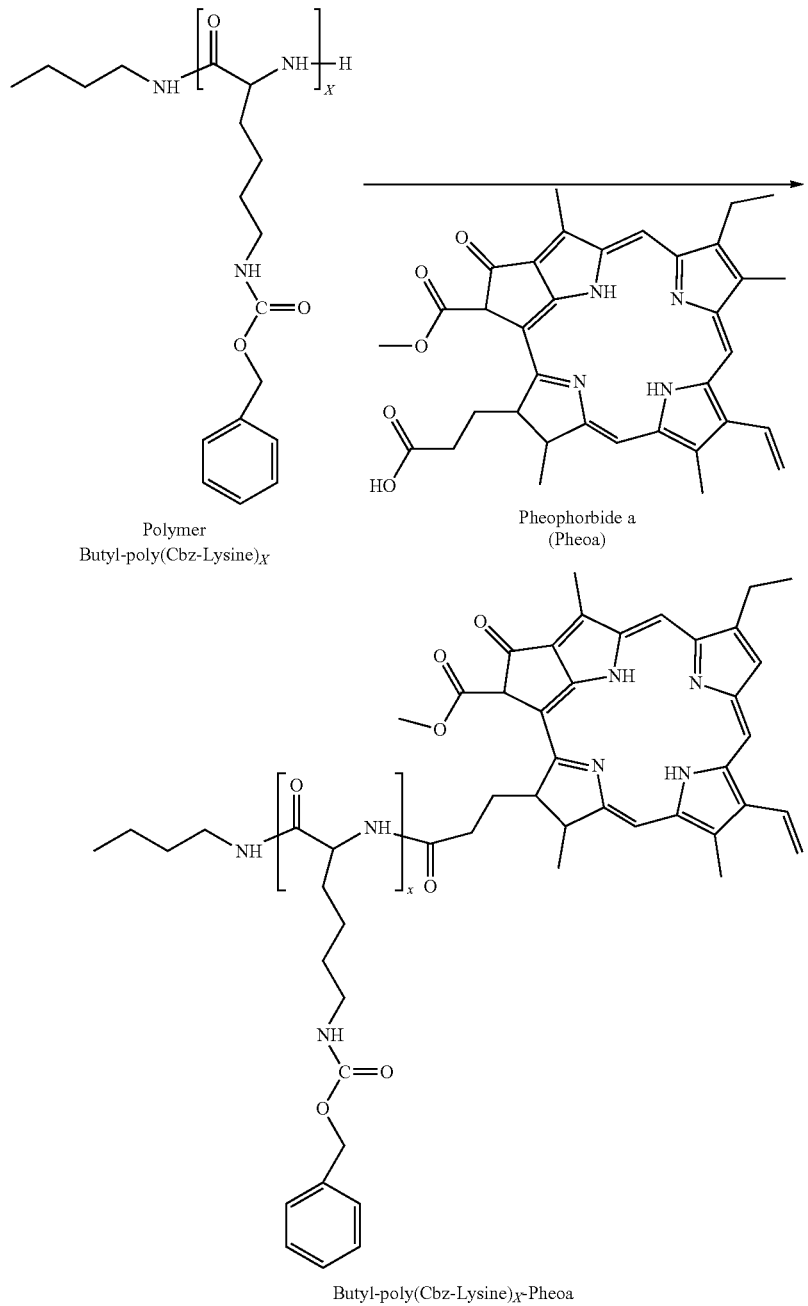

Pheophorbide a (Pheoa) of 250 mg, DCC (dicyclohexyl-carbodiimide) of 108 mg and NHS (N-hydroxysuccinimide) of 66 mg were dissolved in DMF (dimethylformamide) of 10 ml and activated by mixing for 4 hours to activate 1 g of butyl-poly(carbobenzyloxy-lysine)$_{10}$ recovered in Example 1-2 was dissolved in 10 ml DMF.

Then, after removing DCU (dicyclohexyl urea) from the activated pheophorbide a solution using a 0.45 syringe filter, butyl-poly(carbobenzyloxy-lysine)x solution was added dropwise and reacted for 24 hours.

After 24 hours, ether was added to proceed with the precipitation reaction, transferred to a 50 ml Falcon tube, and centrifuged at 3000 rpm for 5 minutes. After centrifugation, the supernatant was discarded and resuspended with a new ether solution, and the above process was repeated 5 times to remove unreacted substances.

After the ether was completely removed using a vacuum pump for 12 hours, the reactant, butyl-poly(Cbz-lysine)$_{10}$-Pheoa was recovered, and a nuclear magnetic resonance spectrum ($^1$H-NMR) result as shown in FIG. 4 was obtained.

1-4. Preparation of poly(lysine)₁₀-Pheoa

[Chemical Formula 4]

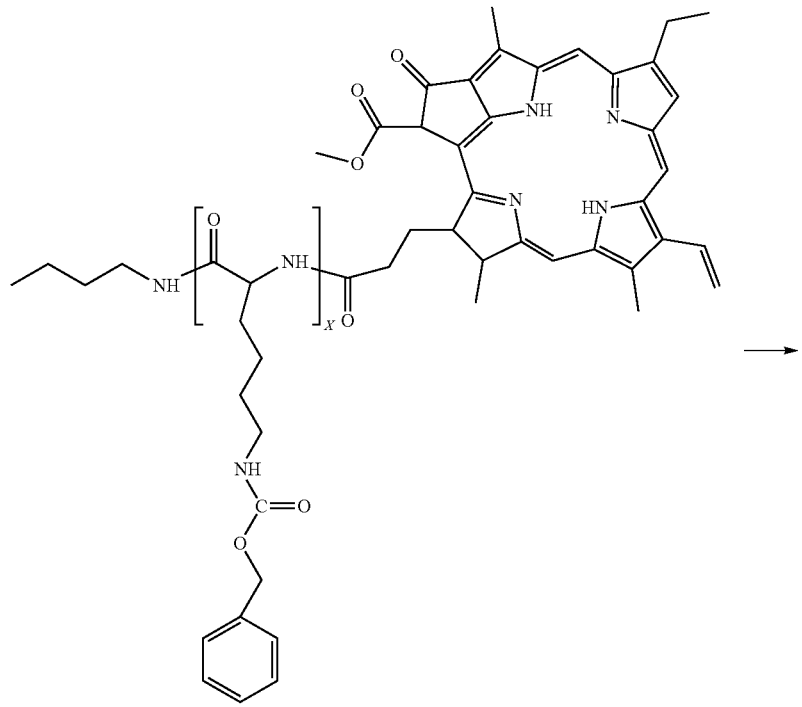

Butyl-poly(Cbz-Lysine)$_X$-Pheoa

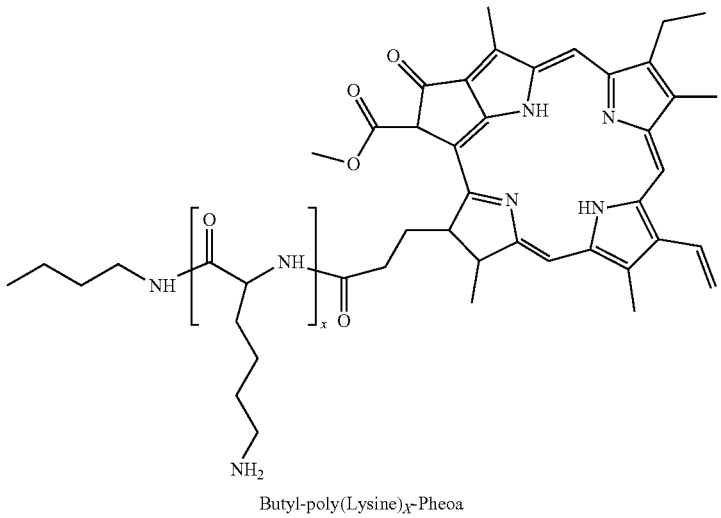

Butyl-poly(Lysine)$_X$-Pheoa

To remove the carbobenzyloxy group (Cbz) from the butyl-poly(Cbz-lysine)₁₀-Pheoa conjugate recovered in Example 1-3 above, 500 mg of butyl-poly(Cbz-lysine)₁₀-Pheoa was dissolved in 3 ml of TFA, HBr was dissolved in 3 ml of acetic acid at a concentration of 33%, and then put into a 20 ml vial and mixed for 30 minutes.

100 ml of ether/ethanol solution (50/50 vol %) was added to the mixture solution to perform a precipitation reaction, transferred to a 50 ml Falcon tube, centrifuged at 3000 rpm for 5 minutes, and the supernatant discarded and a new ether/ethanol solution (50/50 vol %) was added to perform the same procedure.

The above process was repeated 5 times to remove the unreacted substances, and after completely removing the ether/ethanol solution for 12 hours using a vacuum pump, the reactant was recovered.

As a result, a butyl-poly(lysine)₁₀-Pheoa conjugate showing a nuclear magnetic resonance spectrum ($^1$H-NMR) as shown in FIG. 5 was confirmed.

1-5. Preparation of Hybridization Polymer Through Conjugation of Polylysine-Pheophorbide a Conjugate and Sialyllactose

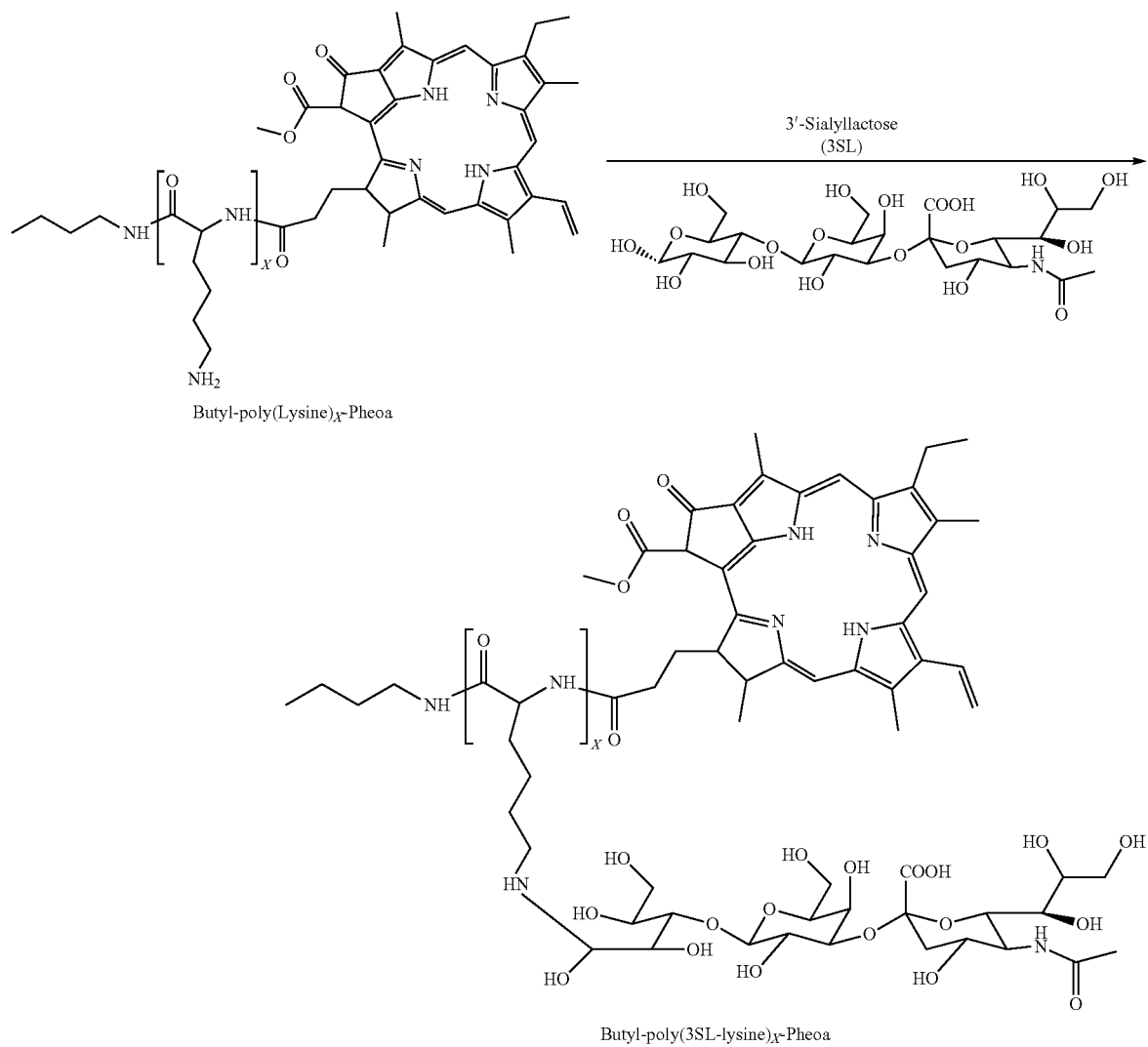

[Chemical Formula 5]

Butyl-poly(Lysine)$_x$-Pheoa

Butyl-poly(3SL-lysine)$_x$-Pheoa 300 mg of butyl-poly(lysine)$_x$-Pheoa recovered in the Example 1-4 was dissolved in 10 ml of acetate buffer (pH 5.5). 150 mg of 3'-sialyllactose (3SL) (1.5 times the number of moles of butyl-poly(lysine)$_{10}$-Pheoa) was dissolved in 5 ml acetate buffer (pH 5.5), and 15 mg of NaCNBH$_3$ (1.5 times the number of moles of butyl-poly(lysine)$_{10}$-Pheoa) was prepared by dissolving in 1 ml of DMSO.

Then, the solution was added to a 50 ml round bottom flask, mixed and reacted for 24 hours. Thereafter, distilled water was mixed with the reaction solution and dialyzed with primary distilled water for 72 hours using a dialysis membrane (molecular weight cutoff size 1000 Da). After dialysis, the reaction product was freeze-dried for 72 hours to recover the powdered hybridized polymer butyl-poly (3SL-lysine)$_{10}$-pheoa, and was identified by a nuclear magnetic resonance spectrum ($^1$H-NMR) as shown in FIG. 6.

<Example 2> Preparation of Hybrid Polymer Using Conjugation of Polylysine-Chlorine e6 Photosensitizer Conjugate and Sialyllactose 2-1. Preparation of Polylysine-Chlorin e6 Conjugate [Butyl-poly-(Cbz-Lysine)$_{10}$-Chlorin e6]

In the same process as in Example 1-3, butyl-poly-(Cbs-lysine)$_{10}$-chlorin e6 (Ce6) conjugate was prepared, and it was identified by nuclear magnetic resonance spectrum ($^1$H-NMR) as shown in FIG. 16.

2-2. Preparation of poly(lysine)$_{10}$-Ce6 [Butyl-poly(Lysine)$_{10}$-Ce6]

To remove the carbobenzyloxy group (Cbz) from the butyl-poly-(Cbs-lysine)$_{10}$-chlorine e6 conjugate recovered in Example 2-1, the same procedure as in Example 1-4 was performed. Thus, the butyl-poly(lysine)$_{10}$-Ce6 conjugate was recovered, and it was identified by a nuclear magnetic resonance spectrum ($^1$H-NMR) as shown in FIG. 17.

2-3. Preparation of Hybrid Polymer Using Conjugation of poly(lysine)$_{10}$-Ce6 and Sialyllactose In the same process as in Example 1-5, butyl-poly(lysine)$_{10}$-Ce6 recovered in Example 2-2 was conjugated to sialyllactose to prepare butyl-poly(3SL-lysine)$_{10}$-Ce6 hybrid polymer and it was identified by a nuclear magnetic resonance spectrum ($^1$H-NMR) as shown in FIG. 18.

<Example 3> Preparation of Hybrid Polymer Using Conjugation of Polylysine-Protoporphyrin Photosensitizer Conjugate and Sialyllactose 3-1. Synthesis of Polylysine-Protoporphyrin Conjugate [Butyl-poly-(Cbz-Lysine)$_{10}$-Protoporphyrin IX (PPIX)]

In the same process as in Example 1-3, butyl-poly-(Cbz-lysine)$_{10}$-PPIX conjugate was prepared, and it was identified by a nuclear magnetic resonance spectrum ($^1$H-NMR) as shown in FIG. 19.

3-2. Preparation of poly(lysine)$_{10}$-PPIX [Butyl-poly(Lysine)$_{10}$-PPIX]

Carbobenzyloxy group (Cbz) was removed from butyl-poly-(Cbz-lysine)$_{10}$-PPIX conjugate recovered in the Example 3-1-1 by performing the same procedure as in Example 1-4 to recover butyl-poly(lysine)$_{10}$-PPIX conjugate and it was identified by a nuclear magnetic resonance spectrum ($^1$H-NMR) as shown in FIG. 20.

3-3. Preparation of Hybrid Polymer Using butyl-poly(lysine)$_{10}$-PPIX Conjugate and Sialyllactose (3SL) Conjugation Sialyllactose was conjugated to butyl-poly(lysine)$_{10}$-PPIX conjugate recovered in the Example 3-1-2 in the same process as in Example 1-1-5, and it was identified by a nuclear magnetic resonance spectrum ($^1$H-NMR) as shown in FIG. 21.

<Example 4> Preparation of Hybrid Polymer Using Conjugation of Polylysine-Hematoporphyrin Photosensitizer Conjugate and Sialyllactose 4-1. Synthesis of Polylysine-Hematoporphyrin Conjugate [Butyl-poly-(Cbz-Lysine)$_{10}$-Hematoporphyrin (HPP)]

In the same process as in the Example 1-3, butyl-poly-(Cbz-lysine)$_{10}$-hematoporphyrin [Butyl-poly-(Cbz-Lysine)$_{10}$-HPP] conjugate was prepared, and it was identified by a nuclear magnetic resonance spectrum ($^1$H-NMR) as shown in FIG. 22.

4-2. Preparation of poly(lysine)$_{10}$-hematoporphyrin [Butyl-poly(Lysine)$_{10}$-HPP] Conjugate Carbobenzyloxy group (Cbz) was removed from butyl-poly-(Cbz-lysine)$_{10}$-hematoporphyrin conjugate recovered in the Example 3-2-1 by performing the same manner as in Example 1-4 to prepare butyl-poly(lysine)$_{10}$-HPP conjugate, and it was identified by a nuclear magnetic resonance spectrum ($^1$H-NMR) as shown in FIG. 23.

4-3. Preparation of Hybrid Polymer Using Conjugation of butyl-poly(lysine)$_{10}$-HPP Conjugate and Sialyllactose (3SL)

Sialyllactose was conjugated to butyl-poly(lysine)$_{10}$-HPP conjugate recovered in the Example 3-2-2 in the same process as in Example 1-5, and it was identified by a nuclear magnetic resonance spectrum ($^1$H-NMR) as shown in FIG. 24.

<Example 5> Preparation of Hybrid Polymer Using Conjugation of Polylysine-Phthalocyanine Conjugate and Sialyllactose 5-1. Synthesis of Succinylated Silicon Phthalocyanine 200 mg of silicon phthalocyanine (SiPC) was put into a 100 ml reactor and dissolved in 10 ml of pyridine. Thereafter, 348 mg of succinyl anhydride and 213 mg of 4-dimethylaminopyridine (DMAP) were dissolved in 5 ml of pyridine, added to the SiPC solution, and reacted with nitrogen purge at 100° C. for 24 hours. After evaporating all of pyridine, the solid reactant was dissolved in ethanol, and a precipitation reaction was carried out in distilled water at low temperature. It was transferred to a 50 ml Falcon tube and centrifuged at 3000 rpm for 5 minutes. The supernatant was discarded and the above process was repeated 3 times with fresh distilled water to remove unreacted substances. Then, lyophilization was performed for 72 hours to recover succinylated SiPC (SSiPC). As a result, it was confirmed as shown in FIG. 25 through a nuclear magnetic resonance spectrum ($^1$H-NMR).

5-2. Synthesis of Polylysine-Phthalocyanine Conjugate [Butyl-Poly-(Cbz-Lysine)$_{10}$-silicon Phthalocyanine (SiPC)]

Using the succinylated SiPC (SSiPC) recovered in the Example 4-1, butyl-poly-(Cbz-lysine)$_{10}$-phthalocyanine conjugate [Butyl-poly-(Cbz-Lysine)$_{10}$-SiPC] was synthesized and it was confirmed as shown in FIG. 26 through a nuclear magnetic resonance spectrum ($^1$H-NMR).

5-3. Production of poly(lysine)$_{10}$-SiPC [Butyl-poly(lysine)$_{10}$-SiPC]

Carbobenzyloxy group (Cbz) was removed from butyl-poly-(Cbz-lysine)$_{10}$-phthalocyanine conjugate recovered in the Example 4-2 by performing the same procedure as in Example 1-4 to prepare poly(lysine)$_{10}$-SiPC conjugate and it was identified as shown in FIG. 27 through a nuclear magnetic resonance spectrum ($^1$H-NMR).

5-4. Preparation of Hybrid Polymer Using Conjugation of butyl-poly(lysine)$_{10}$-SiPC Conjugate and Sialyllactose (3SL)

Sialyllactose was conjugated to butyl-poly(lysine)$_{10}$-SiPC conjugate recovered in the Example 4-3 in the same process as in Example 1-5, and it was identified as shown in FIG. 28 through a nuclear magnetic resonance spectrum ($^1$H-NMR).

<Example 6> Preparation of Complex for Recognizing *Helicobacter pylori* Capable of Photodynamic Therapy Based on Chitosan 6-1. Chitosan (Low Molecular, LM) Purification Chitosan (LM) of 671 mg was weighed and completely dissolved by stirring in 50 ml of 1% acetic acid solution for 12 hours. The completely dissolved chitosan solution was transferred to a dialysis membrane (12 k-14 k), dialysis was performed for 72 hours, and then purified chitosan was recovered through lyophilization, and it was identified as shown in FIG. 29 through a nuclear magnetic resonance spectrum ($^1$H-NMR).

6-2. Synthesis of Chitosan-Sialyllactose [Chitosan-(3'-Sialyllactose)] Conjugate To conjugate 3'-sialyllactose (3SL) for *Helicobacter* recognition to chitosan, 90 mg of purified chitosan is weighed and dissolved in 2 ml of 1% acetic acid solution by stirring, and then 4 ml of primary distilled water is added, mixed, and pH of the solution was confirmed (pH 4-5). 3SL and NaBH$_3$CN were each weighed and dissolved in 1 ml primary distilled water in 5 ml vial, respectively, put in an oil bath (55° C.) and reacted for 48 hours while stirring. Thereafter, the solution was transferred to a dialysis membrane (12 k-14 k), dialysis was performed for 3 days, and then lyophilized, and it was identified as shown in FIG. 30 through a nuclear magnetic resonance spectrum ($^1$H-NMR).

6-3. Synthesis of Chitosan-Sialyllactose-Chlorin-Based Photosensitizer Complex

In order to form a complex between the chitosan-sialyllactose conjugate (Chitosan-3SL) recovered through freeze-drying and the chlorine-based photosensitizer pheophorbide a (Pheoa), first, Pheoa, DCC (Dicyclohexylcarbodiimide) and NHS (N-Hydroxysuccinimide) was dissolved in 5 ml of DMSO at room temperature for 4 hours in a ratio of 1:1.2:1.2 and reacted. After 4 hours, the reaction by-product DCU (dicyclohexyl urea) was removed through centrifugation at 3000 rpm for 5 minutes.

The Pheoa solution and 300 mg of chitosan-3SL conjugate dissolved in 20 ml of distilled water were mixed, reacted at room temperature for 24 hours, and dialyzed (12 k-14 k) for 3 days. Afterwards, the excess free Pheoa precipitated with co-solvent was centrifuged at 3000 rpm for 5 minutes to remove unreacted substances and then freeze-dried to recover chitosan-3SL-Pheoa, and it was identified as shown in FIG. 31 through a nuclear magnetic resonance spectrum ($^1$H-NMR).

<Example 7> Preparation of Complex for Recognizing *Helicobacter pylori* Capable of Photodynamic Therapy Based on PEG Preparation of 3'-Sialyllactose-Polyethylene Glycol-Pheophorbide a [3SL-PEG-Pheoa] Complex In order to conjugate Pheoa, a chlorin-based photosensitizer, to polyethylene glycol (PEG) 6 k in the same process as in FIG. 32, Pheoa, DCC (dicyclohexylcarbodiimide) and NHS (N-hydroxysuccinimide) were added at room temperature for 4 hours at a ratio of 1:1.2:1.2, dissolved in 5 ml of DMF and after 4 hours, centrifuged at 3000 rpm for 5 minutes to remove generated reaction by-product DCU (dicyclohexyl urea). After reacting the PEG with Pheoa at a ratio of 1:1.2, PEG-Pheoa was purified using a hydrophobic column (LH20).

Purified PEG-Pheoa and 3SL were dissolved in 1% acetic acid (pH 5.2) at a ratio of 1:1.2, reacted at 60° C. for 24 hours, and then dialyzed (12 k-14 k) to remove unreacted substances, and the final 3SL-PEG-Pheoa complex was recovered and it was identified as shown in FIG. 33 through a nuclear magnetic resonance spectrum ($^1$H-NMR).

<Example 8> Preparation of Complex for Recognizing *Helicobacter pylori* Capable of Photodynamic Therapy Based on Pullulan 8-1. Preparation of Pullulan-Pheophorbide a [PU-Pheoa] Complex To prepare the PU-Pheoa conjugate, PU (50 mg) and Pheoa (10 mg) were dissolved in DMSO (10 ml), respectively. As catalysts and coupling reagents, DMAP and DCC were added to the Pheoa solution in a molar ratio of 1:1:1.5, respectively. After 4 hours, the Pheo A solution was added dropwise to the PU solution and stirred for 2 days.

The unreacted substances were removed by dialysis using a membrane of 12,000-14,000 MWCO for 3 days, and the purified PU-Pheoa conjugate was lyophilized, and it was identified as shown in FIG. 34 through a nuclear magnetic resonance spectrum ($^1$H-NMR).

8-2. Amination of Pullulan-Pheophorbide a [PU-Pheoa] Complex

In a 100 ml reactor, 500 mg of pullulan-pheophorbide a complex (PU-Pheoa) was dissolved in 10 ml of DMF (Dimethylformamide), and 100 µl of pyridine was added. Thereafter, 90 µl of thionyl chloride (SOCl$_2$) was added in the hood and reacted for 3 hours. At this time, the reactor was closed with a rubber stopper and two needles were inserted.

After the reaction, the reaction product was added to ether to proceed with the precipitation reaction, transferred to a 50 ml Falcon tube, and centrifuged at 3000 rpm for 5 minutes. After centrifugation, the supernatant was discarded and resuspended with a new ether solvent, and the above process was repeated 3 times to remove unreacted substances. Thereafter, the ether was completely removed using a vacuum pump for 12 hours, and the reaction product was recovered. The recovered reaction product was dissolved in 10 ml of DMF, and 1 ml of ethylenediamine (C$_2$H$_4$(NH$_2$)$_2$) was added to 15 ml of DMF. Thereafter, an ethylenediamine solution was added dropwise to the reactant solution, followed by reaction for 2 hours. After the reaction, the reaction product was added to ether to proceed with the precipitation reaction, transferred to a 50 ml Falcon tube, and centrifuged at 3000 rpm for 5 minutes. After centrifugation, the supernatant was discarded and the same procedure was performed with a fresh ether solution. Thereafter, the ether was completely removed using a vacuum pump for 12 hours, and the reaction product was recovered, and it was identified as shown in FIG. 35 through a nuclear magnetic resonance spectrum ($^1$H-NMR).

8-3. Preparation of 3SL-pullulan-pheophorbide a [3SL-PU-Pheoa] Complex

Purified amine-PU-Pheoa and 3SL were dissolved in DMSO and 1% acetic acid (pH 5.2) at a ratio of 1:1.2, respectively. NaCNBH$_3$ (1.5 times the number of moles of amine-PU-pheoa) was dissolved in DMSO and reacted at 60° C. for 24 hours, followed by dialysis using a dialysis membrane (MWCO:12 k-14 k) to remove unreacted substances and freeze-dried to final 3SL-PEG-Pheoa complex was recovered. The recovered complex was identified as shown in FIG. 36 through a nuclear magnetic resonance spectrum ($^1$H-NMR).

<Experimental Example 1> Confirmation of Singlet Oxygen (SOG) Generation Ability of *Helicobacter pylori* Recognition Photosensitized Hybridization Polymer It was confirmed whether the *Helicobacter pylori*-recognizable hybridization polymer prepared as in the Example 1 produced singlet oxygen by laser irradiation in the aqueous phase.

The hybridization polymer butyl-poly(3SL-lysine)$_{10}$-Pheoa prepared in the Example 1 and pheophorbide a were diluted to a concentration of 1 μg/mL using a UV spectrophotometer, and then it was mixed with SOSG (singlet oxygen sensor green) solution at 1:1 (v/v), irradiated with a laser of 20 mW intensity for 20 seconds each, and the ability of singlet oxygen generation (SOG) was confirmed using a fluorescence spectrophotometer.

As a result, it was confirmed that butyl-poly(3SL-lysine)$_{10}$-Pheoa as shown in FIG. 7 increased the fluorescence intensity value in proportion to the lapse of time when the laser was irradiated for up to 400 seconds, thereby increasing the production of singlet oxygen. While the fluorescence intensity value of pheophorbide a hardly increased even when irradiated with a laser.

From the above results, it was confirmed that the hybridization polymer butyl-poly(3SL-lysine)$_{10}$-Pheoa prepared in the Example 1 has a very excellent singlet oxygen generation ability compared to pheophorbide a which has poorly soluble in aqueous phase and thus it will be able to effectively solve the poorly soluble problem of pheophorbide a.

<Experimental Example 2> Confirmation of Interaction and Inactivation of *Helicobacter pylori* Recognition Hybridization Polymer Through a Confocal Microscope It was confirmed that the *Helicobacter pylori*-recognizable hybridization polymer synthesized as in the Example 1 interacts with *Helicobacter pylori* in vitro and can induce the inactivation of *Helicobacter pylori* by laser irradiation.

The hybridization polymer prepared in the Example 1, butyl-poly(3SL-lysine)$_{10}$-Pheoa, was diluted with distilled water based on 1 μg/ml of pheophorbide a after quantification using UV spectrophotometer.

*Helicobacter pylori* (26695 strain) of 1×10$^6$ CFU/ml was mixed with butyl-poly(3SL-lysine)$_{10}$-Pheoa solution and incubated at 37° C. for 2 hours.

As a control, 3'-sialyllactose (3SL) of 5 mg/ml was added to 1 ml (1×10$^6$ CFU/ml) of *Helicobacter pylori* for 30 minutes in advance, incubated, and then centrifuged (4000 rpm, 2 minutes) to remove the supernatant. Thereafter, it was re-dispersed with distilled water, and the above process was repeated twice, treated with butyl-poly(3SL-lysine)$_{10}$-Pheoa, and incubated at 37° C. for 2 hours. In addition, as a control, butyl-poly(Cbz-lysine)$_{10}$-Pheoa, (Cbz=carbobenzyloxy, expressed as nHSP), which does not have *Helicobacter pylori* recognition ability, was incubated at 37° C. for 2 hours.

After the incubation, each experimental group was centrifuged (4000 rpm, 2 minutes) to remove the supernatant and re-dispersed with distilled water (D.W), and the process was repeated twice. Thereafter, a total of 10 J/cm$^2$ laser was irradiated with 50 mW laser intensity.

In addition, *Helicobacter pylori* was stained with SYTO 9 and propidium iodide, and SYTO 9 (Green, Ex/Em 485/498), propidium iodide (Red, Ex/Em 535/617) and Cy5 (purple, Ex/Em 650/670) were observed with a confocal microscope.

As a result, as shown in FIG. 8, in the *Helicobacter pylori* group treated with butyl-poly(3SL-lysine)$_{10}$-Pheoa (HSP), the fluorescence of SYTO 9 (green) and Cy5 (purple) of pheophorbide a of HSP, which appears in normal *Helicobacter pylori* cells, mostly coincide, and thus it was confirmed that HSP interacts with *Helicobacter pylori*.

On the other hand, in the *Helicobacter pylori* group treated with butyl-(Cbz-lysine)$_{10}$-Pheoa (nHSP), SYTO 9 (Green) fluorescence appeared, but Cy5 (purple) fluorescence of pheophorbide a did not appear and it was confirmed that nHSP does not interact with *Helicobacter pylori*.

In addition, in the HSP-treated *Helicobacter pylori* group after pretreatment with 3'-sialyllactose (3SL) for 30 minutes (Pre3+HSP), SYTO 9 (green) appeared in normal *Helicobacter pylori* cells, but the fluorescence of Cy5 of pheophorbide a (purple) did not appear, and it was confirmed that *Helicobacter pylori* and HSP did not interact unlike the above case where the HSP was treated alone.

Meanwhile, as a result of confirming the *Helicobacter pylori* inactivation ability according to laser irradiation, as shown in FIG. 8, when laser irradiation to the HSP-treated *Helicobacter pylori* group [Laser (+)], after the interaction of HSP and *Helicobacter pylori*, by laser irradiation, propidium iodide (red) fluorescence was confirmed, which indicates damage to the cell membrane of *Helicobacter pylori* due to singlet oxygen generated in pheophorbide.

In addition, in other experimental groups, SYTO 9 (green) fluorescence appeared in normal *Helicobacter pylori* according to the presence or absence of laser irradiation, whereas propidium iodide (red) fluorescence was not confirmed.

From the above results, butyl-poly(3SL-lysine)$_{10}$-Pheoa (HSP) accurately recognizes and interacts with *Helicobacter pylori*, and effectively inactivates *Helicobacter pylori* through singlet oxygen generated from the photosensitizer of HSP interacted during laser irradiation.

<Experimental Example 3> Confirmation of Cytotoxicity of *Helicobacter pylori* Recognition Photosensitized Hybridization Polymer To confirm the cytotoxicity of the hybridized polymer butyl-poly(3SL-lysine)$_{10}$-Pheoa (HSP) synthesized as in the Example 1, AGS cells (human gastric cancer cells) were dispensed into each well at a concentration of 5×10$^3$ cells/well in a 96-well plate at a concentration of 100 μl, and cultured at 37° C. and 5% CO$_2$ for 24 hours. After 24 hours, the recognition hybridization polymer prepared in the Example 1 was treated in each well at a concentration of 0.5 to 50 μg/mL, reacted at 37° C. and 5% CO$_2$ for 4 hours, and subjected to MTT test, and then the fluorescence intensity was measured at 570 nm using a multi-reader (Synergy H1 Multi-mode Reader, Biotek), and cell viability was calculated compared to the control group treated with only pheophorbide a.

As a result, as shown in FIG. 9, it was confirmed that HSP hardly exhibited cytotoxicity at a concentration of 0.5 μg/mL or less of pheophorbide a.

<Experimental Example 4> Confirmation of Cellular Phototoxicity of *Helicobacter pylori* Recognition Photosensitized Hybridization Polymer The cytotoxicity of the hybridized polymer butyl-poly(3SL-lysine)$_{10}$-Pheoa (HSP) synthesized as in the Example 1 was confirmed at the concentration and laser intensity showing antimicrobial activity.

AGS cells were dispensed into each well by 1 ml at a concentration of $2\times10^4$ cells/well in a 24-well plate and cultured at 37° C. and 5% $CO_2$ for 24 hours. After 24 hours, using a UV spectrophotometer, the polymer butyl-poly(3SL-lysine)$_{10}$-Pheoa (HSP) was treated with a serum-free RPMI medium at a concentration of 0.5 μg/mL based on pheophorbide a and the reaction was carried out under conditions of 37° C. and 5% $CO_2$ for 30 minutes, which showed efficacy in the antibacterial activity experiment.

After the reaction, the laser was irradiated in the range of 0-4.0 J/cm$^2$ using a laser of 50 mW intensity, and the MTT assay was performed to calculate the cell viability compared with the control.

As a control group, only pheophorbide a was treated at the same concentration as the polymer and the fluorescence intensity that appeared after treatment with the MTT solution was confirmed using a multi-reader (Synergy H1 Multi-mode Reader, Biotek) at 570 nm.

As a result, as shown in FIG. 10, in the control group treated with pheophorbide a at concentration of 0.5 μg/mL and incubated for 30 minutes and then irradiated with the laser, cytotoxicity appeared from 0.8 J/cm$^2$ laser intensity, and as the laser irradiation increased, cytotoxicity of about 50% was observed at 4.0 J/cm$^2$.

On the other hand, the hybridized polymer butyl-poly(3SL-lysine)$_{10}$-Pheoa (HSP) showed little cytotoxicity until 2.4 J/cm$^2$ laser irradiation, and a little cytotoxicity was confirmed from 3.2 J/cm$^2$ laser irradiation, and about 30% of cytotoxicity was confirmed at 4.0 J/cm$^2$.

From the above results, it was confirmed that butyl-poly(3SL-lysine)$_{10}$-Pheoa exhibited lower cytotoxicity than pheophorbide a.

<Experimental Example 5> Confirmation of Cellular Uptake of *Helicobacter pylori* Recognition Photosensitized Hybridization Polymer The level at which the hybridized polymer butyl-poly(3SL-lysine)$_{10}$-Pheoa (HSP) prepared in the Example 1 was absorbed into the cell was confirmed.

The concentrations of butyl-poly(3SL-lysine)$_{10}$-Pheoa and pheophorbide a were equally adjusted to a concentration of 0.5 ml based on pheophorbide a, and was treated with AGS cells, respectively and incubated at 36° C. for 30 minutes. After incubation, it was washed twice with DPBS, treated with trypsin and cells were collected and centrifuged (1500 rpm, 3 minutes) to remove the supernatant.

Thereafter, AGS cells were dispersed in 1 ml of DPBS at a concentration of $1\times10^5$ cells/ml, and the degree of cellular uptake of pheophorbide a and butyl-poly(3SL-lysine)$_{10}$-Pheoa absorbed by AGS cells was confirmed by the fluorescence intensity of pheophorbide a.

As a result, as shown in FIG. 13, it was confirmed that pheophorbide a was absorbed into the cells by $7\times10^2$ more than the control, whereas butyl-poly(3SL-lysine)$_{10}$-Pheoa had a level of pheophorbide a fluorescence intensity similar to that of the control group.

<Experimental Example 6> Confirmation of Antibacterial Activity of *Helicobacter pylori* Recognition Photosensitized Hybridization Polymer The effect of inactivating *Helicobacter pylori* of the hybridized polymer butyl-poly(3SL-lysine)$_{10}$-Pheoa (HSP) synthesized as in the Example 1 was confirmed.

In addition, the antibacterial activity effect between the hybridized polymers in which 3'-sialyllactose (3SL) or 6'-sialyllactose (6SL), which is an isomer of the 3'-sialyllactose representing *Helicobacter pylori* recognition therein, is bound was compared. The effect of the recognition ability of 3'-sialyllactose (3SL) of HSP on the antibacterial activity of *Helicobacter pylori* was confirmed by comparing with the experimental group of Pre3SL+butyl-poly(3SL-lysine)$_{10}$-Pheoa, which interacts competitively with sialyllactose.

*Helicobacter pylori* 26695 strain (*H. pylori* strain 26695) and *Helicobacter pylori* SS1 strain (*H. pylori* strain SS1) were distributed from the *Helicobacter pylori* strain bank. The strains were cultured using brucellabroth (Difco, USA; bacto tryptone 10 g, bacto peptamin 10 g, bacto dextrose 1 g, bacto yeast extract 2 g, sodium chloride 5 g, sodium bisulfite 0.1 g) to which 10% horse serum (Welgene, Korea) was added, with maintaining anaerobic conditions in an incubator of 10% $CO_2$, 95% or more humidity, and 37° C.

To 1 ml of each cultured *Helicobacter pylori* strain ($5\times10^5$ CFU/m), butyl-poly(3SL-lysine)$_{10}$-Pheoa (0.5 μg/ml concentration based on pheophorbide a) was added, mixed, and incubated at 37° C. for 30 minutes. After incubation, the supernatant was removed by centrifugation (4000 rpm, 2 minutes) and dispersed with 1 ml of distilled water (D.W.), and butyl-poly (3SL-lysine)$_{10}$-Pheoa that did not react with *Helicobacter pylori* was removed by repeating the above process twice and the antibacterial activity was evaluated by performing a CFU assay.

The antibacterial activity of hybridization polymer butyl-poly(6SL-lysine)$_{10}$-Pheoa to which 6'-sialyllactose (6SL) was bound conjugated also was evaluated in the same manner as described above.

In addition, in order to confirm the competitive recognition inhibition effect with 3'-sialyllactose (3SL), 5 mg/ml of 3SL was dissolved in distilled water and incubated with *Helicobacter pylori* at 37° C. for 30 minutes. After incubation, the supernatant was removed by centrifugation (4000 rpm, 2 minutes) and dispersed with 1 ml of distilled water and after repeating this process twice, butyl-poly(3SL-lysine)$_{10}$-Pheoa was added to incubate at 37° C. for 30 minutes.

After incubation, the supernatant was removed by centrifugation (4000 rpm, 2 minutes) and dispersed with 1 ml of distilled water, and the above process was repeated twice and the butyl-poly(3SL-lysine)$_{10}$-Pheoa that did not react with *Helicobacter pylori* was removed. Thereafter, the *Helicobacter pylori* 26695 strain experimental group was irradiated with laser for 0, 24, 48, 72, and 96 seconds at 50 mW intensity, and then CFU assay was performed, and in the experimental group of *Helicobacter pylori* SS1 strain, a CFU assay was performed by irradiating a laser for 0, 12, 48 and 60 seconds at an intensity of 50 mW.

As a result, in the case of the *Helicobacter pylori* 26695 strain treated with butyl-poly(3SL-lysine)$_{10}$-Pheoa (HSP) as shown in FIG. 11, in the experimental group irradiated with 1.2 J/cm$^2$ laser, the number of *Helicobacter pylori* colonies at the level of 5×10⁵ to 5×10⁴ CFU/ml decreased compared to the negative control group, and the growth of *Helicobacter pylori* in the experimental group irradiated with a laser of 2.4 J/cm² or more was no longer confirmed.

On the other hand, in the case of the butyl-poly(6SL-lysine)$_{10}$-Pheoa and Pre3SL+butyl-poly(3SL-lysine)$_{10}$-Pheoa control groups irradiated with the same laser conditions, it was confirmed that both did not interact properly with *Helicobacter pylori* and most of them were washed off in the washing step and showed very low antibacterial activity compared to butyl-poly(3SL-lysine)$_{10}$-Pheoa (HSP).

In addition, in the case of the *Helicobacter pylori* SS1 strain as shown in FIG. 12, compared to the negative control (NC) and the experimental group irradiated with only laser, in the experimental group treated with the hybridization polymer butyl-poly(3SL-lysine)$_{10}$-Pheoa (HSP), CFU (colony forming units) decreased from the experimental group irradiated with 1.2 J/cm² laser, and in the experimental group irradiated with 2.4 J/cm², *Helicobacter pylori* colonies did not appear, which was confirmed as the laser irradiation dose showing antibacterial activity. On the other hand, it was confirmed that in the butyl-poly(6SL-lysine)$_{10}$-Pheoa and Pre3SL+butyl-poly(3SL-lysine)$_{10}$-Pheoa controls, the number of *Helicobacter pylori* populations similar to those of the negative control was maintained.

From the above results, it was confirmed that butyl-poly(3SL-lysine)$_{10}$-Pheoa exhibited very excellent antibacterial activity of *Helicobacter pylori* when irradiated with a laser at an intensity of 2.4 J/cm², and butyl-poly(3SL-lysine)$_{10}$-Pheoa (HSP) interacted very excellently with *Helicobacter pylori* than the control group of butyl-poly(6SL-lysine)$_{10}$-Pheoa and Pre3SL+butyl-poly(3SL-lysine)$_{10}$-Pheoa.

<Experimental Example 7> Confirmation of Interaction and Inactivation of *Helicobacter pylori* Recognition Hybridization Material Using Confocal Microscopy Analysis It was confirmed that the *Helicobacter pylori* recognition hybridization polymer synthesized as in the Example 1 can interact with the *Helicobacter pylori* SS1 strain in vitro and can induce the inactivation of *Helicobacter pylori* by laser irradiation.

The hybridized polymer butyl-poly(3SL-lysine)$_{10}$-Pheoa (HSP) prepared in the Example 1 was quantified using a UV spectrophotometer based on pheophorbide a (1 µg/ml), then diluted with distilled water and mixed with *Helicobacter pylori* SS1 strain of 1×10⁶ CFU/ml and incubated at 37° C. for 2 hours.

In addition, butyl-poly(6SL-lysine)$_{10}$-Pheoa without *Helicobacter pylori* recognition was mixed with the *Helicobacter pylori* SS1 strain in the same process as above, and incubated at 37° C. for 2 hours, and the control group was designated as 6SL-LRP.

As another control, 3'-sialyllactose (Pre3SL) of 5 mg/ml was incubated with 1 ml (1×10⁶ CFU/ml) of *Helicobacter pylori* SS1 strain for 30 minutes in advance, and then centrifuged (4000 rpm, 2 minutes) to remove the supernatant. Then, it was redispersed with D.W and the above process was repeated twice. Thereafter, butyl-poly(3SL-lysine)$_{10}$-Pheoa was treated, and incubated at 37° C. for 2 hours and the control was designated as 3SL-LRHSP.

After the incubation of each experimental group was completed, each experimental group was centrifuged (4000 rpm, 2 minutes), and the supernatant was removed. Then, it was redispersed with D.W and the above process was repeated twice.

Thereafter, a laser of a total of 10 J/cm² was irradiated with 50 mW laser intensity, and *Helicobacter pylori* was stained with SYTO 9 and propidium iodide, and then of the fluorescence image was confirmed by SYTO 9 (green, Ex/Em 485/498), propidium iodide (red, Ex/Em 535/617) and Cy5 (purple, Ex/Em 650/670).

As a result, as shown in FIG. 14, in the case of HSP, it was confirmed that the fluorescence of SYTO 9 (Green) and the Cy5 (purple) fluorescence of pheophorbide a of 3SL-LRHSP, which appears in normal *Helicobacter pylori*, mostly coincide, and thus 3SL-LRHSP interacts with *Helicobacter pylori*. On the other hand, the experimental group treated with butyl-poly(6SL-lysine)$_{10}$-Pheoa (6SL-LRP) showed fluorescence of SYTO 9 (Green) in normal *Helicobacter pylori*, but fluorescence of Cy5 (purple) of pheophorbide a of HSP did not appear. As another experimental group, the experimental group (Pre3SL+LRHSP) treated with HSP after pretreatment of 3'-sialyllactose for 30 minutes also showed fluorescence of SYTO 9 (Green) in normal *Helicobacter pylori*, but did not show fluorescence of Cy5 of pheophorbide a of HSP (purple).

From the above results, it was confirmed that butyl-poly(6SL-lysine)$_{10}$-Pheoa and butyl-poly(3SL-lysine)$_{10}$-Pheoa treated after pretreatment with 3'-sialyllactose did not interact with *Helicobacter pylori*.

On the other hand, when comparing the laser-irradiated experimental group [indicated by Laser (+)] and the non-irradiated experimental group [indicated by Laser (−)], the 3SL-LRHSP experimental group has interaction between 3SL-LRHSP and *Helicobacter pylori* and the damage to the cell membrane of *Helicobacter pylori* is induced due to singlet oxygen generated in pheophorbide a of 3SL-LRHSP by laser irradiation and accordingly, propidium iodide (Red) which entered the inside of *Helicobacter pylori* to exhibit a fluorescence value was confirmed.

However, in the other 6SL-LRP Laser(+), Laser(−), Pre3SL+3SL-LRHSP Laser(+), and Laser(−) experimental groups, only SYTO 9 (Green) fluorescence appeared in normal *Helicobacter pylori* was confirmed depending on the presence or absence of laser irradiation. However, propidium iodide (Red) fluorescence was not confirmed.

From the above results, it was confirmed that as 3SL-LRHSP recognized *Helicobacter pylori* and interacted successfully, and thus *Helicobacter pylori* was effectively inactivated due to the singlet oxygen generated in pheophorbide a upon laser irradiation.

<Experimental Example 8> Confirmation of Treatment Effect of *Helicobacter pylori* Infection In Vivo of *Helicobacter pylori* Recognition Hybridization Polymer The treatment effect of *Helicobacter pylori* infection in vivo of the *Helicobacter pylori* recognition photosensitized hybridization polymer butyl-poly(3SL-lysine)$_{10}$-Pheoa (3SL-LRHSP) prepared as in the Example 1.

*Helicobacter pylori* (*H. pylori*) SS1 strain was cultured using brucellabroth (bacto tryptone 10 g, bacto peptamin 10 g, bacto dextrose 1 g, bacto yeast extract 2 g, sodium chloride 5 g, sodium bisulfite 0.1 g; Difco, USA) to which 10% horse serum was added. In order to maintain the anaerobic conditions, the incubator maintained 10% CO$_2$ and 95% or more humidity and the temperature was maintained at 37° C.

In addition, 200 µl (3×10⁸ CFU/m) of the *H. pylori* SS1 strain was orally administered to balb c mice three times every two days for a week to inoculate and induce infection.

After that, the infection was developed for 2 weeks and antibiotic-based triple therapy [OCA; omeprazole 400 µmol/kg, amoxicillin 68 µmol/kg, and clarithromycin 19.1 µmol/kg], which is effective in the treatment of *Helicobacter pylori* infection, was administered orally at 1-day intervals for 3 days (from 6 hours before oral administration, balb c was fasting), and 3SL-LRHSP [butyl-poly(3SL-lysine)$_{10}$-Pheoa (0.5 µg/ml concentration based on pheophorbide a)] was administered together at the third OCA administration, and after 30 minutes, the laser was irradiated into the stomach using a micro fiber laser.

For laser irradiation, 40 mW laser was irradiated for 250 seconds for a total of 10 J/cm², and the same amount of laser was irradiated to the animal experimental group to which PBS and OCA were administered as a control group for further comparison (The laser-irradiated group is marked with (+), the laser-non-irradiated group is marked with (−)). Two days after the final drug administration, the stomach of the balb c was removed and the stomach was divided into half, the stomach tissue was washed with 10 ml of PBS, the suspended matter in the stomach was filtered using a cell strainer, and the CFU assay was performed using the remaining *H. pylori* SS1 strain solution.

The medium used for the CFU assay included Skirrow's supplement [vancomycin (10 mg/l), polymyxin B (2-5 IU/ml), trimethoprim (5 mg/l)], and after 2-3 days, the number of colonies appeared on the medium was counted, and the treatment effect against infection of the *Helicobacter pylori* recognition photosensitized hybridization material was finally confirmed through CFU assay.

As a result, in the case of the PBS(−) and PBS(+) groups as shown in FIG. 15, *Helicobacter pylori* colonies of about 1.1×10⁷ CFU/stomach and 1.4×10⁷ CFU/stomach were confirmed, respectively, and in OCA(−) and OCA(+) experimental groups, *Helicobacter pylori* colonies of 2.6×10⁶ and 4.4×10⁶ CFU/stomach were identified, respectively. Finally, in the 3SL-LRHSP(−) and 3SL-LRHSP(+) experimental groups, the *Helicobacter pylori* colonies of 1.6×10⁷ and 6.7×10⁴ CFU/stomach were confirmed, respectively.

From the above results, as the CFU assay results of PBS(−), PBS(+) and 3SL-LRHSP(−) experimental groups were confirmed to be similar levels, in the experimental groups, the effect of reducing the infection level of *Helicobacter pylori* by the presence or absence of laser irradiation was not significantly different. In addition, it was confirmed that the effects of the presence or absence of laser irradiation hardly appear in the OCA(−) and OCA(+) control groups, which are antibiotic-based methods for treating *Helicobacter pylori* conventionally.

On the other hand, it was confirmed that colonies of the experimental group treated with 3SL-LRHSP were reduced by about 1.5×10² to 2.3×10² times compared to those of PBS(−), PBS(+) and 3SL-LRHSP(−), and were reduced by 3.8 to 6.5 times compared to the OCA(−) and OCA(+) experimental groups treated with the existing therapeutic agent for *Helicobacter pylori*.

Colony reduction means that the number of *Helicobacter pylori* having an infectious power in the gastrointestinal tract has been reduced, and it was confirmed that the infection treatment effect of *Helicobacter pylori* recognition photosensitized hybridization polymer prepared as in the Example 1 exhibited about 3.8 to 6.8 times better than that of *Helicobacter pylori* treatment using conventional antibiotics.

<Experimental Example 9> Confirmation of *Helicobacter pylori* Antibacterial Activity In Vitro of Polylysine-Based *Helicobacter pylori* Recognition Photosensitized Hybridization Material The concentration showing the *Helicobacter pylori* inactivation effect and antibacterial activity of polylysine-based *Helicobacter pylori* recognition photosensitized hybridization material, butyl-poly(3SL-lysine)$_{10}$-Ce6, butyl-poly(3SL-lysine)$_{10}$-PPIX, butyl-poly(3SL-lysine)$_{10}$-HPP and butyl-poly(3SL-lysine)$_{10}$-SSiPC prepared in the Examples 2, 3, 4 and 5 were confirmed in vitro.

1. Experimental Method

*Helicobacter pylori* strain SS1 was distributed from the *Helicobacter pylori* strain bank. The strains were cultured using brucellabroth (Difco, USA) to which 10% horse serum (Welgene, Korea) was added, and the composition of the medium was bacto tryptone 10 g, bacto peptamin 10 g, bactodextrose 1 g, bacto yeast extract 2 g, sodium chloride 5 g and sodium bisulfite 0.1 g. In order to maintain the anaerobic conditions, the incubator maintained 10% $CO_2$ and 95% or more humidity, and the temperature was maintained at 37° C.

In addition, in order to confirm the recognition effect of 3'-sialyllactose (denoted as 3SL) in 1 ml (5×10⁵ CFU/ml) of *Helicobacter pylori* (SS1 strain), the same concentration of free photosensitizers (Ce6, PPIX, HPP, SSiPC) was dissolved in DMSO in excess and diluted with distilled water to match each concentration of *Helicobacter pylori* recognition complex.

In addition, each material was incubated with *Helicobacter pylori* in advance at 37° C. for 30 minutes. After incubation, the supernatant was removed by centrifugation at 4000 rpm for 2 minutes and dispersed using 1 ml of PBS. After repeating the above process twice to remove unreacted substances that did not react with *Helicobacter pylori*, it was mixed with butyl-poly(3SL-lysine)$_{10}$-Ce6, butyl-poly(3SL-lysine)$_{10}$-PPIX, butyl-poly(3SL-lysine)$_{10}$-HPP, butyl-poly(3SL-lysine)$_{10}$-SSiPC (0-50 µg/ml concentration based on each photosensitizer Ce6, PPIX, HPP, SSiPC) and incubated at 37° C. for 30 minutes. After incubation, the supernatant was removed by centrifugation at 4000 rpm for 2 minutes, and then re-dispersed using 1 ml of PBS. The above process was repeated twice to remove unreacted substances that did not react with *Helicobacter pylori*.

After that, each experimental group was irradiated with a laser at 50 mW intensity for 200 seconds, and then diluted to proceed with CFU assay.

2. Experiment Result

As shown in FIG. 37, as butyl-poly(3SL-lysine)$_{10}$-Ce6 decreases the number of *Helicobacter pylori* colonies from 0.5 µg/ml based on Ce6 concentration, and colonies hardly appear at 1.0 µg/ml, and thus it was confirmed an appropriate concentration showing antibacterial activity upon laser irradiation (10.0 J/cm²). In addition, butyl-poly(3SL-lysine)$_{10}$-PPIX decreased the number of *Helicobacter pylori* colonies from 5.0 µg/ml based on the PPIX concentration, and colonies hardly appear at 10.0 µg/ml, and thus it was confirmed an appropriate concentration showing antibacterial activity upon laser irradiation (10.0 J/cm²).

On the other hand, in *Helicobacter pylori* colonies treated with free Ce6 and PPIX as a control, respectively, a colony result value was found to be more than half thereof compared to those of the NC group at 50.0 µg/ml based on free Ce6 and PPIX concentrations.

Figure 38:
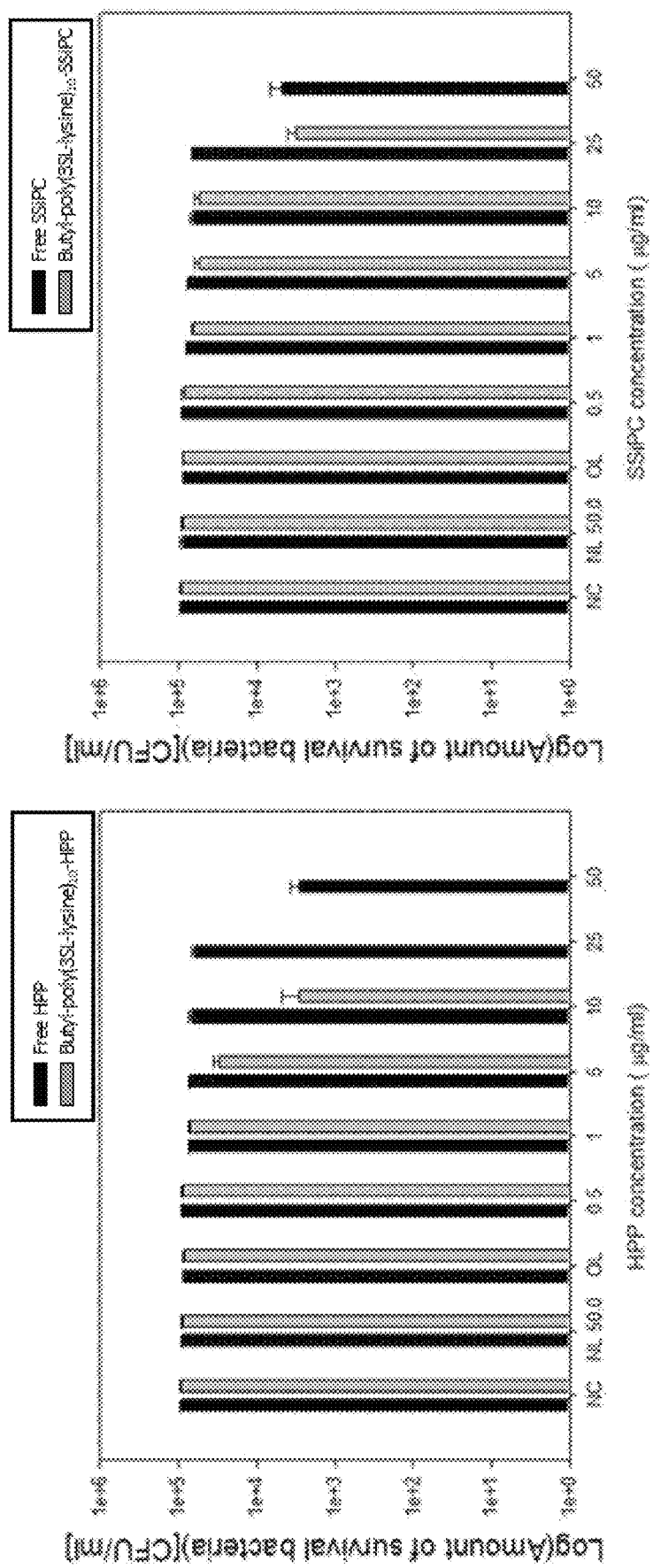
FIG. 38 shows a CFU (Colony forming units) analysis result of confirming the antibacterial activity of butyl-poly (3SL-lysine)$_{10}$-HPP and butyl-poly(3SL-lysine)$_{10}$-SSiPC against *Helicobacter pylori* bacteria.

Meanwhile, referring to FIG. 38, when a laser at 10.0 J/cm² was irradiated at 10.0 µg/ml of [butyl-poly(3SL-lysine)$_{10}$-HPP] based on HPP concentration, the number of Helicobacter pylori colonies was decreased from 1×10⁵ CFU/ml to 3×10³ CFU/ml, and in particular, at a concentration of 25.0 µg/ml or more based on HPP concentration, it was confirmed that Helicobacter pylori no longer grows compared to the free HPP control group as the control group. In addition, when a laser (10.0 J/cm²) was irradiated at 25.0 µg/ml of [butyl-poly(3SL-lysine)$_{10}$-SSiPC] based on SSiPC concentration, the number of Helicobacter pylori colonies was decreased from 1×10⁵ CFU/ml to 4×10³ CFU/ml, and colonies did not appear at 50.0 µg/ml, and it was confirmed that the concentration was appropriate to show antibacterial activity when irradiated with a laser (10.0 J/cm²).

On the other hand, in Helicobacter pylori colonies treated with free HPP and SSiPC as a control, respectively, a colony result value was found to be more than half thereof compared to those of the NC group at 50.0 µg/ml based on free HPP and SSiPC concentrations.

From the above results, butyl-poly(3SL-lysine)$_{10}$-Ce6, butyl-poly(3SL-lysine)$_{10}$-PPIX, butyl-poly(3SL-lysine)$_{10}$-HPP and butyl-poly(3SL-lysine)$_{10}$-SSiPC hybridization materials have excellent Helicobacter pylori inactivation effect, while it was confirmed that free Ce6, PPIX, HPP and SSiPC did not have sialyllactose (3SL) that interacts with Helicobacter pylori when irradiated with the same amount of laser, so they did not interact properly with Helicobacter pylori and thus it was confirmed that the effect of antibacterial activity hardly appeared and the hybridization materials exhibited excellent Helicobacter pylori recognition ability to improve the antibacterial activity effect.

<Experimental Example 10> Confirmation of Helicobacter pylori Antibacterial Activity In Vitro of Chitosan-Based Helicobacter pylori Recognition Photosensitized Hybridization Material The concentration showing the Helicobacter pylori inactivation effect and antibacterial activity of chitosan-based Helicobacter pylori recognition photosensitized hybridization material, 3'-sialyllactose-chitosan-pheophorbide a (3SL-Chitosan-Pheoa) prepared in the Example 6 were confirmed in vitro.

Compared to the negative control (marked as NC) and the experimental group that only irradiated laser (marked as only laser) based on Helicobacter pylori (SS1 strain) 5×10⁵ CFU/ml by performing the CFU assay in the same procedure as the previous experimental method of Experimental Example 9, the number of colonies of the 3SL-Chitosan-Pheoa which is chitosan-based Helicobacter pylori recognition photosensitized hybridization material and free Pheoa control group was confirmed.

As a result, as shown in FIG. 39, in the case of 3SL-Chitosan-Pheoa, the number of Helicobacter pylori colonies began to decrease from 10.0 µg/ml based on the Pheoa concentration, and colonies did not appear at 25.0 µg/ml and it was confirmed that the concentration was appropriate to show antibacterial activity when irradiated with a laser (10.0 J/cm²). On the other hand, in the control experimental group, free Pheoa, the result of colony at 50.0 µg/ml based on the Pheoa concentration was slightly less than half compared to that of NC.

From the above results, it was confirmed that at a concentration of 25.0 µg/ml or more based on the Pheoa concentration, Helicobacter pylori did not grow any more than the free Pheoa control group, indicating the excellent antibacterial activity of 3SL-Chitosan-Pheoa, whereas when the same amount of laser was irradiated with the free Pheoa, sialyllactose (3SL) that interacts with Helicobacter pylori did not exist, so it did not interact properly with Helicobacter pylori and substances that did not interact with Helicobacter pylori in the subsequent washing step were mostly washed away, and it was confirmed that it hardly exhibited antibacterial activity compared to the Helicobacter pylori hybridization material, 3SL-Chitosan-Pheoa.

<Experimental Example 11> Confirmation of Helicobacter pylori Antibacterial Activity In Vitro of Polyethylene Glycol (PEG)-Based Helicobacter pylori Recognition Photosensitized Hybridization Material The concentration showing the Helicobacter pylori inactivation effect and antibacterial activity of PEG-based Helicobacter pylori recognition photosensitized hybridization material, 3'-Sialyllactose-PEG-Pheophorbide a (3SL-PEG-Pheoa) prepared in the Example 7 were confirmed in vitro.

1. Experimental Method

Helicobacter pylori strain SS1 was distributed from the Helicobacter pylori strain bank. The strains were cultured using brucellabroth (Difco, USA) to which 10% horse serum (Welgene, Korea) was added, and the composition of the medium was bacto tryptone 10 g, bacto peptamin 10 g, bactodextrose 1 g, bacto yeast extract 2 g, sodium chloride 5 g and sodium bisulfite 0.1 g. In order to maintain the anaerobic conditions, the incubator maintained 10% $CO_2$ and 95% or more humidity, and the temperature was maintained at 37° C.

In addition, after fixing the concentration of 3SL-PEG-Pheoa in 1 ml (1×10⁵ CFU/m) of Helicobacter pylori (26695 strain) (50 µg/ml), the photodynamic antibacterial treatment effect according to the laser intensity was confirmed. In addition, each material was incubated with Helicobacter pylori at 37° C. for 30 minutes in advance.

After incubation, the supernatant was removed by centrifugation at 4000 rpm for 2 minutes and dispersed using 1 ml of PBS. The above process was repeated twice to remove unreacted substances that did not react with Helicobacter pylori, and then mixed with 3SL-PEG-Pheoa (50 µg/ml concentration based on Pheoa) and incubated at 37° C. for 30 minutes. After incubation, the supernatant was removed by centrifugation at 4000 rpm for 2 minutes, and re-dispersed using 1 ml of PBS. The above process was repeated twice to remove unreacted substances that did not react with Helicobacter pylori.

After that, after spreading the Helicobacter pylori in Brucellebroth agar medium evenly on the plate, each experimental group was irradiated with a laser of 0-50 J/cm² at an intensity of 100 mW, and two days later, the formation of an inhibition zone for the photodynamic treatment effect was confirmed on the plate by 3SL-PEG-Pheoa.

2. Experiment Result

As shown in FIG. 40, in the case of 3SL-PEG-Pheoa, an inhibition zone in which Helicobacter pylori does not grow was confirmed when a laser at 10.0 J/cm² was irradiated at 50.0 µg/ml based on the Pheoa concentration, and even at laser intensities of 30, 40, and 50 J/cm², the inhibition zone was also identified. On the other hand, in the comparative group to which the laser was not irradiated, no inhibition zone was found.

From the above results, it was confirmed that the 3SL-PEG-Pheoa hybridization material can exhibit an excellent *Helicobacter pylori* inactivation effect, and in particular, has the potential of a hybridization material capable of photodynamic inactivation of *Helicobacter pylori*.

<Experimental Example 12> Confirmation of *Helicobacter pylori* Antibacterial Activity In Vitro of Pullulan-Based *Helicobacter pylori* Recognition Photosensitized Hybridization Material The concentration showing the *Helicobacter pylori* inactivation effect and antibacterial activity of pullulan-based *Helicobacter pylori* recognition photosensitized hybridization material, 3'-Sialyllactose-Pullulan-Pheophorbide a (3SL-PU-Pheoa) prepared in the Example 8 were confirmed in vitro.

Compared to the negative control (marked as NC) and the experimental group that only irradiated laser (marked as only laser) based on *Helicobacter pylori* (SS1 strain) $5 \times 10^5$ CFU/ml by performing the CFU assay in the same procedure as the previous experimental method of Experimental Example 9, the number of colonies of the 3SL-PU-Pheoa which is pullulan-based *Helicobacter pylori* recognition photosensitized hybridization material and free Pheoa control group was confirmed.

As a result, in the case of 3SL-PU-Pheoa as shown in FIG. 41, the number of *Helicobacter pylori* colonies was confirmed to decrease from $1 \times 10^5$ CFU/ml to $5 \times 10^3$ CFU/ml when irradiated with 10.0 J/cm² laser at 20.0 μg/ml based on Pheoa concentration. On the other hand, at a concentration of 50.0 μg/ml or more based on the Pheoa concentration, it was confirmed that *Helicobacter pylori* did not grow any more than the free Pheoa control group.

On the other hand, in the free Pheoa control group, when the same amount of laser was irradiated, a *Helicobacter pylori* colony of $9 \times 10^2$ CFU/ml could be confirmed even at 50.0 μg/ml based on the Pheoa concentration.

From the above results, it was confirmed that the 3SL-Chitosan-Pheoa hybridization material exhibits excellent antibacterial activity of *Helicobacter pylori*.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A polymer composite for recognizing *Helicobacter pylori* comprising a photosensitizer; sialyllactose; and a water-soluble polymer as a linker,
wherein the polymer composite for recognizing the *Helicobacter pylori* is represented by Chemical Formula 1:

[Chemical Formula 1]

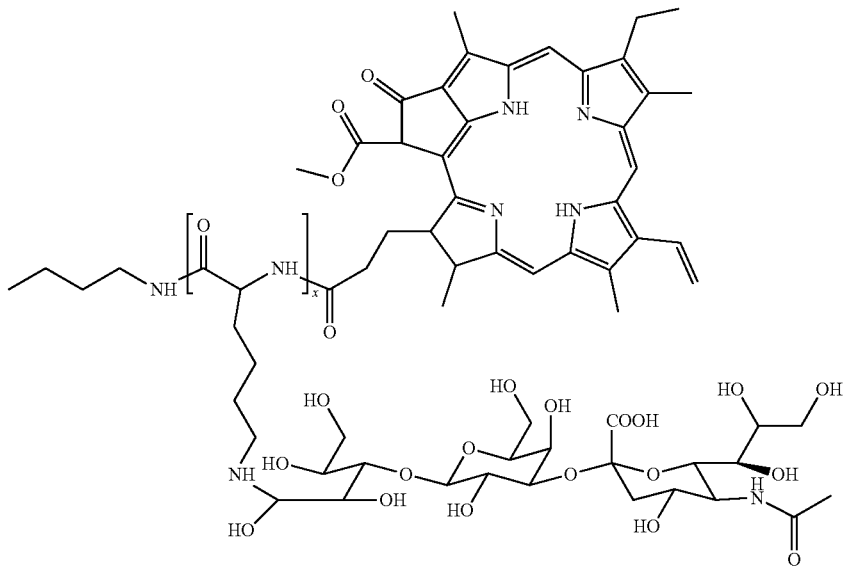

in which X is an integer of 1 to 15.

2. The polymer composite for recognizing *Helicobacter pylori* of claim 1, wherein the polymer composite is effective against a *Helicobacter pylori* strain selected from the group consisting of *Helicobacter pylori* 26695, *Helicobacter pylori* SS1, *Helicobacter pylori* 51 and *Helicobacter pylori* 52.

* * * * *